(12) United States Patent
Röhrig et al.

(10) Patent No.: US 9,918,969 B2
(45) Date of Patent: *Mar. 20, 2018

(54) SUBSTITUTED OXOPYRIDINE DERIVATIVES AND USE THEREOF AS FACTOR XIA/PLASMA

(71) Applicant: Bayer Pharma Aktiengesellschaft, Berlin (DE)

(72) Inventors: Susanne Röhrig, Hilden (DE); Alexander Hillisch, Solingen (DE); Julia Straßburger, Wuppertal (DE); Stefan Heitmeier, Wülfrath (DE); Martina Victoria Schmidt, Köln (DE); Karl-Heinz Schlemmer, Wuppertal (DE); Anja Buchmüller, Essen (DE); Christoph Gerdes, Köln (DE); Henrik Teller, Schwaan (DE); Martina Schäfer, Berlin (DE); Adrian Tersteegen, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/332,893

(22) Filed: Oct. 24, 2016

(65) Prior Publication Data

US 2017/0035739 A1 Feb. 9, 2017

Related U.S. Application Data

(62) Division of application No. 14/906,771, filed as application No. PCT/EP2014/065608 on Jul. 21, 2014, now Pat. No. 9,475,809.

(30) Foreign Application Priority Data

Jul. 23, 2013 (EP) .................................... 13177605

(51) Int. Cl.
*A61K 31/438* (2006.01)
*A61K 31/437* (2006.01)
*C07D 215/227* (2006.01)
*C07D 221/04* (2006.01)
*C07D 401/12* (2006.01)
*C07D 413/12* (2006.01)
*C07D 471/04* (2006.01)

(52) U.S. Cl.
CPC .......... *A61K 31/438* (2013.01); *A61K 31/437* (2013.01); *C07D 215/227* (2013.01); *C07D 221/04* (2013.01); *C07D 401/12* (2013.01); *C07D 413/12* (2013.01); *C07D 471/04* (2013.01)

(58) Field of Classification Search
CPC ............................ A61K 31/438; A61K 31/437
USPC ....................................................... 514/300
See application file for complete search history.

(56) References Cited

U.S. PATENT DOCUMENTS 9,475,809 B2 * 10/2016 Rohrig ............... C07D 215/227

FOREIGN PATENT DOCUMENTS

| WO | 2006/030032 | A1 | 3/2006 | |
|---|---|---|---|---|
| WO | 2008/079787 | A2 | 7/2008 | |
| WO | 2013/093484 | A1 | 6/2013 | |
| WO | WO-2013093484 | A1 * | 6/2013 | ........... C07D 401/14 |

OTHER PUBLICATIONS

European Patent Office, Written Opinion (with English translation) for International Patent Application No. PCT/EP2014/065608, dated Jan. 29, 2015, 9 pages.

International Bureau of WIPO, International Preliminary Report on Patentability for International Patent Application No. PCT/EP2014/065608, dated Jan. 26, 2016, 6 pages.

* cited by examiner

*Primary Examiner* — Yong L Chu
(74) *Attorney, Agent, or Firm* — Nixon & Vanderhye P.C.

(57) ABSTRACT

The invention relates to substituted oxopyridine derivatives and to processes for their preparation, and also to their use for preparing medicaments for the treatment and/or prophylaxis of diseases, in particular cardiovascular disorders, preferably thrombotic or thromboembolic disorders, and oedemas, and also ophthalmic disorders.

3 Claims, No Drawings

SUBSTITUTED OXOPYRIDINE DERIVATIVES AND USE THEREOF AS FACTOR XIA/PLASMA

CROSS-REFERENCE TO RELATED APPLICATIONS

The present application is a divisional of U.S. patent application Ser. No. 14/906,771, filed on Jan. 21, 2016 issued as U.S. Pat. No. 9,475,809 and titled SUBSTITUTED OXOPYRIDINE DERIVATIVES AND USE THEREOF AS FACTOR XIA/PLASMA, which is a U.S. national stage application of International Patent Application No. PCT/EP2014/065608, filed Jul. 21, 2014 and titled SUBSTITUTED OXOPYRIDINE DERIVATIVES AND USE THEREOF AS FACTOR XIA/PLASMA, which claims priority to European Patent Application 13177605.6, filed Jul. 23, 2013 and titled SUBSTITUTED OXOPYRIDINE DERIVATIVES AND USE THEREOF AS FACTOR XIA/PLASMA, the contents of all of which are hereby incorporated by reference in their entirety.

The invention relates to substituted oxopyridine derivatives and to processes for their preparation, and also to their use for preparing medicaments for the treatment and/or prophylaxis of diseases, in particular cardiovascular disorders, preferably thrombotic or thromboembolic disorders, and oedemas, and also ophthalmic disorders.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a final joint reaction path, are distinguished. Here, factors Xa and IIa (thrombin) play key roles: Factor Xa bundles the signals of the two coagulation paths since it is formed both via factor VIIa/tissue factor (extrinsic path) and via the tenase complex (intrinsic path) by conversion of factor X. The activated serine protease Xa cleaves prothrombin to thrombin which, via a series of reactions, transduces the impulses from the cascade to the coagulation state of the blood.

In the more recent past, the traditional theory of two separate regions of the coagulation cascade (extrinsic and intrinsic path) has been modified owing to new findings: In these models, coagulation is initiated by binding of activated factor VIIa to tissue factor (TF). The resulting complex activates factor X, which in turn leads to generation of thrombin with subsequent production of fibrin and platelet activation (via PAR-1) as injury-sealing end products of hemostasis. Compared to the subsequent amplification/propagation phase, the thrombin production rate in this first phase is low and as a result of the occurrence of TFPI as inhibitor of the TF-FVIIa-FX complex is limited in time.

A central component of the transition from initiation to amplification and propagation of coagulation is factor XIa: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated leading to strong thrombus growth and stabilizing the thrombus.

In addition, it becomes the focus that, in addition to the stimulation via tissue factor, the coagulation system can be activated particularly on negatively charged surfaces, which include not only surface structures of foreign cells (e.g. bacteria) but also artificial surfaces such as vascular prostheses, stents and extracorporeal circulation. On the surface, initially factor XII (FXII) is activated to factor XIIa which subsequently activates factor XI, attached to cell surfaces, to factor XIa. This leads to further activation of the coagulation cascade as described above. In addition, factor XIIa also activates bound plasma prokallikrein to plasma kallikrein (PK) which, in a potentiation loop, firstly leads to further factor XII activation, overall resulting in amplification of the initiation of the coagulation cascade. In addition, PK is an important bradikinin-releasing protease which, inter alia, thus leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

Uncontrolled activation of the coagulation system or defective inhibition of the activation processes may lead to the formation of local thromboses or embolisms in vessels (arteries, veins, lymph vessels) or cardiac cavities. In addition, systemic hypercoaguability may lead to system-wide formation of thrombi and finally to consumption coagulopathy in the context of a disseminated intravasal coagulation. Thromboembolic complications may also occur in extracorporeal circulatory systems such as during hemodialysis and also in vascular prostheses or prosthetic heart valves and stents.

In the course of many cardiovascular and metabolic disorders, there is an increased tendency for coagulation and platelet activation owing to systemic factors such as hyperlipidaemia, diabetes or smoking, owing to changes in blood flow with stasis, for example in atrial fibrillation, or owing to pathological changes in vessel walls, for example endothelial dysfunctions or atherosclerosis. This unwanted and excessive activation of coagulation may, by formation of fibrin- and platelet-rich thrombi, lead to thromboembolic disorders and thrombotic complications with life-threatening conditions Inflammable processes may also be involved here. Accordingly, thromboembolic disorders are still the most frequent cause of morbidity and mortality in most industrialized countries.

The anticoagulants known from the prior art, that is to say substances for inhibiting or preventing blood coagulation, have various disadvantages. Accordingly, in practice, efficient treatment methods or the prophylaxis of thrombotic/thromboembolic disorders is found to be very difficult and unsatisfactory.

In the therapy and prophylaxis of thromboembolic disorders, use is made, firstly, of heparin which is administered parenterally or subcutaneously. Because of more favourable pharmacokinetic properties, preference is these days increasingly given to low-molecular-weight heparin; however, the known disadvantages described hereinbelow encountered in heparin therapy cannot be avoided either in this manner. Thus, heparin is orally ineffective and has only a comparatively short half-life. In addition, there is a high risk of bleeding, there may in particular be cerebral hemorrhages and bleeding in the gastrointestinal tract, and there may be thrombopaenia, alopecia medicomentosa or osteoporosis. Low-molecular-weight heparins do have a lower probability of leading to the development of heparin-induced thrombocytopaenia; however, they can also only be administered subcutaneously. This also applies to fondaparinux, a synthetically produced selective factor Xa inhibitor having a long half-life.

A second class of anticoagulants are the vitamin K antagonists. These include, for example, 1,3-indanediones and in particular compounds such as warfarin, phenprocoumon, dicumarol and other coumarin derivatives which non-selectively inhibit the synthesis of various products of certain vitamin K-dependent coagulation factors in the liver. Owing to the mechanism of action, the onset of action is only very slow (latency to the onset of action 36 to 48 hours). The compounds can be administered orally; however, owing to the high risk of bleeding and the narrow therapeutic index complicated individual adjustment and monitoring of the patient are required. In addition, other side-effects such as gastrointestinal problems, hair loss and skin necroses have been described.

More recent approaches for oral anticoagulants are in various phases of clinical evaluation or in clinical use, and have demonstrated their effectiveness in various studies. However, taking these medicaments can also lead to bleeding complications, particularly in predisposed patients. Thus, for antithrombotic medicaments, the therapeutic window is of central importance: The interval between the therapeutically active dose for coagulation inhibition and the dose where bleeding may occur should be as large as possible so that maximum therapeutic activity is achieved at a minimum risk profile.

In various in vitro and in vivo models with, for example, antibodies as factor XIa inhibitors, but also in factor XIa knock-out models, the antithrombotic effect with small/no prolongation of bleeding time or extension of blood volume was confirmed. In clinical studies, elevated factor XIa concentrations were associated with an increased event rate. In contrast, factor XI deficiency (hemophilia C) did not lead to spontaneous bleeding and was apparent only in the course of surgical operations and traumata, but did show protection with respect to certain thromboembolic events.

In addition, plasma kallikrein (PK) is associated with other disorders, which are associated with increased vascular permeability or chronic inflammatory disorders such as is the case in diabetic retinopathy, macular oedema and hereditary angiooedema or chronic inflammatory intestinal disorders. Diabetic retinopathy is primarily caused by microvascular deficiency, which leads to basal membrane thickening of the vessels and loss of vascularized pericytes followed by vascular occlusion and retinal ischemia which, owing to the retinal hypoxia thus caused, may lead to enhanced vessel permeability with subsequent formation of a macular oedema and, due to all of the processes present, to the patient going blind. In hereditary angiooedema (HAE), reduced formation of the physiological kallikrein inhibitor C1-esterase inhibitor causes uncontrolled plasma kallikrein activation leading to inflammations with fulminant oedema formation and strong pains. From experimental animal models, there are indications that inhibition of plasma kallikrein inhibits increased vascular permeability and may therefore prevent formation of a macular oedema and/or diabetic retinopathy or may improve the acute symptoms of HAE. Oral plasma kallikrein inhibitors could also be used for prophylaxis of HAE.

The kinins generated by means of plasma kallikrein especially have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Furthermore, for many disorders the combination of antithrombotic and antiinflammtory principles may also be particularly attractive to prevent the mutual enhancement of coagulation and inflammation.

It is therefore an object of the present invention to provide novel compounds for the treatment of cardiovascular disorders, in particular of thrombotic or thromboembolic disorders, and/or oedematous disorders, and/or ophthalmic disorders, in particular diabetic retinopathy and/or macular oedema, in humans and animals, which compounds have a wide therapeutic bandwidth.

WO 2006/030032 describes inter alia substituted pyridinones as allosteric modulators of the mGluR2 receptor, and WO 2008/079787 describes substituted pyridin-2-ones and their use as glucokinase activators.

The invention provides compounds of the formula

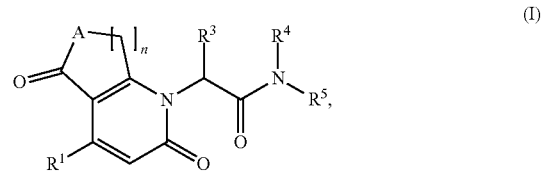

(I)

in which
n represents the number 1 or 2,
A represents —N(R$^2$)— or —CH$_2$—,
wherein
R$^2$ represents hydrogen or C$_1$-C$_4$-alkyl,
R$^1$ represents a group of the formula

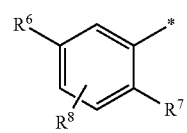

where * is the point of attachment to the oxopyridine ring,
R$^6$ represents bromine, chlorine, fluorine, methyl, difluoromethyl, trifluoromethyl, methoxy, difluoromethoxy or trifluoromethoxy,
R$^7$ represents hydrogen, bromine, chlorine, fluorine, cyano, nitro, hydroxy, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl,
R$^8$ represents hydrogen, chlorine or fluorine,
R$^3$ represents hydrogen,
R$^4$ represents hydrogen,
R$^5$ represents a group of the formula

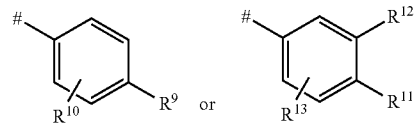

where # is the attachment site to the nitrogen atom,
R$^9$ represents hydroxycarbonyl or 5-membered heterocyclyl, where heterocyclyl may be substituted by 1 to 2 substituents independently of one another selected from the group consisting of oxo, hydroxy, thioxo, sulphanyl, methyl, difluoromethyl, trifluoromethyl, 2-hydroxycarbonyl-1,1,2,2-tetrafluoroethyl and 2-methoxycarbonyl-1,1, 2,2-tetrafluoroethyl, where methyl may be substituted by a methoxy substituent, $R^{10}$ represents hydrogen, chlorine, fluorine or methyl, $R^{11}$ and $R^{12}$ together with the carbon atoms to which they are bonded form a 5-membered heterocycle, where the heterocycle may be substituted by 1 to 2 substituents independently of one another selected from the group consisting of oxo, chlorine, hydroxy, hydroxycarbonyl, methyl, difluoromethyl, trifluoromethyl, 1,1,2,2,2-pentafluoroethyl, 2-hydroxycarbonyl-1,1,2,2-tetrafluoroethyl and 2-methoxycarbonyl-1,1,2,2-tetrafluoroethyl, $R^{13}$ represents hydrogen, chlorine, fluorine, methyl or methoxy, and the salts thereof, the solvates thereof and the solvates of the salts thereof.

Compounds according to the invention are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

The inventive compounds may, depending on their structure, exist in different stereoisomeric forms, i.e. in the form of configurational isomers or else, if appropriate, of conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of an inventive compound is understood here as meaning a compound in which at least one atom within the inventive compound has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^{3}H$ or $^{14}C$ isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the inventive compounds may therefore in some cases also constitute a preferred embodiment of the present invention. Isotopic variants of the compounds according to the invention can be prepared by the processes known to those skilled in the art, for example by the methods described further below and the procedures described in the working examples, by using corresponding isotopic modifications of the respective reagents and/or starting compounds.

Preferred salts in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates in the context of the invention are described as those forms of the inventive compounds which form a complex in the solid or liquid state by coordination with solvent molecules. Hydrates are a specific form of the solvates in which the coordination is with water.

The present invention additionally also encompasses prodrugs of the inventive compounds. The term "prodrugs" encompasses compounds which for their part may be biologically active or inactive but are converted during their residence time in the body into compounds according to the invention (for example by metabolism or hydrolysis).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, unless specified otherwise, the substituents are defined as follows:

Alkyl represents a straight-chain or branched alkyl radical having 1 to 5 carbon atoms, preferably 1 to 3 carbon atoms, by way of example and with preference methyl, ethyl, n-propyl, isopropyl, 2-methylprop-1-yl, n-butyl, tert-butyl and 2,2-dimethylprop-1-yl.

Cycloalkyl represents a monocyclic cycloalkyl group having 3 to 6 carbon atoms, preferred examples of cycloalkyl being cyclopropyl, cyclobutyl, cyclopentyl and cyclohexyl.

5-membered heterocyclyl in the definition of the radical $R^9$ represents a saturated, partially unsaturated or aromatic monocyclic radical having 5 ring atoms and up to 4 heteroatoms from the group consisting of S, O and N, where a nitrogen atom may also form an N-oxide, by way of example and with preference thienyl, furyl, pyrrolyl, thiazolyl, oxazolyl, isoxazolyl, oxadiazolyl, pyrazolyl, imidazolyl, triazolyl and tetrazolyl.

5-membered heterocycle in the definition of the radicals $R^{11}$ and $R^{12}$ represents a saturated, partially unsaturated or aromatic monocyclic radical having 5 ring atoms and up to 2 heteroatoms from the group consisting of S, O and N, where a nitrogen atom may also form an N-oxide. This 5-membered heterocycle together with the phenyl ring to which it is attached represents, by way of example and with preference, 2,3-dihydro-1-benzothiophen-5-yl, 1,3-dihydro-2-benzothiophen-5-yl, 2,3-dihydro-1-benzofuran-5-yl, 1,3-dihydro-2-benzofuran-5-yl, indolin-5-yl, isoindolin-5-yl, 2,3-dihydro-1H-indazol-5-yl, 2,3-dihydro-1H-benzimidazol-5-yl, 1, 3-dihydro-2, 1-benzoxazol-5-yl, 2,3-dihydro-1, 3-benzoxazol-5-yl, 1,3-dihydro-2, 1-benzothiazol-5-yl, 2,3-dihydro-1,3-benzothiazol-5-yl, 1H-benzimidazol-5-yl, 1H-indazol-5-yl, 1,2-benzoxazol-5-yl, indol-5-yl, isoindol-5-yl, benzofuran-5-yl, benzothiophen-5-yl, 2,3-dihydro-1-benzothiophen-6-yl, 1, 3-dihydro-2-benzothiophen-6-yl, 2,3-dihydro-1-benzofuran-6-yl, 1,3-dihydro-2-benzofuran-6-yl, indolin-6-yl, isoindolin-6-yl, 2,3-dihydro-1H-indazol-6-yl, 2,3-dihydro-1H-benzimidazol-6-yl, 1, 3-dihydro-2, 1-benzoxazol-6-yl, 2,3-dihydro-1,3-benzoxazol-6-yl, 1,3-dihydro-2, 1-benzothiazol-6-yl, 2,3-dihydro-1,3-benzothiazol-6-yl, 1H-benzimidazol-6-yl, 1H-indazol-6-yl, 1,2-benzoxazol-6-yl, indol-6-yl, isoindol-6-yl, benzofuran-6-yl and benzothiophen-6-yl.

4- to 6-membered oxoheterocyclyl in the definition of the radical $R^3$ represents a saturated monocyclic radical having 4 to 6 ring atoms in which one ring atom is an oxygen atom, by way of example and with preference oxetanyl, tetrahydrofuranyl and tetrahydro-2H-pyranyl.

In the formulae of the group which may represent $R^1$, the end point of the line marked by * in each case does not represent a carbon atom or a $CH_2$ group, but is part of the bond to the atom to which $R^1$ is attached.

In the formulae of the group which may represent $R^5$, the end point of the line marked by # in each case does not represent a carbon atom or a $CH_2$ group, but is part of the bond to the atom to which $R^5$ is attached.

Preference is given to compounds of the formula (I) in which
n represents the number 1 or 2,
A represents —N($R^2$)— or —$CH_2$—,
  wherein
  $R^2$ represents hydrogen or $C_1$-$C_4$-alkyl, $R^1$ represents a group of the formula

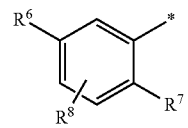

where * is the point of attachment to the oxopyridine ring,
$R^6$ represents bromine, chlorine, fluorine, methyl, difluoromethyl, trifluoromethyl, methoxy, difluoromethoxy or trifluoromethoxy,
$R^7$ represents hydrogen, bromine, chlorine, fluorine, cyano, nitro, hydroxy, methyl, difluoromethyl, trifluoromethyl, methoxy, difluoromethoxy, trifluoromethoxy, ethynyl, 3,3,3-trifluoroprop-1-yn-1-yl or cyclopropyl,
$R^8$ represents hydrogen, chlorine or fluorine,
$R^3$ represents hydrogen,
$R^4$ represents hydrogen,
$R^5$ represents a group of the formula

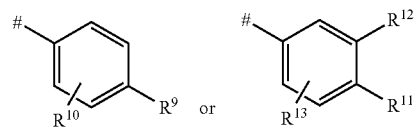

where # is the attachment site to the nitrogen atom,
$R^9$ represents hydroxycarbonyl or 5-membered heterocyclyl,
  where heterocyclyl may be substituted by 1 to 2 substituents independently of one another selected from the group consisting of oxo, hydroxy, methyl, difluoromethyl and trifluoromethyl,
    where methyl may be substituted by a methoxy substituent,
$R^{10}$ represents hydrogen, chlorine, fluorine or methyl,
$R^{11}$ and $R^{12}$ together with the carbon atoms to which they are bonded form a 5-membered heterocycle,
  where the heterocycle may be substituted by 1 to 2 substituents independently of one another selected from the group consisting of oxo, hydroxy, methyl, difluoromethyl, trifluoromethyl and 1,1,2,2,2-pentafluoroethyl,
$R^{13}$ represents hydrogen, chlorine, fluorine or methyl,
and the salts thereof, the solvates thereof and the solvates of the salts thereof.

Preference is also given to compounds of the formula (I) in which
n represents the number 1 or 2,
A represents —N($R^2$)— or —$CH_2$—,
  wherein
  $R^2$ represents hydrogen or methyl,
$R^1$ represents a group of the formula

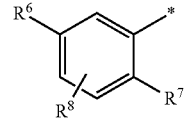

where * is the point of attachment to the oxopyridine ring,
$R^6$ represents chlorine,
$R^7$ represents hydrogen, bromine, chlorine, cyano, methyl, difluoromethyl, trifluoromethyl, difluoromethoxy or trifluoromethoxy,
$R^8$ represents hydrogen or fluorine, $R^3$ represents hydrogen,
$R^4$ represents hydrogen,
$R^5$ represents a group of the formula

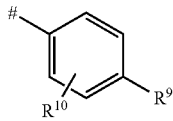

where # is the attachment site to the nitrogen atom,
$R^9$ represents hydroxycarbonyl, oxadiazolyl, pyrazolyl, imidazolyl, triazolyl or tetrazolyl,
where oxadiazolyl, pyrazolyl, imidazolyl and triazolyl may be substituted by 1 to 2 substituents independently of one another selected from the group consisting of oxo, hydroxy, methyl and trifluoromethyl,
$R^{10}$ represents hydrogen,
and the salts thereof, the solvates thereof and the solvates of the salts thereof.

Preference is also given to compounds of the formula (I) in which
n represents the number 1 or 2,
A represents —$CH_2$—,
$R^1$ represents a group of the formula

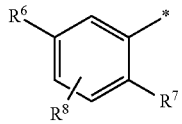

where * is the point of attachment to the oxopyridine ring,
$R^6$ represents chlorine.
$R^7$ represents bromine or cyano,
$R^8$ represents hydrogen,
$R^3$ represents hydrogen,
$R^4$ represents hydrogen,
$R^5$ represents a group of the formula

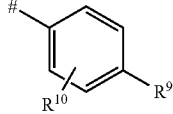

where # is the attachment site to the nitrogen atom,
$R^9$ represents hydroxycarbonyl, oxadiazolyl, pyrazolyl or tetrazolyl,
where oxadiazolyl and pyrazolyl may be substituted by 1 to 2 substituents independently of one another selected from the group consisting of oxo, hydroxy and trifluoromethyl,
$R^{10}$ represents hydrogen,
and the salts thereof, the solvates thereof and the solvates of the salts thereof.

Preference is also given to compounds of the formula (I) in which n represents the number 1.
Preference is also given to compounds of the formula (I) in which A represents —$CH_2$—.
Preference is also given to compounds of the formula (I) in which
$R^1$ represents a group of the formula

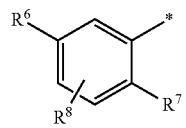

where * is the point of attachment to the oxopyridine ring,
$R^6$ represents chlorine,
$R^7$ represents bromine or cyano,
$R^8$ represents hydrogen.

Preference is also given to compounds of the formula (I) in which
$R^1$ represents a group of the formula

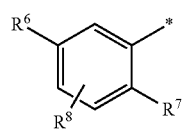

where * is the point of attachment to the oxopyridine ring,
$R^6$ represents chlorine.
$R^7$ represents cyano or difluoromethoxy,
$R^8$ represents hydrogen.

Preference is also given to compounds of the formula (I) in which $R^3$ represents hydrogen.

Preference is also given to compounds of the formula (I) in which
$R^5$ represents a group of the formula

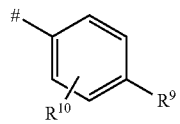

where # is the attachment site to the nitrogen atom,
$R^9$ represents hydroxycarbonyl, oxadiazolyl, pyrazolyl, imidazolyl, triazolyl or tetrazolyl,
where oxadiazolyl, pyrazolyl, imidazolyl and triazolyl may be substituted by 1 to 2 substituents independently of one another selected from the group consisting of oxo, hydroxy, methyl and trifluoromethyl,
$R^{10}$ represents hydrogen.

Preference is also given to compounds of the formula (I) in which
$R^5$ represents a group of the formula

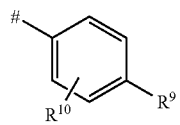

where # is the attachment site to the nitrogen atom,
$R^9$ represents hydroxycarbonyl, oxadiazolyl, pyrazolyl or tetrazolyl,
where oxadiazolyl and pyrazolyl may be substituted by 1 to 2 substituents independently of one another selected from the group consisting of oxo, hydroxy and trifluoromethyl,
$R^{10}$ represents hydrogen.

Irrespective of the particular combinations of the radicals specified, the individual radical definitions specified in the particular combinations or preferred combinations of radicals are also replaced as desired by radical definitions from other combinations.

Very particular preference is given to combinations of two or more of the abovementioned preferred ranges.

The invention further provides a process for preparing the compounds of the formula (I), or the salts thereof, solvates thereof or the solvates of the salts thereof, wherein

[A] the compounds of the formula

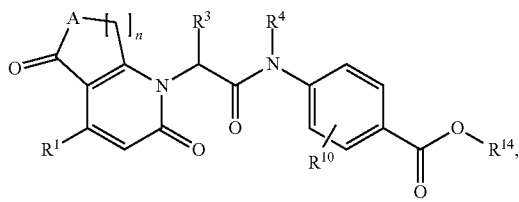
(IIa)

in which
n, A, $R^1$, $R^3$, $R^4$ and $R^{10}$ are each as defined above, and
$R^{14}$ represents tert-butyl,
are reacted with an acid to give compounds of the formula

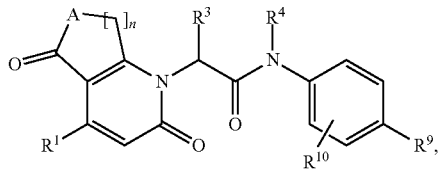
(Ib)

in which
n, A, $R^1$, $R^3$, $R^4$ and $R^{10}$ are each as defined above, and
$R^9$ represents hydroxycarbonyl,
or

[B] the compounds of the formula

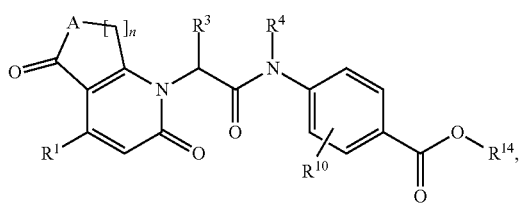
(IIb)

in which
n, A, $R^1$, $R^3$, $R^4$ and $R^{10}$ are each as defined above, and
$R^{14}$ represents methyl or ethyl,
are reacted with a base to give compounds of the formula

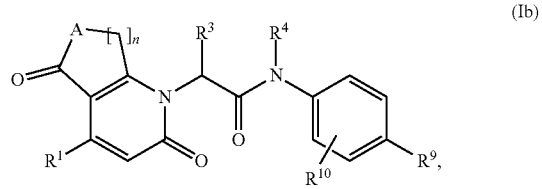
(Ib)

in which
n, A, $R^1$, $R^3$, $R^4$ and $R^{10}$ are each as defined above, and
$R^9$ represents hydroxycarbonyl,
or

[C] the compounds of the formula

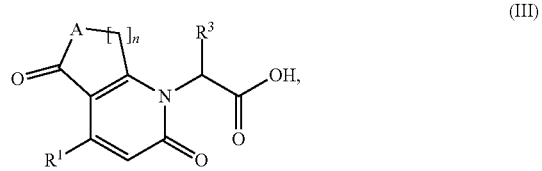
(III)

in which
n, A, $R^1$ and $R^3$ are each as defined above,
are reacted with compounds of the formula

(IV)

in which
$R^4$ and $R^5$ are each as defined above,
in the presence of a dehydrating agent to give compounds of the formula (I),
or

[D] the compounds of the formula

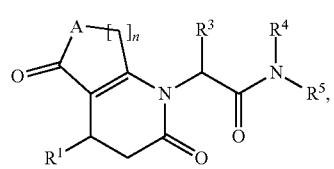
(V)

in which
n, A, $R^1$, $R^3$, $R^4$ and $R^5$ are each as defined above,
are reacted with oxidizing agents.

The compounds of the formula (Ib) are a subset of the compounds of the formula (I).

The compounds of the formulae (IIa) and (IIb) together form the group of the compounds of the formula (II).

The reaction according to process [A] is generally carried out in inert solvents, preferably in a temperature range from room temperature to 60° C. at atmospheric pressure.

Inert solvents are, for example, halogenated hydrocarbons such as dichloromethane, trichloromethane, carbon tetrachloride or 1,2-dichloroethane, or ethers such as tetrahydrofuran or dioxane, preference being given to dichloromethane.

Acids are, for example, trifluoroacetic acid or hydrogen chloride in dioxane, preference being given to trifluoroacetic acid.

The reaction according to process [B] is generally carried out in inert solvents, preferably in a temperature range from room temperature up to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvents with water, preference being given to a mixture of tetrahydrofuran and water.

Bases are, for example, alkali metal hydroxides such as sodium hydroxide, lithium hydroxide or potassium hydroxide, or alkali metal carbonates such as caesium carbonate, sodium carbonate or potassium carbonate, or alkoxides such as potassium tert-butoxide or sodium tert-butoxide, preference being given to lithium hydroxide.

The reaction according to process [C] is generally carried out in inert solvents, if appropriate in the presence of a base, preferably in a temperature range from 0° C. to room temperature at atmospheric pressure.

Suitable dehydrating agents here are, for example, carbodiimides such as N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), (benzotriazol-1-yloxy)bisdimethyl-aminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl hydroxyiminocyanoacetate/N,N'-diisopropylcarbodiimide or mixtures of these, preference being given to HATU.

Bases are, for example, alkali metal carbonates such as sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine; preference is given to diisopropylethylamine.

Inert solvents are, for example, halogenated hydrocarbons such as dichloromethane or trichloromethane, hydrocarbons such as benzene, or other solvents such as nitromethane, dioxane, dimethylformamide, dimethyl sulphoxide or acetonitrile. It is also possible to use mixtures of the solvents, preference being given to dimethylformamide.

The reaction according to process [D] is generally carried out in inert solvents, preferably in a temperature range from room temperature to 60° C. at atmospheric pressure.

Inert solvents are, for example, halohydrocarbons such as dichloromethane, trichloromethane, carbon tetrachloride or 1,2-dichloroethane, or ethers such as tetrahydrofuran or dioxane, or mixtures of solvents, or mixtures of solvents with water, preference being given to a mixture of dioxane and water.

Oxidizing agents are, for example, ammonium cerium (IV) nitrate, 4,5-dichloro-3,6-dioxocyclohexa-1,4-diene-1,2-dicarbonitrile (DDQ), manganese(IV) oxide, potassium permanganate, bromine, N-bromosuccinimide/dibenzoyl peroxide, preference being given to ammonium cerium(IV) nitrate.

The compounds of the formula (IV) are known, can be synthesized from the corresponding starting compounds by known processes or can be prepared analogously to the processes described in the Examples section.

The compounds of the formula (II) are known or can be prepared by reacting compounds of the formula

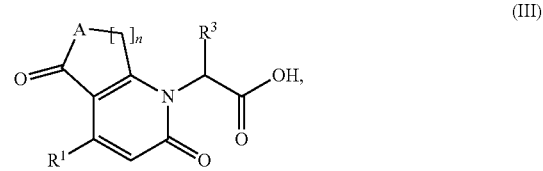

(III)

in which
n, A, $R^1$ and $R^3$ are each as defined above,
with compounds of the formula

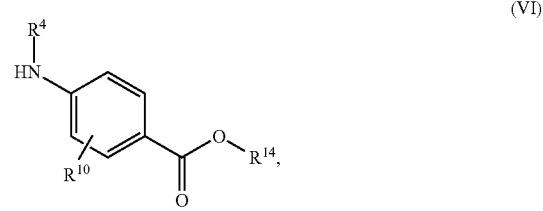

(VI)

in which
$R^4$ and $R^{10}$ are each as defined above, and
$R^{14}$ represents methyl, ethyl or tert-butyl,
in the presence of a dehydrating reagent.

The reaction is carried out as described for process [C].

The compounds of the formula (VI) are known, can be synthesized from the corresponding starting compounds by known processes or can be prepared analogously to the processes described in the Examples section.

The compounds of the formula (III) are known or can be prepared by
[E] reacting compounds of the formula

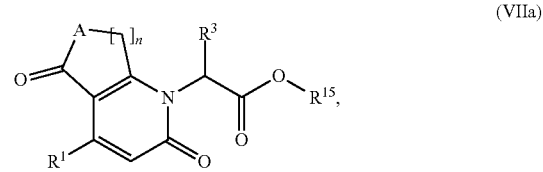

(VIIa)

in which
n, A, R¹ and R³ are each as defined above, and
R¹⁵ represents tert-butyl,
with an acid,
or
[F] reacting compounds of the formula

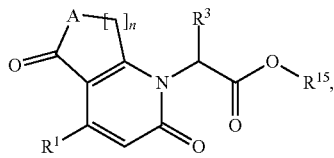
(VIIb)

in which
n, A, R¹ and R³ are each as defined above, and
R¹⁵ represents methyl or ethyl,
with a base.

The compounds of the formulae (VIIa) and (VIIb) together form the group of the compounds of the formula (VII).

The reaction according to process [E] is carried out as described for process [A].

The reaction in process [F] is effected as described for process [B].

The compounds of the formula (VII) are known or can be prepared by
[G] reacting compounds of the formula

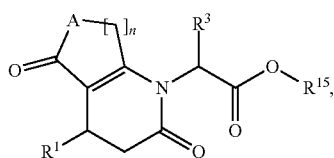
(VIII)

in which
n, A, R¹ and R³ are each as defined above, and
R¹⁵ represents methyl, ethyl or tert-butyl,
with oxidizing agents,
or
[H] reacting compounds of the formula

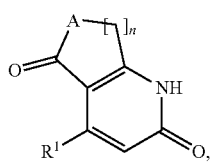
(IX)

in which
n, A and R¹ are each as defined above,
with compounds of the formula

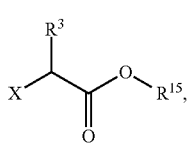
(X)

in which
R³ has the meaning given above,
R¹⁵ represents methyl, ethyl or tert-butyl, and
X¹ represents chlorine, bromine, iodine, methanesulphonyloxy or trifluoromethanesulphonyloxy,
or
[I] reacting compounds of the formula

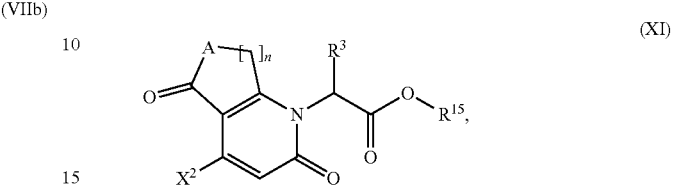
(XI)

in which
n, A, and R³ are each as defined above,
R¹⁵ represents methyl, ethyl or tert-butyl, and
X represents (trifluoromethyl)sulphonyloxy,
with compounds of the formula

R¹-Q    (XII), in which
R¹ is as defined above, and
Q represents —B(OH)₂, a boronic ester, preferably boronic acid pinacol ester, or —BF₃—K⁺,
under Suzuki coupling conditions.

The reaction in process [G] is effected as described for process [D].

The reaction according to process [H] is generally carried out in inert solvents, optionally in the presence of a base, preferably in a temperature range from room temperature to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvents with water; preference is given to dimethylformamide Bases are, for example, alkali metal hydroxides such as sodium hydroxide, lithium hydroxide or potassium hydroxide, or alkali metal carbonates such as caesium carbonate, sodium carbonate or potassium carbonate, or potassium tert-butoxide or sodium tert-butoxide, sodium hydride or a mixture of these bases or a mixture of sodium hydride and lithium bromide, preference being given to potassium carbonate or sodium hydride or a mixture of sodium hydride and lithium bromide.

The reaction in process [I] is generally effected in inert solvents, in the presence of a catalyst, optionally in the presence of an additional reagent, optionally in a microwave, preferably within a temperature range from room temperature to 150° C. at standard pressure to 3 bar.

Catalysts are, for example, palladium catalysts customary for Suzuki reaction conditions, preference being given to catalysts such as dichlorobis(triphenylphosphine)palladium, tetrakistriphenylphosphinepalladium(0), palladium(II) acetate/tricyclohexylphosphine, tris(dibenzylideneacetone) dipalladium, bis(diphenylphosphaneferrocenyl)palladium (II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene) palladium, palladium(II) acetate/dicyclohexyl(2',4',6'-triisopropyl-biphenyl-2-yl)phosphine, [1,1-bis(diphenylphosphino)ferrocene]palladium(II) chloride monodichloromethane adduct or XPhos precatalyst [(2'- aminobiphenyl-2-yl)(chloro)palladium dicyclohexyl(2',4',6'-triisopropylbiphenyl-2-yl)phosphane (1:1)], preference being given to tetrakistriphenylphosphinepalladium(0), [1,1-bis-(diphenylphosphino)ferrocene]palladium(II) chloride monodichloromethane adduct or XPhos precatalyst [(2'-aminobiphenyl-2-yl)(chloro)palladium dicyclohexyl(2',4',6'-triisopropylbiphenyl-2-yl)phosphine (1:1)].

Additional reagents are, for example, potassium acetate, caesium carbonate, potassium carbonate or sodium carbonate, potassium tert-butoxide, caesium fluoride or potassium phosphate, where these may be present in aqueous solution; preferred are additional reagents such as potassium carbonate or aqueous potassium phosphate solution.

Inert solvents are, for example, ethers such as dioxane, tetrahydrofuran or 1,2-dimethoxyethane, hydrocarbons such as benzene, xylene or toluene, or carboxamides such as dimethylformamide or dimethylacetamide, alkyl sulphoxides such as dimethyl sulphoxide, order N-methylpyrrolidone or acetonitrile, or mixtures of the solvents with alcohols such as methanol or ethanol and/or water; preference is given to tetrahydrofuran, dioxane or acetonitrile.

The compounds of the formulae (X) and (XII) are known or can be synthesized by known processes from the appropriate starting compounds.

The compounds of the formula (VIII) are known or can be prepared by
[J] reacting compounds of the formula

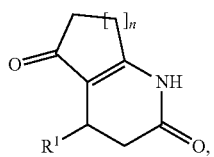 (XIII)

in which
n, and $R^1$ are each as defined above,
with compounds of the formula (X) to give compounds of the formula

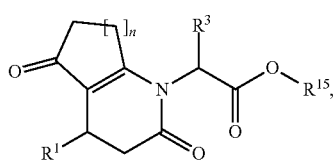 (VIIIa)

in which
n, $R^1$ and $R^3$ are each as defined above, and
$R^{15}$ represents methyl, ethyl or tert-butyl,
or
[K] reacting compounds of the formula

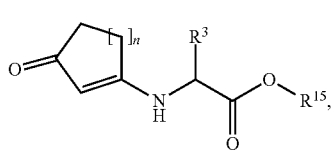 (XIV)

in which
n and $R^3$ are each as defined above, and
$R^{15}$ represents methyl, ethyl or tert-butyl, with compounds of the formula

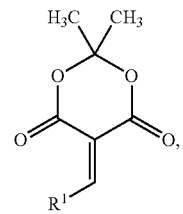 (XV)

in which
$R^1$ has the meaning given above,
to give compounds of the formula

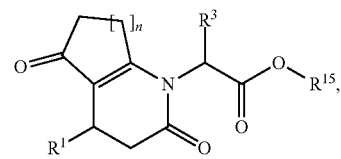 (VIIIa)

in which
N, $R^1$ and $R^3$ are each as defined above, and
$R^{15}$ represents methyl, ethyl or tert-butyl,
or
[L] reacting compounds of the formula

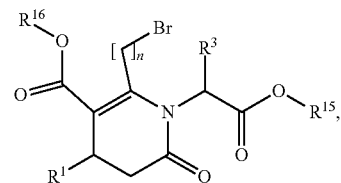 (XVI)

in which
n, $R^1$ and $R^3$ are each as defined above,
$R^{15}$ represents methyl, ethyl or tert-butyl, and
$R^{16}$ represents methyl or ethyl,
with compounds of the formula $$R^2-NH_2 \quad (XVII),$$

in which
$R^2$ has the meaning given above,
to give compounds of the formula (VIIIb)

in which
n, $R^1$, $R^2$ and $R^3$ are each as defined above, and
$R^{15}$ represents methyl, ethyl or tert-butyl.

The compounds of the formulae (VIIIa) and (VIIIb) together form the group of the compounds of the formula (VIII).

The reaction according to process [J] is carried out as described for process [H].

The reaction in process [K] is generally effected in inert solvents, preferably within a temperature range from room temperature up to the reflux of the solvents, preferably in a temperature range from 60° C. to 80° C., at standard pressure.

Inert solvents are, for example, ethers such as dioxane or tetrahydrofuran, or alcohols such as ethanol, preference being given to ethanol.

The reaction according to process [L] is generally carried out in inert solvents, preferably in a temperature range from room temperature to 120° C., preferably room temperature to 80° C., at atmospheric pressure.

Inert solvents are, for example, ethers such as dioxane or tetrahydrofuran, or acetonitrile, or alcohols such as methanol or ethanol, preference being given to tetrahydrofuran or acetonitrile.

The compounds of the formulae (XIV), (XV), (XVI) and (XVII) are known, can be synthesized from the corresponding starting compounds by known processes or can be prepared analogously to the processes described in the Examples section.

The compounds of the formula (XIII) are known or can be prepared by reacting compounds of the formula

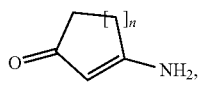
(XVIII)

in which
n is as defined above,
with compounds of the formula (XV) in the first stage,
and optionally reacting with a dehydrating reagent in a second stage.

The reaction of the first stage is generally effected in inert solvents, preferably within a temperature range from room temperature up to the reflux of the solvents, preferably at the reflux of the solvents, at standard pressure.

Inert solvents are, for example ethers such as dioxane or tetrahydrofuran, or alcohols such as ethanol, preference being given to dioxane.

The reaction of the second stage is carried out as described for process [C].

The compounds of the formula (XVIII) are known, can be synthesized from the corresponding starting compounds by known processes or can be prepared analogously to the processes described in the Examples section.

The compounds of the formula (V) are known or can be prepared by reacting compounds of the formula

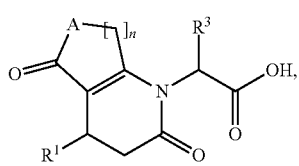
(XIX)

in which
n, A, $R^1$ and $R^3$ are each as defined above,
with compounds of the formula (IV) in the presence of a dehydrating reagent.

The reaction is carried out as described for process [C].

The compounds of the formula (XIX) are known or can be prepared by

[M] reacting compounds of the formula

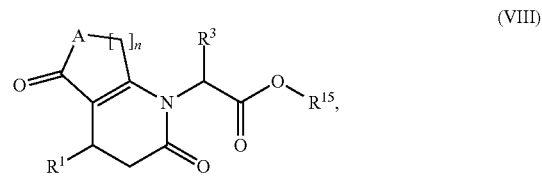
(VIII)

in which
n, A, $R^1$ and $R^3$ are each as defined above, and
$R^{15}$ represents tert-butyl,
with an acid,
or

[N] reacting compounds of the formula

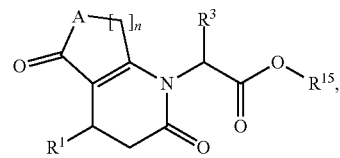
(VIII)

in which
n, A, $R^1$ and $R^3$ are each as defined above, and
$R^{15}$ represents methyl or ethyl,
with a base.

The reaction in process [M] is effected as described for process [A].

The reaction in process [N] is effected as described for process [B].

The compounds of the formula (IX) are known or can be prepared by reacting compounds of the formula

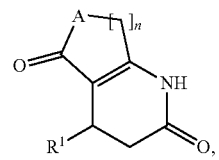
(XX)

in which
n, A, and $R^1$ are each as defined above,
with oxidizing agents.

The reaction is carried out as described for process [D].

The compounds of the formula (XX) are known, can be synthesized from the corresponding starting compounds by known processes or can be prepared analogously to the processes described in the Examples section.

The compounds of the formula (XI) are known or can be prepared by reacting compounds of the formula

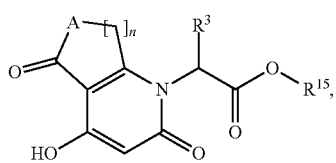

in which n, A and R³ are each as defined above, and
R¹⁵ represents methyl, ethyl or tert-butyl,
with trifluoromethanesulphonic anhydride or N,N-bis(trifluoromethanesulphonyl)aniline The reaction is generally carried out in inert solvents, in the presence of a base, preferably in a temperature range from −78° C. to room temperature, preferably 0° C., at atmospheric pressure.

Inert solvents are, for example, dichloromethane, chloroform, tetrahydrofuran or dimethylformamide, preference being given to dichloromethane.

Bases are, for example, pyridine, 2,6-dimethylpyridine, triethylamine, diisopropylethylamine, preference being given to 2,6-dimethylpyridine or triethylamine Particular preference is given to the reaction with trifluoromethanesulphonic anhydride in the presence of 2,6-dimethylpyridine or N,N-bis(trifluoromethanesulphonyl)aniline in the presence of triethylamine.

The compounds of the formula (XXI) are known, can be synthesized from the corresponding starting compounds by known processes or can be prepared analogously to the processes described in the Examples section.

The preparation of the starting compounds and of the compounds of the formula (I) can be illustrated by the synthesis schemes which follow.

Scheme 1:

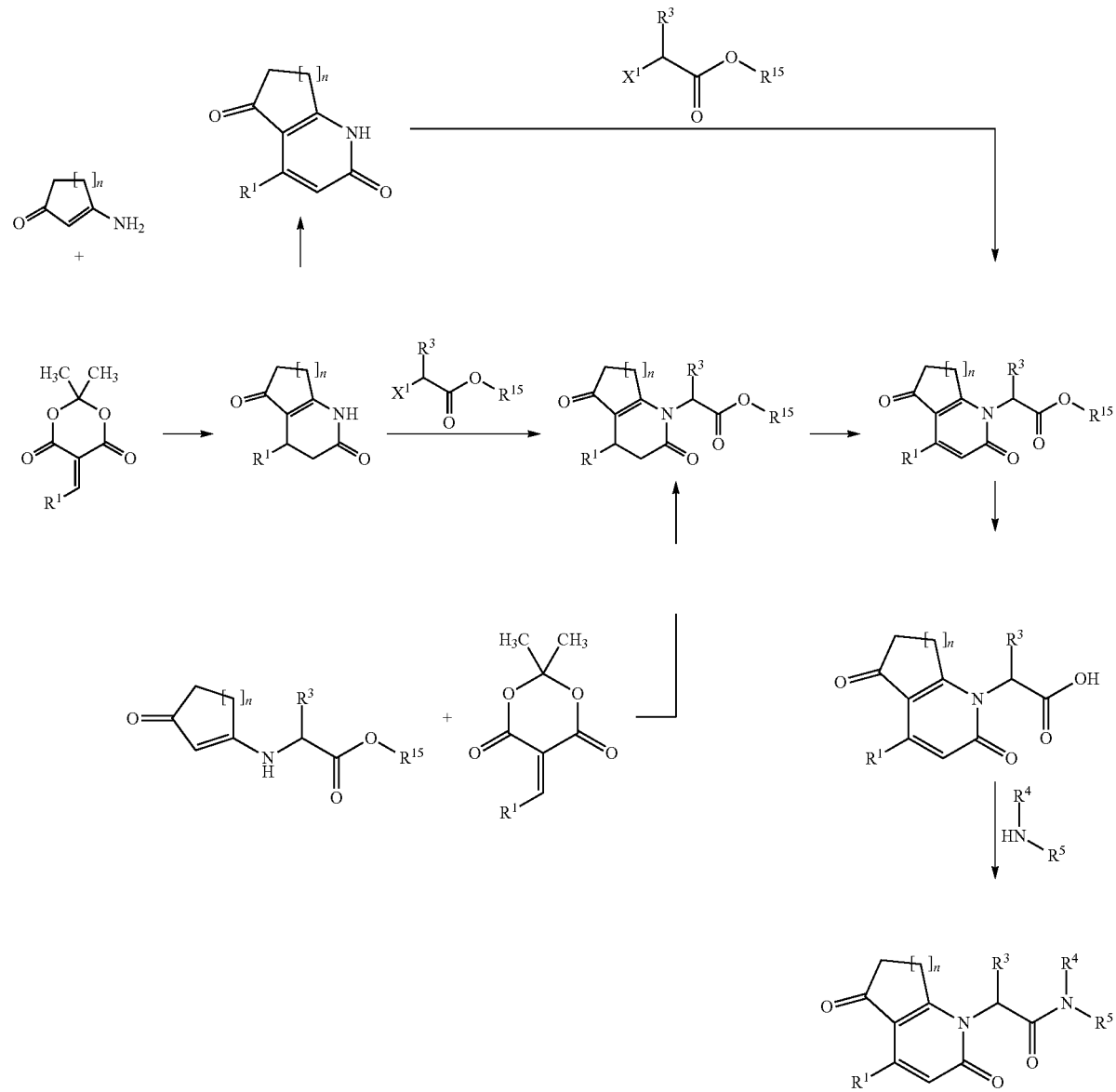

Scheme 2:
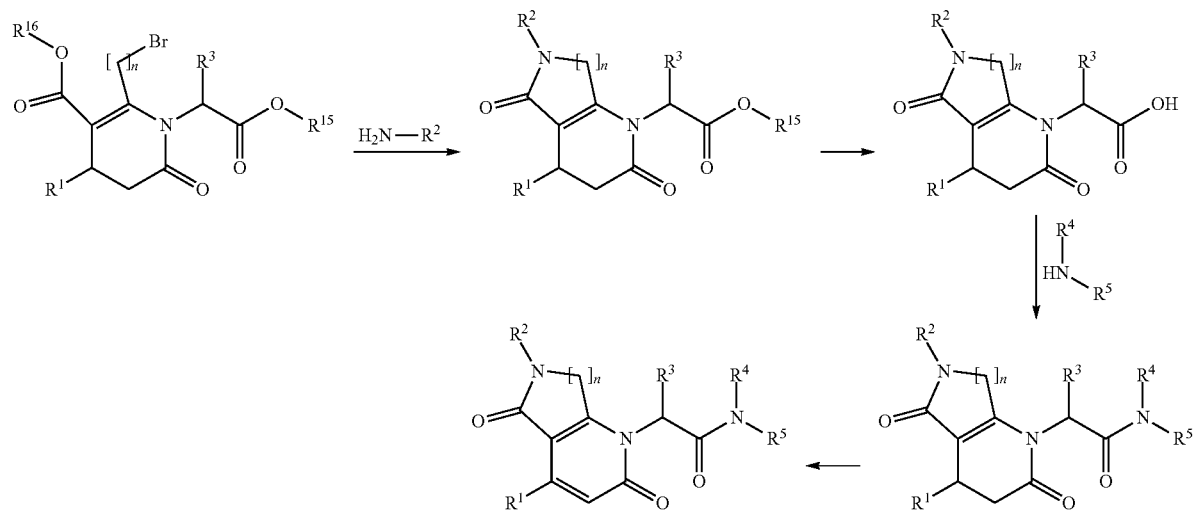
Scheme 3:
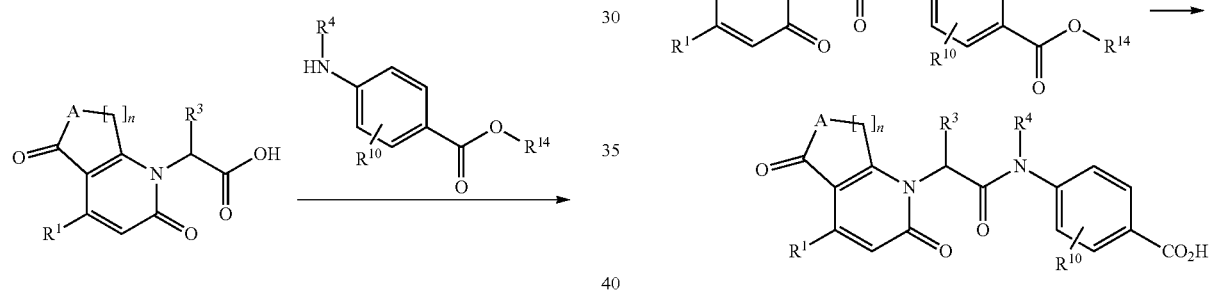
Scheme 4:
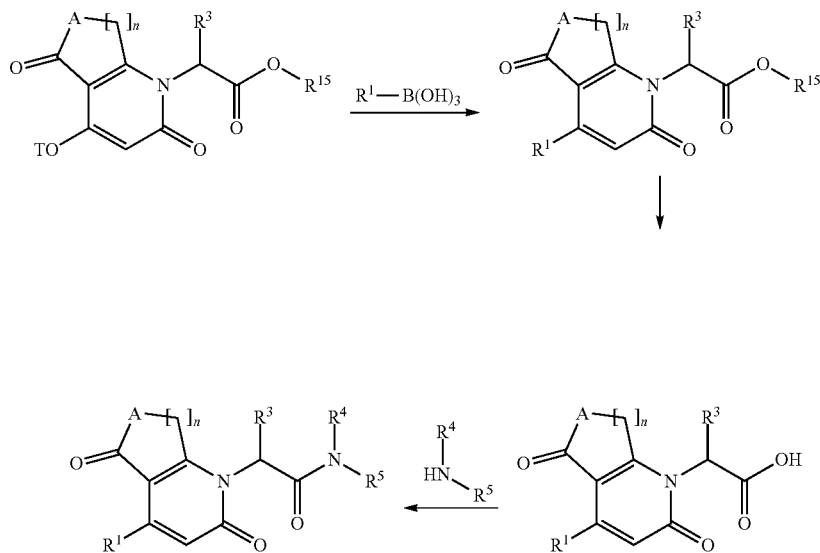

The compounds according to the invention have an unforeseeable useful pharmacological activity spectrum and good pharmacokinetic behaviour. They are compounds that influence the proteolytic activity of the serine protease factor XIa (FXIa) and/or the serine protease plasma kallikrein (PK). The compounds according to the invention inhibit the enzymatic cleavage of substrates, catalysed by FXIa and/or PK, which have essential roles in the activation of blood coagulation, in the aggregation of blood platelets via reduction of the thrombin necessary for the PAR-1 activation of the platelets, and in inflammatory processes, which particularly involve an increase in vascular permeability.

They are therefore suitable for use as medicaments for the treatment and/or prophylaxis of diseases in humans and animals.

The present invention further provides for the use of the compounds according to the invention for the treatment and/or prophylaxis of disorders, in particular cardiovascular disorders, preferably thrombotic or thromboembolic disorders and/or thrombotic or thromboembolic complications, and/or ophthalmic disorders, in particular of diabetic retinopathy or macular oedema, and/or inflammatory disorders, in particular those associated with excess plasma kallikrein activity, such as hereditary angiooedema (HAE) or chronic inflammatory disorders, particularly of the intestine such as Crohn's disease.

Factor XIa (FXIa) is an important enzyme in the context of coagulation, which can be activated both by thrombin and factor XIIa (FXIIa), and is therefore involved in two essential processes of coagulation. It is a central component of the transition from initiation to amplification and propagation of coagulation: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated leading to strong thrombus growth and stabilizing the thrombus.

Moreover, factor XIa is an important component for the intrinsic initiation of coagulation: In addition to the stimulation via tissue factor (TF), the coagulation system can be activated also particularly on negatively charged surfaces, which include not only surface structures of foreign cells (e.g. bacteria) but also artificial surfaces such as vascular prostheses, stents and extracoporeal circulation. On the surface, initially factor XII (FXII) is activated to factor XIIa (FXIIA) which subsequently activates FXI, attached to cell surfaces, to FXIa. This leads to further activation of the coagulation cascade as described above.

In contrast, thrombin generation in the initiation phase remains uninfluenced via TF/factor VIIa and factor X activation and finally thrombin formation, the physiological reaction on vascular injuries, remains uninfluenced. This could explain why no prolongations of bleeding times were found in FXIa knockout mice, as in rabbits and other species, with administration of FXIa. This low bleeding tendency caused by the substance is of great advantage for use in humans, particularly in patients with increased risk of bleeding.

In addition, factor XIIa also activates plasma prokallikrein to plasma kallikrein (PK) in the context of the intrinsic activation which, inter alia, in a potentiation loop, leads to further factor XII activation, overall resulting in amplification of the initiation of the coagulation cascade on surfaces. A PK-inhibiting activity of a compound according to the invention thus reduces coagulation via surface activation and thus has an anticoagulatory effect. An advantage could be in the combination of factor XIa inhibitory activity and PK inhibitory activity allowing a balanced antithrombotic effect.

Accordingly, the compounds according to the invention are suitable for the treatment and/or prophylaxis of disorders or complications which may arise from the formation of clots.

For the purpose of the present invention, the "thrombotic or thromboembolic disorders" include disorders which occur both in the arterial and in the venous vasculature and which can be treated with the compounds according to the invention, in particular disorders in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass, but also thrombotic or thromboembolic disorders in further vessels leading to peripheral arterial occlusive disorders, pulmonary embolisms, venous thromboembolisms, venous thromboses, in particular in deep leg veins and kidney veins, transitory ischemic attacks and also thrombotic stroke and thromboembolic stroke.

Stimulation of the coagulation system may occur by various causes or associated disorders. In the context of surgical interventions, immobility, confinement to bed, infections, inflammation or cancer or cancer therapy, inter alia, the coagulation system can be highly activated, and there may be thrombotic complications, in particular venous thromboses. The compounds according to the invention are therefore suitable for the prophylaxis of thromboses in the context of surgical interventions in patients suffering from cancer. The compounds according to the invention are therefore also suitable for the prophylaxis of thromboses in patients having an activated coagulation system, for example in the stimulation situations described.

The inventive compounds are therefore also suitable for the prevention and treatment of cardiogenic thromboembolisms, for example brain ischemias, stroke and systemic thromboembolisms and ischemias, in patients with acute, intermittent or persistent cardial arrhythmias, for example atrial fibrillation, and in patients undergoing cardioversion, and also in patients with heart valve disorders or with artificial heart valves.

In addition, the inventive compounds are suitable for the treatment and prevention of disseminated intravascular coagulation (DIC) which may occur in connection with sepsis inter alia, but also owing to surgical interventions, neoplastic disorders, burns or other injuries and may lead to severe organ damage through microthrombosis.

Thromboembolic complications furthermore occur in microangiopathic hemolytical anaemias and by the blood coming into contact with foreign surfaces in the context of extracorporeal circulation such as, for example, hemodialysis, ECMO ("extracorporeal membrane oxygenation"), LVAD ("left ventricular assist device") and similar methods, AV fistulas, vascular and heart valve prostheses.

Moreover, the compounds according to the invention are suitable for the treatment and/or prophylaxis of disorders involving microclot formation or fibrin deposits in cerebral blood vessels which may lead to dementia disorders such as vascular dementia or Alzheimer's disease. Here, the clot may contribute to the disorder both via occlusions and by binding further disease-relevant factors.

Moreover, the compounds according to the invention are suitable in particular for the treatment and/or prophylaxis of disorders where, in addition to the pro-coagulant component, the pro-inflammatory component plays an essential role. Mutual enhancement of coagulation and inflammation in particular can be prevented by the compounds according to the invention, thus decisively lowering the probability of thrombotic complications. In this case, both the factor XIa-inhibitory component (via inhibition of thrombin production) and the PK-inhibitory component can contribute to the anticoagulant and antiinflammatory effect (e.g. via bradykinin). Therefore, the treatment and/or prophylaxis in the context of atherosclerotic vascular disorders, inflammations in the context of rheumatic disorders of the locomotor system, inflammatory disorders of the lung, such as pulmonary fibroses, inflammatory disorders of the kidney, such as glomerulonephritides, inflammatory disorders of the intestine, such as Crohn's disease or ulcerative colitis, or disorders which may be present in the context of a diabetic underlying disease, such as diabetic retinopathy or nephropathy, may be considered, inter alia.

Kinins generated by means of plasma kallikrein, inter alia, have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Moreover, the compounds according to the invention can be used for inhibiting tumour growth and the formation of metastases, and also for the prophylaxis and/or treatment of thromboembolic complications, such as, for example, venous thromboembolisms, for tumour patients, in particular those undergoing major surgical interventions or chemo- or radiotherapy.

In addition, the inventive compounds are also suitable for the prophylaxis and/or treatment of pulmonary hypertension.

In the context of the present invention, the term "pulmonary hypertension" includes pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

"Pulmonary arterial hypertension" includes idiopathic pulmonary arterial hypertension (IPAH, formerly also referred to as primary pulmonary hypertension), familial pulmonary arterial hypertension (FPAH) and associated pulmonary-arterial hypertension (APAH), which is associated with collagenoses, congenital systemic-pulmonary shunt vitia, portal hypertension, HIV infections, the ingestion of certain drugs and medicaments, with other disorders (thyroid disorders, glycogen storage disorders, Morbus Gaucher, hereditary teleangiectasia, hemoglobinopathies, myeloproliferative disorders, splenectomy), with disorders having a significant venous/capillary contribution, such as pulmonary-venoocclusive disorder and pulmonary-capillary hemangiomatosis, and also persisting pulmonary hypertension of neonatants.

Pulmonary hypertension associated with disorders of the left heart includes a diseased left atrium or ventricle and mitral or aorta valve defects.

Pulmonary hypertension associated with pulmonary disorders and/or hypoxia includes chronic obstructive pulmonary disorders, interstitial pulmonary disorder, sleep apnoea syndrome, alveolar hypoventilation, chronic high-altitude sickness and inherent defects.

Pulmonary hypertension owing to chronic thromboembolisms (CTEPH) comprises the thromboembolic occlusion of proximal pulmonary arteries, the thromboembolic occlusion of distal pulmonary arteries and non-thrombotic pulmonary embolisms (tumour, parasites, foreign bodies).

The present invention further provides for the use of the inventive compounds for production of medicaments for the treatment and/or prophylaxis of pulmonary hypertension associated with sarcoidosis, histiocytosis X and lymphangiomatosis.

In addition, the inventive substances may also be useful for the treatment of pulmonary and hepatic fibroses.

In addition, the inventive compounds may also be suitable for treatment and/or prophylaxis of disseminated intravascular coagulation in the context of an infectious disease, and/or of systemic inflammatory syndrome (SIRS), septic organ dysfunction, septic organ failure and multiorgan failure, acute respiratory distress syndrome (ARDS), acute lung injury (ALI), septic shock and/or septic organ failure.

In the course of an infection, there may be a generalized activation of the coagulation system (disseminated intravascular coagulation or consumption coagulopathy, hereinbelow referred to as "DIC") with microthrombosis in various organs and secondary hemorrhagic complications. Moreover, there may be endothelial damage with increased permeability of the vessels and seeping of fluids and proteins into the extravasal lumen. As the infection progresses, there may be failure of an organ (for example kidney failure, liver failure, respiratory failure, central-nervous deficits and cardiovascular failure) or multiorgan failure.

In the case of DIC, there is a massive activation of the coagulation system at the surface of damaged endothelial cells, the surfaces of foreign bodies or injured extravascular tissue. As a consequence, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding.

Compounds according to the invention which inhibit plasma kallikrein alone or in combination with factor XIa, are also useful for the treatment and/or prophylaxis of disorders in the course of which plasma kallikrein is involved. In addition to the anticoagulant activity, plasma kallikrein is an important bradikinin-releasing protease which, inter alia, thus leads to increased endothelial permeability. The compounds can therefore be used for the treatment and/or prophylaxis of disorders involving oedema formations such as ophthalmic disorders, in particular, diabetic retinopathy or macular oedema or hereditary angiooedema.

"Ophthalmic disorders" in the context of the present invention include in particular disorders such as diabetic retinopathy, diabetic macular oedema (DME), macular oedema, macular oedema associated with retinal vein occlusion, age-related macular degeneration (AMD), choroidal neovascularization (CNV), choroidal neovascular membranes (CNVM), cystoid macula oedema (CME), epiretinal membranes (ERM) and macula perforations, myopia-associated choroidal neovascularization, angioid streaks, vascular streaks, retina detachment, atrophic changes of the retinal pigment epithelium, hypertrophic changes of the retinal pigment epithelium, retinal vein occlusion, choroidal retinal vein occlusion, retinitis pigmentosa, Stargardt's disease, retinopathy of prematurity, glaucoma, inflammatory eye disorder such as uveitis, scleritis or endophthalmitis, cataract, refraction anomalies such as myopia, hyperopia or astigmatism and keratoconus, disorders of the anterior eye such as corneal angiogenesis as sequela of, for example *ceratitis*, cornea transplantation or keratoplasty, conical angiogenesis as sequela of hypoxia (for example by excessive use of contact lenses), pterygium conjunctivae, subcorneal oedema and intracorneal oedema.

The compounds according to the invention are also suitable for the primary prophylaxis of thrombotic or thromboembolic disorders and/or inflammatory disorders and/or disorders with increased vascular permeability in patients in which gene mutations lead to enhanced activity of the enzymes, or increased levels of the zymogens and these are established by relevant tests/measurements of the enzyme activity or zymogen concentrations.

The present invention further provides for the use of the compounds according to the invention for the treatment and/or prophylaxis of disorders, especially the disorders mentioned above.

The present invention further provides for the use of the compounds according to the invention for production of a medicament for the treatment and/or prophylaxis of disorders, especially the disorders mentioned above.

The present invention further provides a method for the treatment and/or prophylaxis of disorders, especially the disorders mentioned above, using a therapeutically effective amount of a compound according to the invention.

The present invention further provides the compounds according to the invention for use in a method for the treatment and/or prophylaxis of disorders, especially the disorders mentioned above, using a therapeutically effective amount of a compound according to the invention.

The present invention further provides medicaments comprising a compound according to the invention and one or more further active compounds.

In addition, the compounds according to the invention can also be used for preventing coagulation ex vivo, for example for the protection of organs to be transplanted against organ damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo or for biological samples which may comprise factor XIa or plasma kallikrein.

The present invention furthermore provides a method for preventing the coagulation of blood in vitro, in particular in banked blood or biological samples which may comprise factor XIa or plasma kallikrein or both enzymes, which method is characterized in that an anticoagulatory effective amount of the compound according to the invention is added.

The present invention further provides medicaments comprising a compound according to the invention and one or more further active compounds, in particular for the treatment and/or prophylaxis of the disorders mentioned above. Preferred examples of active compounds suitable for combinations include:

lipid-lowering substances, especially HMG-CoA (3-hydroxy-3-methylglutaryl-coenzyme A) reductase inhibitors, for example lovastatin (Mevacor), simvastatin (Zocor), pravastatin (Pravachol), fluvastatin (Lescol) and atorvastatin (Lipitor);

coronary therapeutics/vasodilators, especially ACE (angiotensin converting enzyme) inhibitors, for example captopril, lisinopril, enalapril, ramipril, cilazapril, benazepril, fosinopril, quinapril and perindopril, or AII (angiotensin II) receptor antagonists, for example embusartan, losartan, valsartan, irbesartan, candesartan, eprosartan and temisartan, or β-adrenoceptor antagonists, for example carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists, for example prazosine, bunazosine, doxazosine and terazosine, or diuretics, for example hydrochlorothiazide, furosemide, bumetanide, piretanide, torasemide, amiloride and dihydralazine, or calcium channel blockers, for example verapamil and diltiazem, or dihydropyridine derivatives, for example nifedipin (Adalat) and nitrendipine (Bayotensin), or nitro preparations, for example isosorbide 5-mononitrate, isosorbide dinitrate and glycerol trinitrate, or substances causing an increase in cyclic guanosine monophosphate (cGMP), for example stimulators of soluble guanylate cyclase, for example riociguat;

plasminogen activators (thrombolytics/fibrinolytics) and compounds which promote thrombolysis/fibrinolysis such as inhibitors of the plasminogen activator inhibitor (PAI inhibitors) or inhibitors of the thrombin-activated fibrinolysis inhibitor (TAFI inhibitors) such as, for example, tissue plasminogen activator (t-PA, for example Actilyse®), streptokinase, reteplase and urokinase or plasminogen-modulating substances causing increased formation of plasmin;

anticoagulatory substances (anticoagulants), for example heparin (UFH), low-molecular-weight heparins (LMW), for example tinzaparin, certoparin, parnaparin, nadroparin, ardeparin, enoxaparin, reviparin, dalteparin, danaparoid, semuloparin (AVE 5026), adomiparin (M118) and EP-42675/ORG42675;

direct thrombin inhibitors (DTI) such as, for example, Pradaxa (dabigatran), atecegatran (AZD-0837), DP-4088, SSR-182289A, argatroban, bivalirudin and tanogitran (BIBT-986 and prodrug BIBT-1011), hirudin;

direct factor Xa inhibitors, for example, rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, tanogitran (BIBT-986, prodrug: BIBT-1011), idraparinux and fondaparinux, substances which inhibit the aggregation of platelets (platelet aggregation inhibitors, thrombocyte aggregation inhibitors), such as, for example, acetylsalicylic acid (such as, for example, aspirin), P2Y12 antagonists such as, for example, ticlopidine (Ticlid), clopidogrel (Plavix), prasugrel, ticagrelor, cangrelor, elinogrel, PAR-1 antagonists such as, for example, vorapaxar, PAR-4 antagonists, EP3 antagonists such as, for example, DG041;

platelet adhesion inhibitors such as GPVI and/or GPIb antagonists such as, for example, Revacept or caplacizumab;

fibrinogen receptor antagonists (glycoprotein-IIb/IIIa antagonists), for example abciximab, eptifibatide, tirofiban, lamifiban, lefradafiban and fradafiban;

recombinant human activated protein C such as, for example, Xigris or recombinant thrombomudulin;

and also antiarrhythmics;

inhibitors of VEGF and/or PDGF signal paths such as, for example, aflibercept, ranibizumab, bevacizumab, KH-902, pegaptanib, ramucirumab, squalamin or bevasiranib, apatinib, axitinib, brivanib, cediranib, dovitinib, lenvatinib, linifanib, motesanib, pazopanib, regorafenib, sorafenib, sunitinib, tivozanib, vandetanib, vatalanib, Vargatef and E-10030;

inhibitors of angiopoietin-Tie signal paths such as, for example, AMG386;

inhibitors of Tie2 receptor tyrosine kinase;

inhibitors of the integrin signal paths such as, for example, volociximab, cilengitide and ALG1001;

inhibitors of the PI3K-Akt-mTor signal paths such as, for example, XL-147, perifosine, MK2206, sirolimus, temsirolimus and everolimus;

corticosteroids such as, for example, anecortave, betamethasone, dexamethasone, triamcinolone, fluocinolone and fluocinolone acetonide;

inhibitors of the ALK1-Smad1/5 signal path such as, for example, ACE041;

cyclooxygenase inhibitors such as, for example, bromfenac and nepafenac;

inhibitors of the kallikrein-kinin system such as, for example, safotibant and ecallantide;

inhibitors of the sphingosine 1-phosphate signal paths such as, for example, sonepcizumab;

inhibitors of the complement-C5a receptor such as, for example, eculizumab;

inhibitors of the 5HT1a receptor such as, for example, tandospirone;

inhibitors of the Ras-Raf-Mek-Erk signal path; inhibitors of the MAPK signal paths; inhibitors of the FGF signal paths; inhibitors of endothelial cell proliferation; apoptosis-inducing active compounds;

photodynamic therapy consisting of an active compound and the action of light, the active compound being, for example, verteporfin.

"Combinations" for the purpose of the invention mean not only dosage forms which contain all the components (so-called fixed combinations) and combination packs which contain the components separate from one another, but also components which are administered simultaneously or sequentially, provided that they are used for prophylaxis and/or treatment of the same disease. It is likewise possible to combine two or more active ingredients with one another, meaning that they are thus each in two-component or multicomponent combinations.

The inventive compounds can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The inventive compounds can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

Suitable for extraocular (topic) administration are administration forms which operate in accordance with the prior art, which release the active compound rapidly and/or in a modified or controlled manner and which contain the active compound in crystalline and/or amorphized and/or dissolved form such as, for example, eye drops, sprays and lotions (e.g. solutions, suspensions, vesicular/colloidal systems, emulsions, aerosols), powders for eye drops, sprays and lotions (e.g. ground active compound, mixtures, lyophilisates, precipitated active compound), semisolid eye preparations (e.g. hydrogels, in-situ hydrogels, creams and ointments), eye inserts (solid and semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable for intraocular administration are administration forms which operate in accordance with the prior art, which release the active compound rapidly and/or in a modified or controlled manner and which contain the active compound in crystalline and/or amorphized and/or dissolved form such as, for example, preparations for injection and concentrates for preparations for injection (e.g. solutions, suspensions, vesicular/colloidal systems, emulsions), powders for preparations for injection (e.g. ground active compound, mixtures, lyophilisates, precipitated active compound), gels for injection (semisolid preparations, e.g. hydrogels, in-situ hydrogels) and implants (solid preparations, e.g. biodegradable and nonbiodegradable implants, implantable pumps).

Preference is given to oral administration or, in the case of ophthalmologic disorders, extraocular and intraocular administration.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The inventive compounds can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctants.

The present invention further provides medicaments comprising at least one inventive compound, preferably together with one or more inert nontoxic pharmaceutically suitable excipients, and the use thereof for the purposes mentioned above.

In the case of parenteral administration, it has generally been found to be advantageous to administer amounts of about 5 to 250 mg every 24 hours to achieve effective results. In the case of oral administration, the amount is about 5 to 500 mg every 24 hours.

In spite of this, it may be necessary, if appropriate, to deviate from the amounts specified, specifically depending on body weight, administration route, individual behaviour towards the active ingredient, type of formulation, and time or interval of administration.

Unless stated otherwise, the percentages in the tests and examples which follow are percentages by weight; parts are parts by weight. Solvent ratios, dilution ratios and concentration data for the liquid/liquid solutions are based in each case on volume. "w/v" means "weight/volume". For example, "10% w/v" means: 100 ml of solution or suspension comprise 10 g of substance.

A) EXAMPLES

Abbreviations:
Boc tert-Butyloxycarbonyl
ca. circa
CDI carbonyldiimidazole
day(s), doublet (in NMR)
TLC thin-layer chromatography
DCM dichloromethane
DCI direct chemical ionization (in MS)
dd doublet of doublets (in NMR)
DMAP 4-dimethylaminopyridine
DMF N,N-dimethylformamide
DMSO dimethyl sulphoxide
of theory of theory (in yield)
eq. equivalent(s)
ESI electrospray ionization (in MS)
hour(s)
HATU O-(7-azabenzotriazol-1-yl)-N,N,N',N'-tetramethyluronium hexafluorophosphate
HPLC high-pressure, high-performance liquid chromatography
HV high vacuum
LC-MS liquid chromatography-coupled mass spectroscopy
LDA lithium diisopropylamide
multiplet (in NMR)
min minute(s)
MS mass spectroscopy
NMR nuclear magnetic resonance spectroscopy
quant. quantitative
RP reversed phase (in HPLC)
RT room temperature
$R_t$ retention time (in HPLC)
singlet (in NMR)
THF tetrahydrofuran
TFA trifluoroacetic acid
T3P 2,4,6-tripropyl-1,3,5,2,4,6-trioxatriphosphinane 2,4,6-trioxide
HPLC, LC-MS and GC Methods:
Method 1: Instrument: Waters ACQUITY SQD UPLC system; column: Waters Acquity UPLC HSS T3 1.8μ 50 mm×1 mm; mobile phase A: 1 l of water+0.25 ml of 99% strength formic acid, mobile phase B: 1 l of acetonitrile+0.25 ml of 99% strength formic acid; gradient: 0.0 mm 90% A→1.2 min 5% A→2.0 min 5% A; oven: 50° C.; flow rate: 0.40 ml/min; UV detection: 208-400 nm.

Method 2: Instrument: Waters ACQUITY SQD UPLC system; column: Waters Acquity UPLC HSS T3 1.8μ 50 mm×1 mm; mobile phase A: 1 l of water+0.25 ml of 99% strength formic acid, mobile phase B: 1 l of acetonitrile+0.25 ml of 99% strength formic acid; gradient: 0.0 mm 95% A→6.0 min 5% A→7.5 min 5% A; oven: 50° C.; flow rate: 0.35 ml/min; UV detection: 210-400 nm.

Method 3: Instrument: Micromass Quattro Premier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 mm 97% A→3.2 mm 5% A→4.0 mm 5% A; oven: 50° C.; flow rate: 0.3 ml/min; UV detection: 210 nm.

Method 4: Instrument: Micromass Quattro Premier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 mm 90% A→0.1 mm 90% A→1.5 mm 10% A→2.2 min 10% A; oven: 50° C.; flow rate: 0.33 ml/min; UV detection: 210 nm.

Method 5: Instrument: Thermo DFS, Trace GC Ultra; column: Restek RTX-35, 15 m×200 μm×0.33 μm; constant helium flow rate: 1.20 ml/min; oven: 60° C.; inlet: 220° C.; gradient: 60° C., 30° C./min→300° C. (maintained for 3.33 mm).

Method 6: MS instrument: Waters (Micromass) Quattro Micro; HPLC instrument: Agilent 1100 series; column: YMC-Triart C18 3μ 50×3 mm; mobile phase A: 1 l of water+0.01 mol of ammonium carbonate, mobile phase B: 1 l of acetonitrile; gradient: 0.0 min 100% A→2.75 mm 5% A→4.5 min 5% A; oven: 40° C.; flow rate: 1.25 ml/min; UV detection: 210 nm.

Method 7: MS instrument: Waters (Micromass) ZQ; HPLC instrument: Agilent 1100 series; column: Agient ZORBAX Extend-C18 3.0 mm×50 mm 3.5 micron; mobile phase A: 1 l of water+0.01 mol of ammonium carbonate, mobile phase B: 1 l of acetonitrile; gradient: 0.0 mm 98% A→0.2 min 98% A→3.0 min 5% A→4.5 min 5% A; oven: 40° C.; flow rate: 1.75 ml/min; UV detection: 210 nm.

Microwave: The microwave reactor used was a "single-mode" instrument of the Emrys™ Optimizer type.

When compounds according to the invention are purified by preparative HPLC by the above-described methods in which the eluents contain additives, for example trifluoroacetic acid, formic acid or ammonia, the compounds according to the invention may be obtained in salt form, for example as trifluoroacetate, formate or ammonium salt, if the compounds according to the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na+" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

STARTING MATERIALS

General Method 1A

Amide Coupling with HATU/Diisopropylethylamine

Under argon and at RT, the appropriate amine (1.1 eq.), N,N-diisopropylethylamine (2.2 eq.) and a solution of HATU (1.2 eq.) in a little DMF were added to a solution of the appropriate carboxylic acid (1.0 eq.) in dimethylformamide (7-15 ml/mmol). The reaction mixture was stirred at RT. After addition of water/ethyl acetate and phase separation, the organic phase was washed with water and with saturated aqueous sodium chloride solution, dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 2A

Hydrolysis of a Tert-Butyl Ester Using TFA

At RT, 20 eq. of TFA were added to a solution of 1.0 eq. of the appropriate tert-butyl ester derivative in dichloromethane (about 7 ml/mmol), and the mixture was stirred at RT for 1 to 8 h. The reaction mixture was then concentrated under reduced pressure and the residue was co-evaporated three times with dichloromethane and dried under reduced pressure. The crude product was then optionally purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 3B

Hydrolysis with Lithium Hydroxide

At RT, 3.0 eq. of lithium hydroxide were added to a solution of 1.0 eq. of the appropriate methyl or ethyl ester in tetrahydrofuran/water (3:1, ca. 10 ml/mmol). The reaction mixture was stirred at RT to 60° C. and then adjusted to pH 1 using aqueous 1N hydrochloric acid solution. After addition of water/ethyl acetate and phase separation, the aqueous phase was extracted three times with ethyl acetate. The combined organic phases were dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

Example 1.1A 3-(4-Aminophenyl)-1,2,4-oxadiazol-5(4H)-one

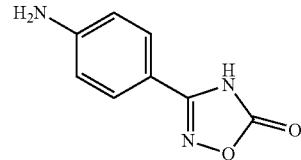 [SMILES: Nc1ccc(-c2noc(=O)[nH]2)cc1]

6.5 g (29 mmol, 4 eq.) of tin(II) chloride dihydrate were added to a solution of 1.5 g (7.2 mmol) of 3-(4-nitrophenyl)-1,2,4-oxadiazol-5(4H)-one in 75 ml of ethanol, and the mixture was stirred at 70° C. for 1 h. After cooling to RT, the reaction mixture was poured onto ice water and sodium hydrogen carbonate was carefully added to pH 8. The mixture was filtered through a filter layer and the residue was washed with ethyl acetate. The combined filtrates were concentrated under reduced pressure. The residue was stirred with dichloromethane and methanol, treated in an ultrasonic bath for 10 mm and then filtered. The filtrate was concentrated under reduced pressure and dried. Yield: 1.4 g (quant.)

LC-MS [Method 1]: $R_t$=0.44 min; MS (ESIpos): m/z=178 $(M+H)^+$ $^1$H-NMR (400 MHz, DMSO-$d_6$): δ [ppm]=7.42 (d, 2H), 6.51 (d, 2H), 5.23 (s, 2H), 4.13 (br. s, 1H).

Example 1.2A

4-Nitrobenzenecarboximidohydrazide

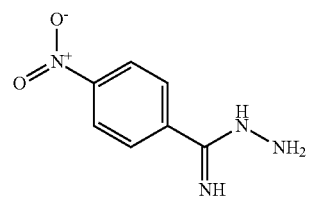 [SMILES: N=C(NN)c1ccc([N+](=O)[O-])cc1]

At 0° C., 5.2 ml (29.8 mmol, 3 eq.) of N,N-diisopropylethylamine and 0.62 g (80%, 9.9 mmol, 1.0 eq.) of hydrazine monohydrate were added to a solution of 2.0 g (9.9 mmol) of 4-nitrobenzenecarboximidamide monohydrochloride in 20 ml of methanol and the mixture was stirred at RT for 64 h. The reaction mixture was then added to 10% strength sodium chloride solution and, after addition of ethyl acetate and phase separation, extracted twice with ethyl acetate. The combined organic phases were dried over sodium sulphate and concentrated under reduced pressure. Yield: 1.7 g (93% of theory)

LC-MS [Method 6]: $R_t$=1.77 min; MS (ESIpos): m/z=181 $(M+H)^+$.

Example 1.2B 5-(4-Nitrophenyl)-3-(trifluoromethyl)-1H-1,2,4-triazole

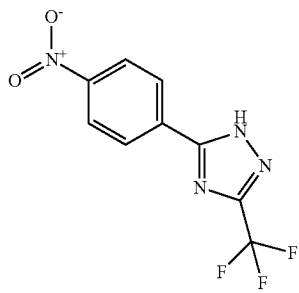 [SMILES: O=[N+]([O-])c1ccc(-c2nc(C(F)(F)F)n[nH]2)cc1]

At 0° C., 1.95 g (9.3 mmol, 1 eq) of trifluoroacetic anhydride were added to a solution of 1.7 g (9.3 mmol) of 4-nitrobenzenecarboximidohydrazide in 50 ml of dichloromethane and the mixture subsequently stirred at RT, whereupon after 20 min, 50 ml of acetonitrile were added to improve solubility of the reaction mixture. The reaction mixture was stirred at 50° C. for 3 h and then concentrated under reduced pressure. The residue was coevaporated three times with dichloromethane and dried under reduced pressure. Yield: 2.7 g (quant.)

LC-MS [Method 1]: $R_t$=0.94 min; MS (ESIpos): m/z=259 (M+H)$^+$.

Example 1.2C

4-[3-(Trifluoromethyl)-1H-1,2,4-triazol-5-yl]aniline

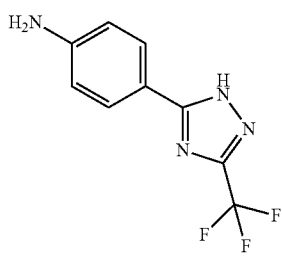 [SMILES: Nc1ccc(-c2nc(C(F)(F)F)n[nH]2)cc1]

8.9 g (39.7 mmol, 4 eq.) of tin(II) chloride dihydrate were added to a solution of 2.7 g (9.9 mmol) of 5-(4-nitrophenyl)-3-(trifluoromethyl)-1H-1,2,4-triazole in 110 ml of ethanol, and the mixture was stirred at 70° C. for 1 h. After cooling to RT, the reaction mixture was poured onto ice water and sodium hydrogen carbonate was carefully added to pH 8. The mixture was filtered through a filter layer and the residue was washed with ethyl acetate. After phase separation, the aqueous phase was washed twice with ethyl acetate. The combined organic phases were washed with aqueous sodium chloride solution, dried (magnesium sulphate), filtered and concentrated under reduced pressure. Yield: 1.9 g (79% of theory)

LC-MS [Method 6]: $R_t$=1.66 min; MS (ESIpos): m/z=229 (M+H)$^+$.

Example 1.3A tert-Butyl 5-(4-nitrophenyl)-3-oxo-2,3-dihydro-1H-pyrazole-1-carboxylate

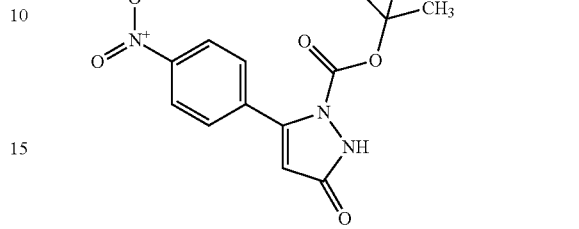

At RT, 2.7 g (12.2 mmol, 1.0 eq.) of di-tert-butyl dicarbonate and 1.7 ml (12.2 mmol, 1.0 eq.) of triethylamine were added to a solution of 2.5 g (12.2 mmol) of 5-(4-nitrophenyl)-1,2-dihydro-3H-pyrazol-3-one in 50 ml of dichloromethane, and the mixture was stirred at RT for 4 h. The reaction mixture was diluted with dichloromethane and water. After phase separation, the organic phase was dried (sodium sulphate), filtered and concentrated under reduced pressure. The crude product was purified by flash chromatography (silica gel 60, mobile phase: dichloromethane/methanol mixtures). Yield: 2.2 g (58% of theory).

LC-MS [Method 1]: $R_t$=1.07 min; MS (ESIpos): m/z=306 (M+H)$^+$.

Example 1.3B tert-Butyl 5-(4-aminophenyl)-3-oxo-2,3-dihydro-1H-pyrazole-1-carboxylate

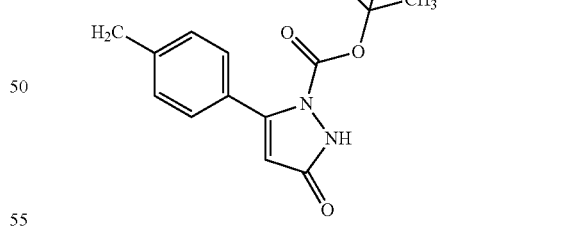

A solution of 2.2 g (7.1 mmol) of tert-butyl 5-(4-nitrophenyl)-3-oxo-2,3-dihydro-1H-pyrazole-1-carboxylate in 100 ml of ethanol was hydrogenated in the presence of 253 mg of palladium (10% on activated carbon) at RT and standard pressure. The reaction mixture was then filtered through Celite and the filtrate was concentrated under reduced pressure and dried. Yield: 1.99 g (92% of theory, purity 90%).

LC-MS [Method 7]: $R_t$=2.06 min; MS (ESIpos): m/z=276 (M+H)$^+$.

Example 2.1A

3-Aminocyclopent-2-en-1-one

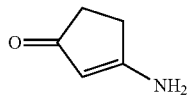

27.5 ml of aqueous ammonia solution (28%) were added to a solution of 5.5 g (43.6 mmol) of 3-ethoxy-2-cyclopenten-1-one in 55 ml of ethanol, and the mixture was stirred at 85° C. for 16 h. After cooling to RT, the reaction mixture was concentrated under reduced pressure and dried. Yield: 4.2 g (quant.)

GC/MS [Method 5]: $R_t$=4.78 min; MS (EI): m/z=97.

Example 2.2A tert-Butyl N-(3-oxocyclopent-1-en-1-yl)glycinate

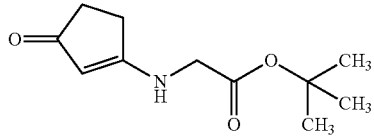

A solution of 6.7 g (68.6 mmol) of cyclopentane-1,3-dione, 9.0 g (68.6 mmol, 1.0 eq.) of tert-butyl glycinate and 1.3 g (6.8 mmol, 0.1 eq.) of 4-toluenesulphonic acid monohydrate in 350 ml of toluene was stirred under reflux for 3 h with a water separator. After cooling to RT, the toluene was removed under reduced pressure. After addition of water/dichloromethane and phase separation, the organic phase was washed with water and with saturated aqueous sodium chloride solution, dried (sodium sulphate), filtered and concentrated under reduced pressure. The residue was triturated with cyclohexane, filtered and dried under reduced pressure. Yield: 11.9 g (82% of theory)

LC-MS [Method 1]: $R_t$=0.58 min; MS (ESIpos): m/z=212 (M+H)⁺.

Example 2.3A tert-Butyl N-(3-oxocyclohex-1-en-1-yl)glycinate

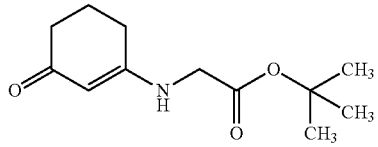 [SMILES: CC(C)(C)OC(=O)CNC1=CC(=O)CCC1]

A solution of 3.0 g (27.4 mmol) of cyclohexane-1,3-dione, 3.6 g (27.4 mmol, 1.0 eq.) of tert-butyl glycinate and 522 mg (2.74 mmol, 0.1 eq.) of 4-toluenesulphonic acid monohydrate in 150 ml of toluene was stirred under reflux for 3 h with a water separator. After cooling to RT, the toluene was removed under reduced pressure. After addition of water/dichloromethane and phase separation, the organic phase was washed with water and with saturated aqueous sodium chloride solution, dried (sodium sulphate), filtered and concentrated under reduced pressure. The residue was triturated with cyclohexane, filtered and dried under reduced pressure. Yield: 5.1 g (74% of theory, purity 90%)

LC-MS [Method 1]: $R_t$=0.61 min; MS (ESIpos): m/z=226 (M+H)⁺

¹H-NMR (400 MHz, DMSO-d₆): δ [ppm]=7.19 (br. s, 1H), 4.66 (br. s, 1H), 3.73 (d, 2H), 2.36-2.31 (m, 2H), 2.10-2.05 (m, 2H), 1.84-1.77 (m, 2H), 1.42 (s, 9H).

Example 3.1A

Methyl 4-(3-chlorophenyl)-2-methyl-6-oxo-1,4,5,6-tetrahydropyridine-3-carboxylate (racemate)

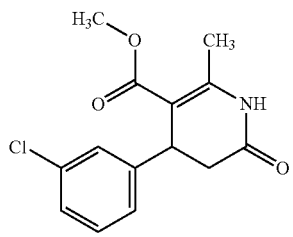 [SMILES: COC(=O)C1=C(C)NC(=O)CC1c1cccc(Cl)c1]

A solution of 7.5 g (53.4 mmol) of 3-chlorobenzaldehyde, 6.2 g (53.4 mmol, 1.0 eq.) of methyl acetoacetate, 7.7 g (53.4 mmol, 1.0 eq.) of 2,2-dimethyl-1,3-dioxane-4,6-dione and 4.3 g (55.8 mmol, 1.05 eq.) of ammonium acetate in 53 ml of glacial acetic acid was stirred under reflux for 5 h. After cooling the reaction mixture, the precipitate formed was filtered off with suction, washed with diethyl ether and dried under vacuum. Yield: 5.7 g (38% of theory)

LC-MS [Method 1]: $R_t$=0.91 min; MS (ESIpos): m/z=280 (M+H)⁺.

Example 3.1B

Methyl 1-(2-tert-butoxy-2-oxoethyl)-4-(3-chlorophenyl)-2-methyl-6-oxo-1,4,5,6-tetrahydropyridine-3-carboxylate (racemate)

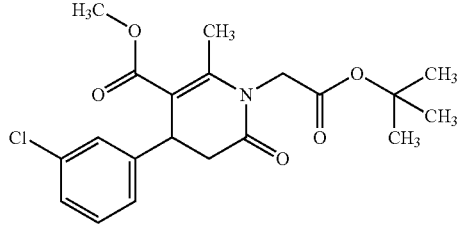 [SMILES: COC(=O)C1=C(C)N(CC(=O)OC(C)(C)C)C(=O)CC1c1cccc(Cl)c1]

At RT under argon, 6.0 g (31.0 mmol, 1.2 eq.) of tert-butyl bromoacetate and 7.1 g (51.6 mmol, 2.0 eq.) of potassium carbonate were added to a solution of 7.2 g (25.8 mmol) of methyl 4-(3-chlorophenyl)-2-methyl-6-oxo-1,4,5,6-tetrahydropyridine-3-carboxylate (racemate) in 253 ml of dimethylformamide. The reaction mixture was stirred overnight at 120° C., and another 2.5 g (12.9 mmol, 0.5 eq.) of tert-butyl bromoacetate were added, stirred for a further 2 h at 120° C., and again a further 2.5 g (12.9 mmol, 0.5 eq.) of tert-butyl bromoacetate were added and the mixture again stirred overnight at 120° C. After cooling to RT, the dimethylformamide was removed under reduced pressure. After addition of water/ethyl acetate and phase separation, the organic phase was washed with water and with saturated aqueous sodium chloride solution, dried (sodium sulphate), filtered and concentrated under reduced pressure. The crude product was then purified by flash chromatography (silica gel-60, eluent: dichloromethane-methanol mixtures). Yield: 3.9 g (34% of theory, purity 88%)

LC-MS [Method 1]: $R_t$=1.20 min; MS (ESIpos): m/z=394 (M+H)$^+$.

Example 3.1C

[6-(Bromomethyl)-4-(3-chlorophenyl)-5-(methoxycarbonyl)-2-oxo-3,4-dihydropyridin-1(2H)-yl]acetic acid (racemate)

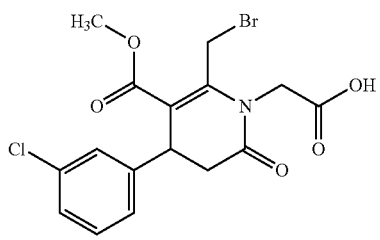 [SMILES: COC(=O)C1=C(CBr)N(CC(=O)O)C(=O)CC1c1cccc(Cl)c1]

With ice cooling, 1.6 g (9.9 mmol, 1.0 eq.) of bromine was added dropwise to a solution of 3.9 g (9.9 mmol) of methyl 1-(2-tert-butoxy-2-oxoethyl)-4-(3-chlorophenyl)-2-methyl-6-oxo-1,4,5,6-tetrahydropyridine-3-carboxylate (racemat) in 79 ml of dichlormethane and the reaction mixture was stirred at RT for 60 min. After addition of further dichloromethane, the reaction mixture was washed with saturated, aqueous sodium thiosulphate solution and, after phase separation, the organic phase was dried (sodium sulphate), filtered and concentrated under reduced pressure. Yield: 3.4 g (66% of theory, purity 79%)

LC-MS [Method 1]: $R_t$=0.96 min; MS (ESIpos): m/z=416 (M+H)$^+$.

Example 3.1D

[4-(3-Chlorophenyl)-2,5-dioxo-2,3,4,5,6,7-hexahydro-1H-pyrrolo[3,4-b]pyridin-1-yl]acetic acid (racemate)

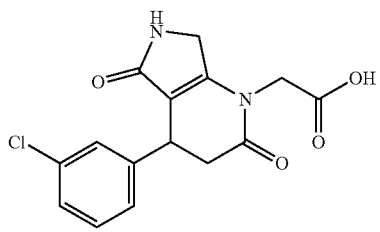 [SMILES: O=C(O)CN1C(=O)CC(c2cccc(Cl)c2)C2=C1CNC2=O]

12 ml of an ammonia solution (7 molar in methanol) were added to a solution of 1.4 g (1.7 mmol, 50% pure) of [6-(bromomethyl)-4-(3-chlorophenyl)-5-(methoxycarbonyl)-2-oxo-3,4-dihydropyridin-1(2H)-yl]acetic acid (racemate) in 8 ml of acetonitrile and the mixture was stirred at RT for 30 min. The reaction mixture was concentrated under reduced pressure and the residue was stirred with 60 ml of a 0.5 molar aqueous hydrochloric acid solution. The precipitate was filtered off, washed with water and dried under reduced pressure. Yield: 680 mg (93% of theory, purity 74%)

LC-MS [Method 1]: $R_t$=0.58 min; MS (ESIpos): m/z=321 (M+H)$^+$.

Example 3.1E

2-[4-(3-Chlorophenyl)-2,5-dioxo-2,3,4,5,6,7-hexahydro-1H-pyrrolo[3,4-b]pyridin-1-yl]-N-[4-(1H-tetrazol-5-yl)phenyl]acetamide (racemate)

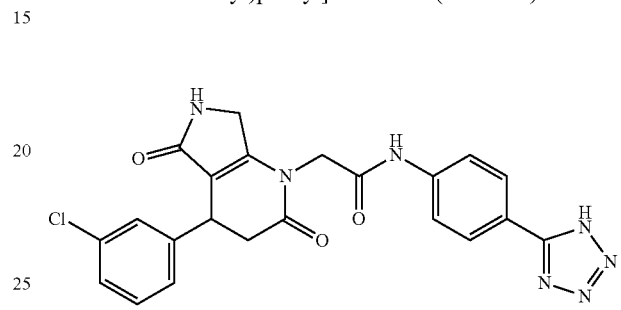

According to general method 1A, 500 mg (1.1 mmol, 70% pure) of [4-(3-chlorophenyl)-2,5-dioxo-2,3,4,5,6,7-hexahydro-1H-pyrrolo[3,4-b]pyridin-1-yl]acetic acid (racemate) were reacted with 211 mg (1.3 mmol, 1.2 eq.) of 4-(1H-tetrazol-5-yl)aniline. The crude product was then purified by preparative HPLC (Reprosil C18, water/acetonitrile gradient). Yield: 24 mg (5% of theory)

LC-MS [Method 1]: $R_t$=0.75 min; MS (ESIpos): m/z=464 (M+H)$^+$ $^1$H-NMR (400 MHz, DMSO-$d_6$): δ [ppm]=10.64 (s, 1H), 8.01 (d, 2H), 7.84-7.80 (m, 3H), 7.43 (s, 1H), 7.37-7.28 (m, 3H), 4.59 (d, 1H), 4.36 (d, 1H), 4.12 (dd, 2H), 3.98 (d, 1H), 3.23 (dd, 1H), 2.63 (d, 1H).

Example 3.2A

Methyl 4-(2,5-dichlorophenyl)-2-methyl-6-oxo-1,4,5,6-tetrahydropyridine-3-carboxylate (racemate)

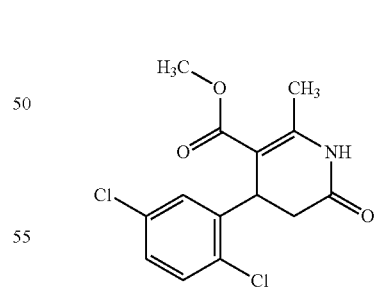

A solution of 11.5 g (36.3 mmol) of 2,5-dichlorobenzaldehyde, 4.2 g (36.3 mmol, 1.0 eq.) of methyl acetoacetate, 5.2 g (36.3 mmol, 1.0 eq.) of 2,2-dimethyl-1,3-dioxane-4,6-dione and 2.9 g (38.1 mmol, 1.05 eq.) of ammonium acetate in 35 ml of glacial acetic acid was stirred under reflux for 5 h. After cooling the reaction mixture, the precipitate formed was filtered off, washed with water and dried under vacuum. Yield: 4.0 g (33% of theory, purity 92%)

LC-MS [Method 1]: $R_t$=0.95 min; MS (ESIpos): m/z=314 (M+H)$^+$.

Example 3.2B

Methyl 1-(2-tert-butoxy-2-oxoethyl)-4-(2,5-dichlorophenyl)-2-methyl-6-oxo-1,4,5,6-tetrahydropyridine-3-carboxylate (racemate)

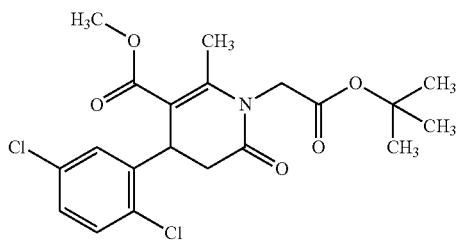 [SMILES: COC(=O)C1=C(C)N(CC(=O)OC(C)(C)C)C(=O)CC1c1cc(Cl)ccc1Cl]

At RT, 1.3 g (6.7 mmol, 1.4 eq.) of tert-butyl bromoacetate and 1.3 g (9.5 mmol, 2.0 eq.) of potassium carbonate were added to a solution of 1.6 g (4.8 mmol) of 4-(2,5-dichlorophenyl)-2-methyl-6-oxo-1,4,5,6-tetrahydropyridine-3-carboxylate (racemate) in 30 ml of dimethylformamide and the mixture was stirred at 120° C. for 2 h. After cooling to RT, the reaction mixture was concentrated under reduced pressure. After addition of water/ethyl acetate and phase separation, the organic phase was washed with water and with saturated aqueous sodium chloride solution, dried (sodium sulphate), filtered and concentrated under reduced pressure. Yield: 2.1 g (quant.)

LC-MS [Method 2]: $R_t$=1.31 min; MS (ESIpos): m/z=371 (M+H-tert-butyl)$^+$.

Example 3.2C

Methyl 2-(bromomethyl)-1-(2-tert-butoxy-2-oxoethyl)-4-(2,5-dichlorophenyl)-6-oxo-1,4,5,6-tetrahydropyridine-3-carboxylate (racemate)

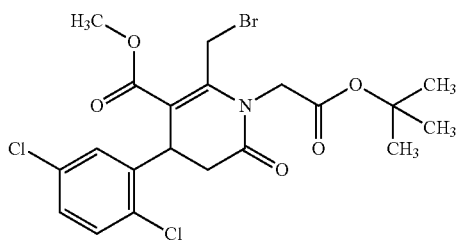 [SMILES: COC(=O)C1=C(CBr)N(CC(=O)OC(C)(C)C)C(=O)CC1c1cc(Cl)ccc1Cl]

With ice cooling, 0.8 g (4.9 mmol, 1.0 eq.) of bromine was added dropwise to a solution of 2.1 g (4.9 mmol) of methyl 1-(2-tert-butoxy-2-oxoethyl)-4-(2,5-dichlorophenyl)-2-methyl-6-oxo-1,4,5,6-tetrahydropyridine-3-carboxylate (racemat) in 40 ml of dichlormethane and the reaction mixture was stirred at RT for 60 mm. After addition of further dichloromethane, the reaction mixture was washed with saturated, aqueous sodium thiosulphate solution and the organic phase was dried (sodium sulphate), filtered and concentrated under reduced pressure. Yield: 2.2 g (88% of theory, purity 82%)

LC-MS [Method 2]: $R_t$=1.01 min; MS (ESIpos): m/z=450 (M+H-tert-butyl)$^+$.

Example 3.2D tert-Butyl [4-(2,5-dichlorophenyl)-6-methyl-2,5-dioxo-2,3,4,5,6,7-hexahydro-1H-pyrrolo[3,4-b]pyridin-1-yl]acetate (racemate)

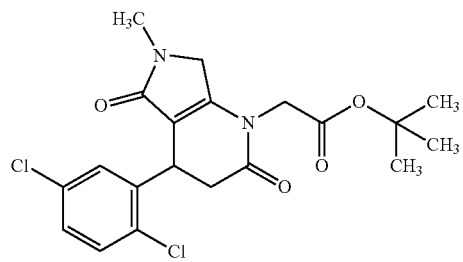 [SMILES: CN1CC2=C(C1=O)C(c1cc(Cl)ccc1Cl)CC(=O)N2CC(=O)OC(C)(C)C]

2.2 ml (4.4 mmol, 1.5 eq.) of a methylamine solution (2 molar in tetrahydrofuran) were added to a solution of 1.8 g (2.9 mmol, 82% pure) of methyl 2-(bromomethyl)-1-(2-tert-butoxy-2-oxoethyl)-4-(2,5-dichlorophenyl)-6-oxo-1,4,5,6-tetrahydropyridine-3-carboxylate (racemat) in 70 ml of tetrahydrofuran. The reaction mixture was stirred at RT for 60 min and concentrated under reduced pressure. The residue was stirred with acetonitrile in an ice bath, the precipitate filtered off and the mother liquor concentrated under reduced pressure. The crude product was then purified by flash chromatography (silica gel-60, eluent: dichloromethane-methanol mixtures). Yield: 0.42 g (28% of theory, purity 83%)

LC-MS [Method 2]: $R_t$=1.06 min; MS (ESIpos): m/z=425 (M+H)$^+$.

Example 3.2E tert-Butyl [4-(2,5-dichlorophenyl)-6-methyl-2,5-dioxo-2,5,6,7-tetrahydro-1H-pyrrolo[3,4-b]pyridin-1-yl]acetate

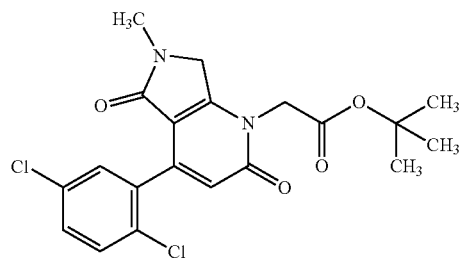 [SMILES: CN1Cc2c(c(-c3cc(Cl)ccc3Cl)cc(=O)n2CC(=O)OC(C)(C)C)C1=O]

A solution of 1781 mg (3.25 mmol, 5.0 eq.) of ammonium cerium(IV) nitrate in 2.5 ml of water was added to a solution of 333 mg (0.65 mmol, 83% pure) of tert-butyl [4-(2,5-dichlorophenyl)-6-methyl-2,5-dioxo-2,3,4,5,6,7-hexahydro-1H-pyrrolo[3,4-b]pyridin-1-yl]acetate (racemate) in 10 ml of dioxane and the mixture was stirred at 50° C. for 7 h. After cooling to RT, the reaction mixture was concentrated under reduced pressure. After addition of water/ethyl acetate and phase separation, the organic phase was washed with water and with saturated aqueous sodium chloride solution, dried

Example 3.2F

[4-(2,5-dichlorophenyl)-6-methyl-2,5-dioxo-2,5,6,7-tetrahydro-1H-pyrrolo[3,4-b]pyridin-1-yl]acetic acid

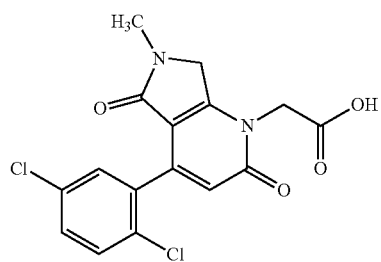 [SMILES: CN1Cc2c(c(-c3cc(Cl)ccc3Cl)cc(=O)n2CC(=O)O)C1=O]

280 mg (0.66 mmol, 22% purity) of tert-Butyl [4-(2,5-dichlorophenyl)-6-methyl-2,5-dioxo-2,5,6,7-tetrahydro-1H-pyrrolo[3,4-b]pyridin-1-yl]acetate were hydrolysed with TFA according to general method 2A. Yield: 328 mg (76% of theory, purity 56%)

LC-MS [Method 1]: $R_t$=0.65 min; MS (ESIpos): m/z=367 (M+H)$^+$.

Example 4.1A 5-(2,5-Dichlorobenzylidene)-2,2-dimethyl-1,3-dioxane-4,6-dione

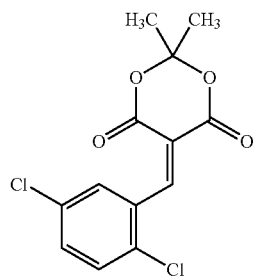 [SMILES: CC1(C)OC(=O)C(=Cc2cc(Cl)ccc2Cl)C(=O)O1]

358 µl (3.6 mmol, 0.2 eq.) of piperidine and 1.2 ml (21.0 mmol, 1.1 eq.) of acetic acid were added to a solution of 2.75 g (19.0 mmol) of 2,2-dimethyl-1,3-dioxane-4,6-dione and 5.0 g (28.6 mmol, 1.5 eq.) of 2,5-dichlorobenzaldehyde in 250 ml of toluene and stirred for 5 h under reflux with a water separator. After cooling to RT, the reaction mixture was concentrated under reduced pressure, the residue triturated with cyclohexane, filtered and dried under vacuum. Yield: 4.94 g (82% of theory)

$^1$H-NMR (400 MHz, DMSO-d$_6$): δ [ppm]=8.40 (s, 1H), 7.78 (d, 1H), 7.64 (d, 1H), 7.59 (dd, 1H), 1.79 (s, 6H).

(sodium sulphate), filtered and concentrated under reduced pressure. Yield: 301 mg (24% of theory, purity 22%)

LC-MS [Method 2]: $R_t$=1.02 min; MS (ESIpos): m/z=423 (M+H)$^+$.

Example 4.1B tert-Butyl [4-(2,5-dichlorophenyl)-2,5-dioxo-2,3,4,5,6,7-hexahydro-1H-cyclopenta[b]pyridin-1-yl]acetate (racemate)

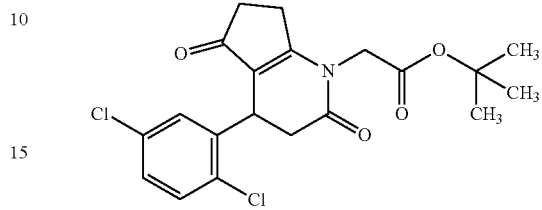

A solution of 5.0 g (23.7 mmol) of 5-(2,5-dichlorobenzylidene)-2,2-dimethyl-1,3-dioxane-4,6-dione and 7.1 g (23.7 mmol, 1.0 eq.) of tert-butyl N-(3-oxocyclopent-1-en-1-yl)glycinate in 80 ml of ethanol was stirred under reflux for 30 min After cooling to RT, the reaction mixture was concentrated under reduced pressure. The crude product was purified by flash chromatography (silica gel-60, eluent: cyclohexane-ethyl acetate mixtures). Yield: 7.4 g (72% of theory, purity 94%)

LC-MS [Method 1]: $R_t$=1.12 min; MS (ESIpos): m/z=410 (M+H)$^+$.

Example 4.1C

[4-(2,5-Dichlorophenyl)-2,5-dioxo-2,3,4,5,6,7-hexahydro-1H-cyclopenta[b]pyridin-1-yl]acetic acid (racemate)

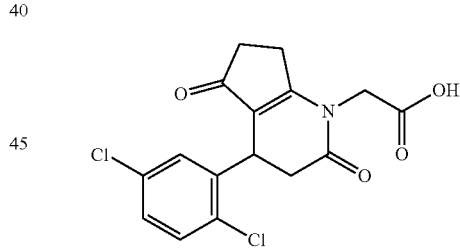

A solution of 1464 mg (2.67 mmol, 4.0 eq.) of ammonium cerium(IV) nitrate in 2.7 ml of water was added to a solution of 274 mg (0.67 mmol) of tert-butyl [4-(2,5-dichlorophenyl)-2,5-dioxo-2,3,4,5,6,7-hexahydro-1H-cyclopenta[b]pyridin-1-yl]acetate (racemate) in 10 ml of acetone and the mixture was stirred at RT overnight. After cooling to RT, the reaction mixture was then concentrated under reduced pressure. After addition of water/dichloromethane and phase separation, the organic phase was washed with water and with saturated aqueous sodium chloride solution, dried (sodium sulphate), filtered and concentrated under reduced pressure. Yield: 211 mg (63% of theory, purity 71%)

LC-MS [Method 1]: $R_t$=1.08 min; MS (ESIpos): m/z=354 (M+H-$^{tert}$-butyl)+.

Example 4.1D

2-[4-(2,5-Dichlorophenyl)-2,5-dioxo-2,3,4,5,6,7-hexahydro-1H-cyclopenta[b]pyridin-1-yl]-N-[4-(1H-tetrazol-5-yl)phenyl]acetamide (racemate)

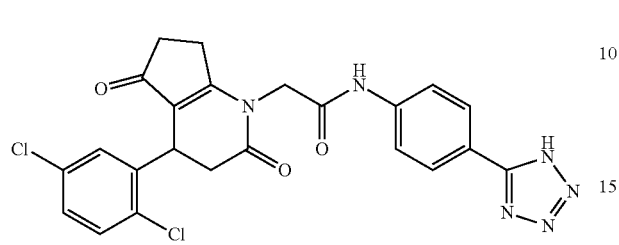

According to general method 1A, 211 mg (0.42 mmol, 71% pure) of [4-(2,5-dichlorophenyl)-2,5-dioxo-2,3,4,5,6,7-hexahydro-1H-cyclopenta[b]pyridin-1-yl]acetic acid (racemate) were reacted with 82 mg (0.51 mmol, 1.2 eq.) of 4-(1H-tetrazol-5-yl)aniline. Yield: 138 mg (58% of theory, purity 89%)

LC-MS [Method 1]: $R_t$=0.87 min; MS (ESIpos): m/z=497 (M+H)$^+$.

Example 4.2A tert-Butyl [4-(2,5-dichlorophenyl)-2,5-dioxo-2,5,6,7-tetrahydro-1H-cyclopenta[b]pyridin-1-yl]acetate

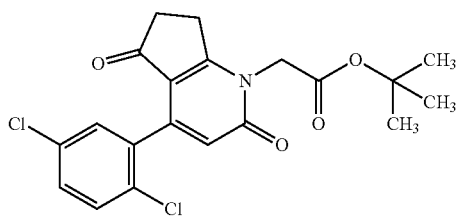 [SMILES: CC(C)(C)OC(=O)Cn1c2c(c(-c3cc(Cl)ccc3Cl)cc1=O)C(=O)CC2]

A solution of 29.2 g (53.3 mmol, 5.0 eq.) of ammonium cerium(IV) nitrate in 46 ml of water was added to a solution of 4.7 g (10.7 mmol, 94% pure) of tert-butyl [4-(2,5-dichlorophenyl)-2,5-dioxo-2,3,4,5,6,7-hexahydro-1H-cyclopenta[b]pyridin-1-yl]acetate (racemate) in 186 ml of dioxane and the mixture was stirred at 50° C. for 5 h. After cooling to RT, the reaction mixture was concentrated under reduced pressure. After addition of water/dichloromethane and phase separation, the organic phase was washed with water and with saturated aqueous sodium chloride solution, dried (sodium sulphate), filtered and concentrated under reduced pressure. Yield: 5.5 g (quant.)

LC-MS [Method 1]: $R_t$=1.10 min; MS (ESIpos): m/z=408 (M+H)$^+$.

Example 4.2B

[4-(2,5-Dichlorophenyl)-2,5-dioxo-2,5,6,7-tetrahydro-1H-cyclopenta[b]pyridin-1-yl]acetic acid

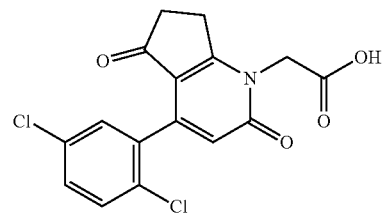 [SMILES: O=C(O)Cn1c2c(c(-c3cc(Cl)ccc3Cl)cc1=O)C(=O)CC2]

2.0 g (5.0 mmol) of tert-Butyl [4-(2,5-dichlorophenyl)-2,5-dioxo-2,5,6,7-tetrahydro-1H-cyclopenta[b]pyridin-1-yl]acetate were hydrolysed with TFA according to general method 2A. Yield: 1.9 g (95% of theory, purity 89%)

LC-MS [Method 1]: $R_t$=0.72 min; MS (ESIpos): m/z=352 (M+H)$^+$.

Example 4.3A tert-Butyl 4-({[4-(2,5-dichlorophenyl)-2,5-dioxo-2,5,6,7-tetrahydro-1H-cyclopenta[b]pyridin-1-yl]acetyl}amino)benzoate

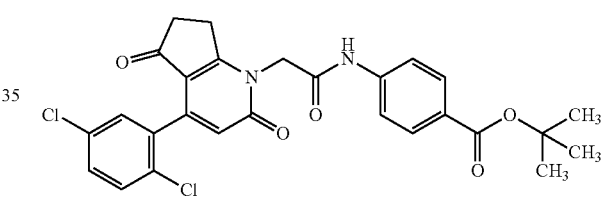

According to general method 1A, 119 mg (0.30 mmol, 89% pure) of [4-(2,5-dichlorophenyl)-2,5-dioxo-2,5,6,7-tetrahydro-1H-cyclopenta[b]pyridin-1-yl]acetic acid were reacted with 64 mg (0.33 mmol, 1.1 eq.) of tert-butyl 4-aminobenzoate. Yield: 48 mg (29% of theory, purity 94%)

LC-MS [Method 1]: $R_t$=1.14 min; MS (ESIpos): m/z=527 (M+H)$^+$.

Example 4.4A tert-Butyl 5-[4-({[4-(2,5-dichlorophenyl)-2,5-dioxo-2,5,6,7-tetrahydro-1H-cyclopenta[b]pyridin-1-yl]acetyl}amino)phenyl]-3-oxo-2,3-dihydro-1H-pyrazole-1-carboxylate

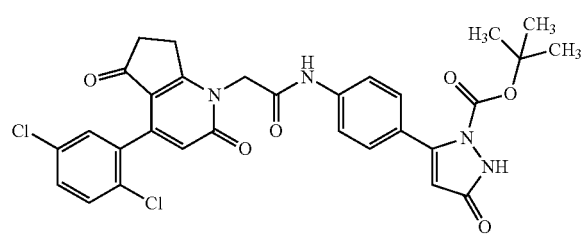 [SMILES: CC(C)(C)OC(=O)n1[nH]c(=O)cc1-c1ccc(NC(=O)Cn2c3c(c(-c4cc(Cl)ccc4Cl)cc2=O)C(=O)CC3)cc1]

According to general method 1A, 102 mg (0.25 mmol, 86% pure) of [4-(2,5-dichlorophenyl)-2,5-dioxo-2,5,6,7-tetrahydro-1H-cyclopenta[b]pyridin-1-yl]acetic acid were reacted with 95 mg (0.28 mmol, 1.1 eq.) of tert-butyl 5-(4-aminophenyl)-3-oxo-2,3-dihydro-1H-pyrazole-1-carboxylate. Yield: 53 mg (35% of theory)

LC-MS [Method 1]: $R_t$=1.12 min; MS (ESIpos): m/z=609 (M+H)+.

Example 5.1A 5-(2-Bromo-5-chlorobenzylidene)-2,2-dimethyl-1,3-dioxane-4,6-dione

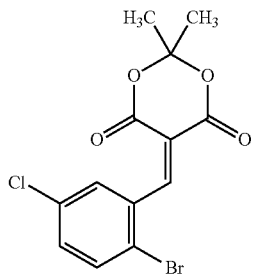 [SMILES: CC1(C)OC(=O)C(=Cc2cc(Cl)ccc2Br)C(=O)O1]

0.6 ml (6.1 mmol, 0.2 eq.) of piperidine and 2 ml (35.1 mmol, 1.1 eq.) of acetic acid were added to a solution of 4.6 g (31.9 mmol) of 2,2-dimethyl-1,3-dioxane-4,6-dione and 10.5 g (47.8 mmol, 1.5 eq.) of 2-bromo-5-chlorobenzaldehyde in 450 ml of toluene and the mixture was stirred for 3 h under reflux with a water separator. After cooling to RT, the reaction mixture was concentrated under reduced pressure, the residue triturated with diethyl ether, filtered and dried under vacuum. Yield: 9.3 g (84% of theory)

$^1$H-NMR (400 MHz, DMSO-$d_6$): δ [ppm]=8.35 (s, 1H), 7.78 (d, 1H), 7.71 (d, 1H), 7.50 (dd, 1H), 1.79 (s, 6H).

Example 5.1B 4-(2-Bromo-5-chlorophenyl)-3,4,6,7-tetrahydro-1H-cyclopenta[b]pyridine-2,5-dione (racemate)

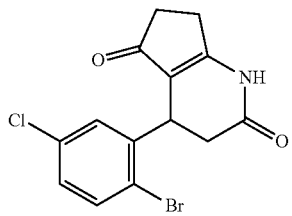 [SMILES: O=C1CC(c2cc(Cl)ccc2Br)C2=C(CCC2=O)N1]

A solution of 2.6 g (26.9 mmol) of 3-aminocyclopent-2-en-1-one and 9.3 g (26.9 mmol, 1.0 eq.) of 5-(2-bromo-5-chlorobenzylidene)-2,2-dimethyl-1,3-dioxane-4,6-dione in 100 ml of dioxane was stirred at 80° C. After 3 h, the reaction mixture was cooled to RT and 3.1 g (8.1 mmol, 0.3 eq.) of HATU and 0.9 ml (5.4 mmol, 0.2 eq.) of N,N-diisopropylethylamine were added, the mixture was stirred overnight at RT and concentrated under reduced pressure. After addition of water/ethyl acetate and phase separation, the organic phase was dried (sodium sulphate), filtered and concentrated under reduced pressure. The crude product was then purified by flash chromatography (silica gel-60, eluent: dichloromethane-methanol mixtures). Yield: 4.95 g (44% of theory, purity 81%

LC-MS [Method 1]: $R_t$=0.84 min; MS (ESIpos): m/z=340 (M+H)+.

Example 5.1C 4-(2-Bromo-5-chlorophenyl)-6,7-dihydro-1H-cyclopenta[b]pyridine-2,5-dione

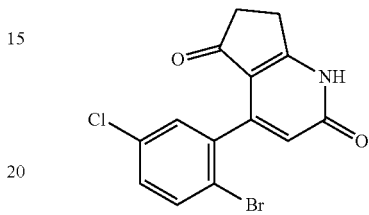

A solution of 32.3 g (58.9 mmol, 5.0 eq.) of ammonium cerium(IV) nitrate in 60 ml of water was added to a solution of 4.95 g (11.8 mmol, 81% pure) of 4-(2-bromo-5-chlorophenyl)-3,4,6,7-tetrahydro-1H-cyclopenta[b]pyridine-2,5-dione (racemate) in 180 ml of dioxane and the mixture was stirred at 50° C. for 3 h. After cooling to RT, the reaction mixture was concentrated under reduced pressure. After addition of water/dichloromethane and phase separation, the organic phase was washed with water and with saturated aqueous sodium chloride solution, dried (sodium sulphate), filtered and concentrated under reduced pressure. The residue was triturated with diethyl ether, filtered and dried under reduced pressure. Yield: 3.1 g (70% of theory, purity 90%)

LC-MS [Method 3]: $R_t$=1.78 min; MS (ESIpos): m/z=338 (M+H-$^{tert}$-butyl)+.

$^1$H-NMR (400 MHz, DMSO-$d_6$): δ [ppm]=12.74 (s, 1H), 7.69 (d, 1H), 7.42 (dd, 1H), 7.36 (d, 1H), 6.10 (s, 1H), 3.03-2.86 (m, 2H), 2.56-2.46 (m, 2H).

Example 5.1D tert-Butyl [4-(2-bromo-5-chlorophenyl)-2,5-dioxo-2,5,6,7-tetrahydro-1H-cyclopenta[b]pyridin-1-yl]acetate

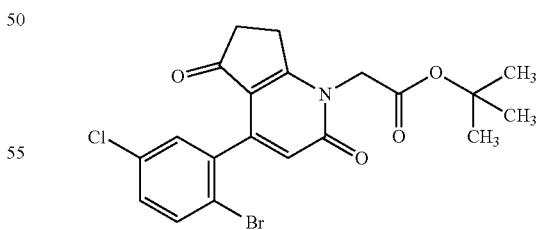

A solution of 300 mg (0.80 mmol, 90% pure) of 4-(2-bromo-5-chlorophenyl)-6,7-dihydro-1H-cyclopenta[b]pyridine-2,5-dione, 0.14 ml (0.96 mmol, 1.2 eq.) of tert-butyl bromoacetate and 165 mg (1.20 mmol) of potassium carbonate in 18 ml of dimethylformamide was stirred at 120° C. for 2 h. After cooling to RT, the reaction mixture was concentrated under reduced pressure. After addition of water/ethyl acetate and phase separation, the organic phase was washed with water and with saturated aqueous sodium chloride solution, dried (sodium sulphate), filtered and concentrated under reduced pressure. The residue was triturated with diethyl ether, filtered and dried under reduced pressure. Yield: 169 mg (47% of theory)

LC-MS [Method 1]: $R_t$=1.11 min; MS (ESIpos): m/z=452 (M+H-$^{tert}$-butyl)+.

$^1$H-NMR (400 MHz, DMSO-$d_6$): δ [ppm]=7.70 (d, 1H), 7.43 (dd, 1H), 7.40 (d, 1H), 6.29 (s, 1H), 4.79 (s, 2H), 3.07-3.01 (m, 2H), 2.61-2.55 (m, 2H), 1.45 (s, 9H).

Example 5.1E

[4-(2-bromo-5-chlorophenyl)-2,5-dioxo-2,5,6,7-tetrahydro-1H-cyclopenta[b]pyridin-1-yl]acetic acid

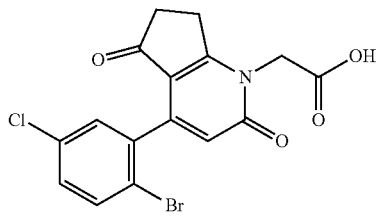 [SMILES: O=C(O)Cn1c2c(c(-c3cc(Cl)ccc3Br)cc1=O)C(=O)CC2]

140 mg (0.31 mmol) of tert-Butyl [4-(2-bromo-5-chlorophenyl)-2,5-dioxo-2,5,6,7-tetrahydro-1H-cyclopenta[b]pyridin-1-yl]acetate were hydrolysed with TFA according to general method 2A. Yield: 90 mg (69% of theory, purity 94%).

LC-MS [Method 1]: $R_t$=0.76 min; MS (ESIpos): m/z=396 (M+H)$^+$.

Example 6.1A

5-[5-Chloro-2-(trifluoromethyl)benzylidene]-2,2-dimethyl-1,3-dioxane-4,6-dione

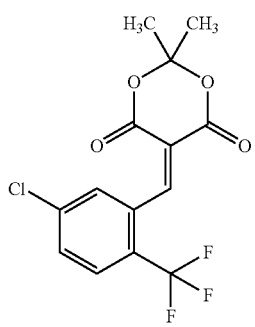 [SMILES: CC1(C)OC(=O)C(=Cc2cc(Cl)ccc2C(F)(F)F)C(=O)O1]

0.4 ml (4.0 mmol, 0.2 eq.) of piperidine and 1.3 ml (23.0 mmol, 1.1 eq.) of acetic acid were added to a solution of 3.0 g (20.8 mmol) of 2,2-dimethyl-1,3-dioxane-4,6-dione and 5.0 g (24.0 mmol, 1.2 eq.) of 5-chloro-2-(trifluoromethyl) benzaldehyde in 295 ml of toluene and the mixture stirred for 3 h under reflux with a water separator. After cooling to RT, the reaction mixture was concentrated under reduced pressure, the residue triturated with diethyl ether, filtered and dried under vacuum. Yield: 5.4 g (69% of theory, purity 89%)

$^1$H-NMR (400 MHz, DMSO-$d_6$): δ [ppm]=8.57 (s, 1H), 7.87 (d, 1H), 7.75 (d, 1H), 7.70 (s, 1H), 1.78 (s, 6H).

Example 6.1B

4-[5-Chloro-2-(trifluoromethyl)phenyl]-3,4,6,7-tetrahydro-1H-cyclopenta[b]pyridine-2,5-dione (racemate)

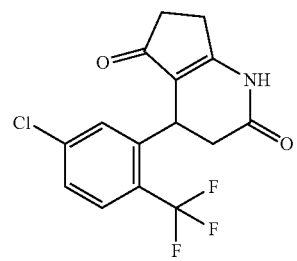 [SMILES: O=C1CC(c2cc(Cl)ccc2C(F)(F)F)C2=C(CCC2=O)N1]

A solution of 1.4 g (14.4 mmol) of 3-aminocyclopent-2-en-1-one and 5.4 g (14.4 mmol) of 5-[5-chloro-2-(trifluoromethyl)benzylidene]-2,2-dimethyl-1,3-dioxane-4,6-dione in 60 ml of dioxane was stirred at 80° C. After 3 h the reaction mixture was cooled to RT and 2.2 g (5.7 mmol) of HATU and 1.0 ml (5.7 mmol) of N,N-diisopropylethylamine were added and the mixture stirred overnight at RT and concentrated under reduced pressure. After addition of water/diethyl ether and phase separation, the precipitate formed was filtered off, washed with diethyl ether and dried under vacuum. Water/ethyl acetate was added to the mother liquor and, after phase separation, the organic phase was dried (sodium sulphate), filtered and concentrated under reduced pressure. The crude product was then purified by flash chromatography (silica gel-60, eluent: dichloromethane-methanol mixtures). Yield: 1.46 g (28% of theory, 92% purity) and 1.30 g (26% of theory, 93% purity)

LC-MS [Method 1]: $R_t$=0.85 min; MS (ESIpos): m/z=330 (M+H)$^+$ $^1$H-NMR (400 MHz, DMSO-$d_6$): δ [ppm]=10.85 (s, 1H), 7.74 (d, 1H), 7.52 (dd, 1H), 7.24 (d, 1H), 4.18 (t, 1H), 2.98 (dd, 1H), 2.78 (dd, 1H), 2.67-2.60 (m, 1H), 2.47-2.33 (m, 3H).

Example 6.1C

4-[5-Chloro-2-(trifluoromethyl)phenyl]-6,7-dihydro-1H-cyclopenta[b]pyridine-2,5-dione

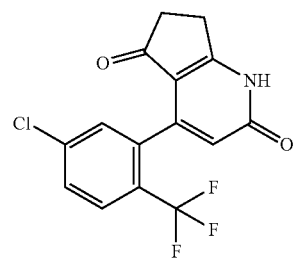 [SMILES: O=C1CCc2[nH]c(=O)cc(-c3cc(Cl)ccc3C(F)(F)F)c21]

A solution of 21.3 g (38.9 mmol, 5.0 eq.) of ammonium cerium(IV) nitrate in 45 ml of water was added to a solution of 2.8 g (7.8 mmol, 93% pure) of 4-[(5-chloro-2-(trifluoromethyl)phenyl]-3,4,6,7-tetrahydro-1H-cyclopenta[b]pyridine-2,5-dione (racemate) in 130 ml of dioxane and the mixture was stirred at 50° C. for 5 h. After cooling to RT, the reaction mixture was concentrated under reduced pressure. After addition of water/ethyl acetate and phase separation, the organic phase was washed with water and with saturated aqueous sodium chloride solution, dried (sodium sulphate), filtered and concentrated under reduced pressure. The residue was triturated with diethyl ether, filtered and dried under reduced pressure. Yield: 1.7 g (63% of theory)

LC-MS [Method 1]: $R_t$=0.83 min; MS (ESIpos): m/z=328 (M+H)$^+$ $^1$H-NMR (400 MHz, DMSO-d$_6$): δ [ppm]=12.74 (s, 1H), 7.82 (d, 1H), 7.70 (d, 1H), 7.44 (s, 1H), 6.10 (s, 1H), 2.98-2.92 (m, 2H), 2.40-2.44 (m, 2H).

Example 6.1D tert-Butyl {4-[5-chloro-2-(trifluoromethyl)phenyl]-2,5-dioxo-2,5,6,7-tetrahydro-1H-cyclopenta[b]pyridin-1-yl}acetate

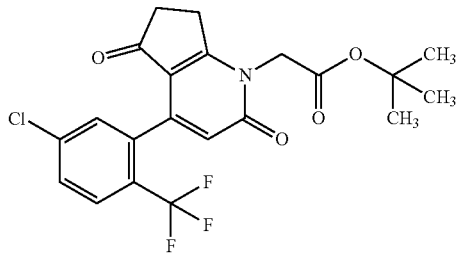 [SMILES: CC(C)(C)OC(=O)Cn1c2c(c(-c3cc(Cl)ccc3C(F)(F)F)cc1=O)C(=O)CC2]

A solution of 700 mg (2.1 mmol) of 4-[5-chloro-2-(trifluoromethyl)phenyl]-6,7-dihydro-1H-cyclopenta[b]pyridine-2,5-dione, 0.36 ml (2.5 mmol, 1.2 eq.) of tert-butyl bromoacetate and 425 mg (1.5 mmol) of potassium carbonate in 15 ml of dimethylformamide was stirred at 120° C. for 2 h. After cooling to RT, the reaction mixture was concentrated under reduced pressure. After addition of water/ethyl acetate and phase separation, the organic phase was washed with water and with saturated aqueous sodium chloride solution, dried (sodium sulphate), filtered and concentrated under reduced pressure. The crude product was then purified by flash chromatography (silica gel-60, eluent: cyclohexane-ethyl acetate mixtures). Yield: 625 mg (67% of theory)

LC-MS [Method 1]: $R_t$=1.11 min; MS (ESIpos): m/z=442 (M+H)$^+$ $^1$H-NMR (400 MHz, DMSO-d$_6$): δ [ppm]=7.84 (d, 1H), 7.72 (dd, 1H), 7.48 (d, 1H), 6.30 (s, 1H), 4.79 (dd, 2H), 3.07-3.02 (m, 2H), 2.59-2.55 (m, 2H), 1.44 (s, 9H).

Example 6.1E

{4-[5-Chloro-2-(trifluoromethyl)phenyl]-2,5-dioxo-2,5,6,7-tetrahydro-1H-cyclopenta[b]pyridin-1-yl}acetic acid

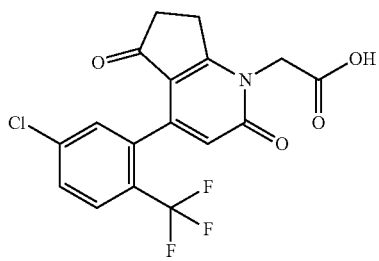 [SMILES: O=C(O)Cn1c2c(c(-c3cc(Cl)ccc3C(F)(F)F)cc1=O)C(=O)CC2]

605 mg (1.3 mmol) of tert-Butyl {4-[5-chloro-2-(trifluoromethyl)phenyl]-2,5-dioxo-2,5,6,7-tetrahydro-1H-cyclopenta[b]pyridin-1-yl}acetate were hydrolysed with TFA according to general method 2A. Yield: 690 mg (quant.)

LC-MS [Method 1]: $R_t$=0.79 min; MS (ESIpos): m/z=386 (M+H)$^+$.

Example 6.2A tert-Butyl 5-{4-[({4-[5-chloro-2-(trifluoromethyl)phenyl]-2,5-dioxo-2,5,6,7-tetrahydro-1H-cyclopenta[b]pyridin-1-yl}acetyl)amino]phenyl}-3-oxo-2,3-dihydro-1H-pyrazol-1-carboxylate

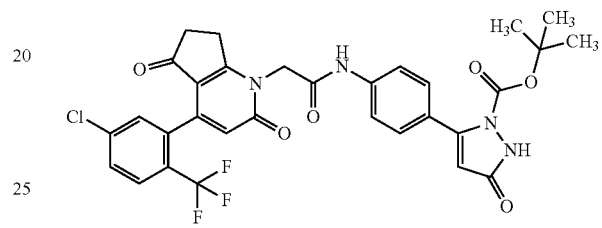

According to general method 1A, 100 mg (0.4 mmol) of {4-[5-chloro-2-(trifluoromethyl)phenyl]-2, 5-dioxo-2,5,6,7-tetrahydro-1H-cyclopenta[b]pyridin-1-yl}acetic acid were reacted with 83 mg (0.27 mmol, 1.1 eq.) of tert-butyl 5-(4-aminophenyl)-3-oxo-2,3-dihydro-1H-pyrazole-1-carboxylate. Yield: 36 mg (15% of theory, purity 64%)

LC-MS [Method 1]: $R_t$=1.14 min; MS (ESIpos): m/z=643 (M+H)$^+$.

Example 7.1A tert-Butyl (4-hydroxy-2,5-dioxo-2,5,6,7-tetrahydro-1H-cyclopenta[b]pyridin-1-yl)acetate

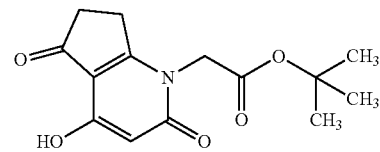 [SMILES: CC(C)(C)OC(=O)Cn1c2c(c(O)cc1=O)C(=O)CC2]

A solution of 1.5 g (7.1 mmol) of tert-butyl N-(3-oxocyclopent-1-en-1-yl)glycinate and 3.62 g (7.81 mmol) of bis (2,4,6-trichlorophenylmalonate) in 20 ml of diethylene glycol dimethyl ether was stirred at 100° C. for 3 h. The reaction mixture was cooled to room temperature and the solvent was removed under reduced pressure. The residue was triturated with 50 ml of diethyl ether, and the precipitate was filtered off under suction, washed with diethyl ether and dried under reduced pressure. Yield: 1.0 g (49% of theory, purity 89%)

LC-MS [Method 1]: $R_t$=0.86 min; MS (ESIpos): m/z=280 (M+H)$^+$.

$^1$H-NMR (400 MHz, DMSO-d$_6$): δ [ppm]=11.17 (br. s, 1H), 5.54 (s, 1H), 4.63 (s, 2H), 2.92-2.88 (m, 2H), 2.55-2.49 (m, 2H), 1.42 (s, 9H).

Example 7.1B tert-Butyl (2,5-dioxo-4-{[(trifluoromethyl)sulphonyl]oxy}-2,5,6,7-tetrahydro-1H-cyclopenta[b]pyridin-1-yl]acetate

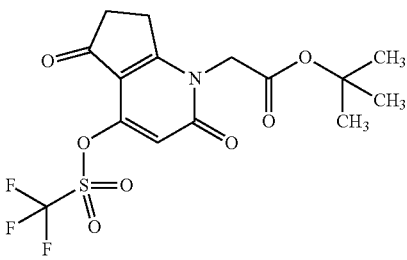 [SMILES: CC(C)(C)OC(=O)Cn1c2c(c(OS(=O)(=O)C(F)(F)F)cc1=O)C(=O)CC2]

At 0° C., 580 µl (4.18 mmol, 1.1 eq.) of triethylamine were added to a solution of 1.06 g (3.80 mmol) of tert-butyl (4-hydroxy-2,5-dioxo-2,5,6,7-tetrahydro-1H-cyclopenta[b]pyridin-1-yl]acetate in 21 ml of dichloromethane. Subsequently, 1.49 g (4.18 mmol, 1.1 eq.) of N,N-bis(trifluoromethanesulphonyl)aniline was added in portions. The mixture was stirred at room temperature for 2 d. The solvent was removed under reduced pressure and the residue was purified by MPLC (120 g, 30 µm cartridge, 50 ml/min, cyclohexane/ethyl acetate gradient: 10 min 100% cyclohexane, 15 mm 75% cyclohexane, 35 min 66% cyclohexane, 1 mm 50% cyclohexane, then isocratic). Yield: 950 mg (55% of theory, purity 90%)

LC-MS [Method 1]: $R_t$=1.03 min; MS (ESIpos): m/z=412 (M+H)$^+$ $^1$H-NMR (400 MHz, DMSO-d$_6$): δ [ppm]=6.64 (s, 1H), 4.76 (s, 2H), 3.10-3.07 (m, 2H), 2.73-2.69 (m, 2H), 1.43 (s, 9H).

Example 7.1C tert-Butyl [4-(5-chloro-2-cyanophenyl]-2,5-dioxo-2,5,6,7-tetrahydro-1H-cyclopenta[b]pyridin-1-yl]acetate

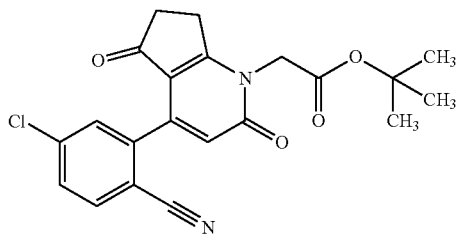 [SMILES: CC(C)(C)OC(=O)Cn1c2c(c(-c3cc(Cl)ccc3C#N)cc1=O)C(=O)CC2]

472 mg (1.15 mmol) of tert-Butyl (2,5-dioxo-4-{[trifluoromethyl)sulphonyl]oxy}-2,5,6,7-tetrahydro-1H-cyclopenta[b]pyridin-1-yl)acetate, 239 mg (1.32 mmol, 1.15 eq.) of 5-chloro-2-cyanophenylboronic acid, 478 mg (3.44 mmol, 3.0 eq.) of potassium carbonate and 133 mg (0.115 mmol, 0.1 eq.) of tetrakis(triphenylphosphine)palladium(0) were initially charged in a heat-dried flask flushed with argon, evacuated three times and flushed with argon. 15 ml of dioxane were added and the reaction mixture was stirred at 110° C. for 16 h. After cooling to RT, the reaction mixture was then filtered through Celite and the filtrate was concentrated under reduced pressure. The crude product was purified by MPLC (120 g, 30 µm cartridge, 50 ml/min, cyclohexane/ethyl acetate gradient: 10 min 100% cyclohexane, 15 min 75% cyclohexane, 35 min 66% cyclohexane, 1 min 50% cyclohexane, then 25 min isocratic). Yield: 236 mg (50% of theory).

LC-MS [Method 1]: $R_t$=1.00 min; MS(ESIneg): m/z=397 [M+H]$^+$ $^1$H-NMR (400 MHz, DMSO-d$_6$): δ [ppm]=7.97 (d, 1H), 7.74 (dd, 1H), 7.68 (d, 1H), 6.49 (s, 1H), 4.81 (s, 2H), 3.10-3.05 (m, 2H), 2.64-2.60 (m, 2H), 1.45 (s, 9H).

Example 7.1D

[4-(5-Chloro-2-cyanophenyl)-2,5-dioxo-2,5,6,7-tetrahydro-1H-cyclopenta[b]pyridin-1-yl]acetic acid

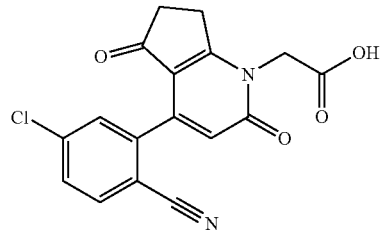 [SMILES: N#Cc1ccc(Cl)cc1-c1cc(=O)n(CC(=O)O)c2c1C(=O)CC2]

150 mg (380 µmol) of tert-Butyl [4-(5-chloro-2-cyanophenyl]-2,5-dioxo-2,5,6,7-tetrahydro-1H-cyclopenta[b]pyridin-1-yl]acetate were hydrolysed with TFA according to general method 2A. Yield: 120 mg (90% of theory)

LC-MS [Method 1]: $R_t$=0.65 min.; MS (ESIpos): m/z=343 (M+H)$^+$ $^1$H-NMR (400 MHz, DMSO-d$_6$): δ [ppm]=13.4 (br. s, 1H), 7.97 (d, 1H), 7.74 (dd, 1H), 7.69 (d, 1H), 6.49 (s, 1H), 4.82 (s, 2H), 3.13-3.07 (m, 2H), 2.64-2.59 (m, 2H).

Example 7.2A tert-Butyl 4-({[4-(5-chloro-2-cyanophenyl)-2,5-dioxo-2,5,6,7-tetrahydro-1H-cyclopenta[b]pyridin-1-yl]acetyl}amino)benzoate

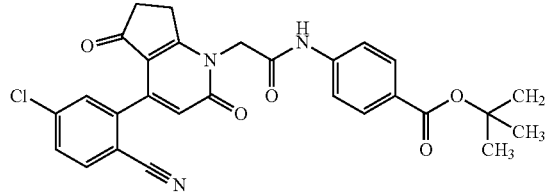 [SMILES: CC(C)(C)OC(=O)c1ccc(NC(=O)Cn2c3c(c(-c4cc(Cl)ccc4C#N)cc2=O)C(=O)CC3)cc1]

According to general method 1A, 90 mg (0.26 mmol) of [4-(5-chloro-2-cyanophenyl)-2,5-dioxo-2,5,6,7-tetrahydro-1H-cyclopenta[b]pyridin-1-yl]acetic acid were reacted with 61 mg (0.32 mmol, 1.2 eq.) of tert-butyl 4-aminobenzoate. Yield: 55 mg (40% of theory)

LC-MS [Method 1]: $R_t$=1.12 min.; MS (ESIneg): m/z=516 (M+H)$^-$ $^1$H-NMR (400 MHz, DMSO-d$_6$): δ [ppm]=10.88 (s, 1H), 7.98 (d, 1H), 7.89 (d, 2H), 7.76-7.68 (m, 4H), 6.49 (s, 1H), 4.97 (s, 2H), 3.17-3.12 (m, 2H), 2.65-2.60 (m, 2H), 1.54 (s, 9H).

Example 7.3A tert-Butyl 5-[4-({[4-(5-chloro-2-cyanophenyl)-2,5-dioxo-2,5,6,7-tetrahydro-1H-cyclopenta[b]pyridin-1-yl]acetyl}amino)phenyl]-3-oxo-2,3-dihydro-1H-pyrazole-1-carboxylate

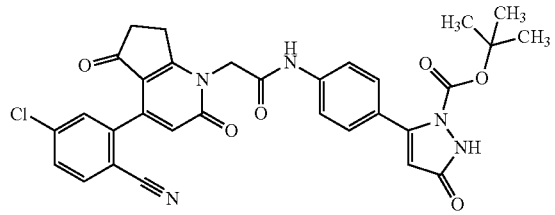 [SMILES: CC(C)(C)OC(=O)n1[nH]c(=O)cc1-c1ccc(NC(=O)Cn2c3c(c(-c4cc(Cl)ccc4C#N)cc2=O)C(=O)CC3)cc1]

118 mg (0.296 mmol, 86% pure) of [4-(5-chloro-2-cyanophenyl)-2,5-dioxo-2,5,6,7-tetrahydro-1H-cyclopenta[b]pyridin-1-yl]acetic acid were reacted with 112 mg (0.326 mmol, 1.2 eq., 80% pure) of tert-butyl 5-(4-aminophenyl)-3-oxo-2,3-dihydro-1H-pyrazole-1-carboxylate according to general method 1A. Yield: 100 mg (55% of theory).

LC-MS [Method 1]: $R_t$=1.04 min.; MS (ESIpos): m/z=600 (M+H)$^+$ $^1$H-NMR (400 MHz, DMSO-$d_6$): δ [ppm]=12.95 (d, 1H), 10.72 (s, 1H), 7.98 (d, 1H), 7.76-7.67 (m, 6H), 6.51-6.49 (m, 2H), 4.97 (s, 2H), 3.17-3.13 (m, 2H), 2.65-2.61 (m, 2H), 1.50 (s, 9H).

Example 7.4A tert-Butyl (4-hydroxy-2,5-dioxo-5,6,7,8-tetrahydroquinolin-1(2H)-yl)acetate

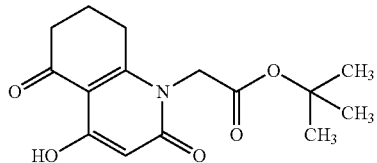 [SMILES: CC(C)(C)OC(=O)Cn1c2c(c(O)cc1=O)C(=O)CCC2]

A solution of 2.00 g (8.88 mmol) of tert-butyl (3-oxocyclohex-1-en-1-yl)glycinate and 4.52 g (9.77 mmol, 1.1 eq.) of bis(2,4,6-trichlorophenylmalonate) in 25 ml of diethylene glycol dimethyl ether was stirred at 100° C. for 5 h. The reaction mixture was cooled to room temperature and the solvent was removed under reduced pressure. The residue was dissolved in 8 ml of dichloromethane and purified by MPLC (120 g, 30 μm cartridge, 50 ml/min, cyclohexane/ethyl acetate gradient: 10 min 100% cyclohexane, 15 min 75% cyclohexane, 35 min 66% cyclohexane, 1 min 50% cyclohexane, then 25 min isocratic). Yield: 720 mg (27% of theory)

LC-MS [Method 1]: $R_t$=0.83 min; MS (ESIpos): m/z=294 (M+H)$^+$ $^1$H-NMR (400 MHz, DMSO-$d_6$): δ [ppm]=12.75 (br. s, 1H), 5.60 (s, 1H), 4.81 (s, 2H), 2.92-2.87 (m, 2H), 2.61-2.56 (m, 2H), 2.07-1.99 (m, 2H), 1.43 (s, 9H).

Beispiel 7.4B tert-Butyl [2,5-dioxo-4-{[(trifluoromethyl)sulphonyl]oxy}-5,6,7,8-tetrahydroquinolin-1(2H)-yl]acetate

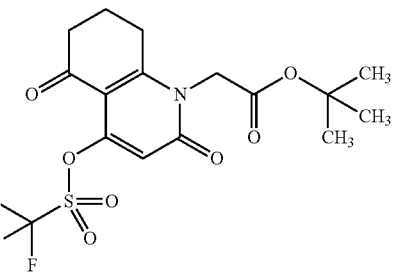

At 0° C., 375 μl (2.70 mmol, 1.1 eq.) of triethylamine were added to a solution of 717 mg (2.44 mmol) of tert-butyl (4-hydroxy-2,5-dioxo-5, 6,7,8-tetrahydroquinolin-1(2Hyl] acetate in 14 ml of dichloromethane. Subsequently, 961 mg (2.70 mmol, 1.1 eq.) of N,N-bis(trifluoromethanesulphonyl) aniline were added in portions and stirred at 60° C. for 6 d. After cooling to RT, the solvent was removed under reduced pressure and the residue was purified by MPLC (120 g, 30 μm cartridge, 50 ml/min, cyclohexane/ethyl acetate gradient: 10 min 100% cyclohexane, 15 min 75% cyclohexane, 35 min 66% cyclohexane, 1 min 50% cyclohexane, then isocratic). Yield: 128 mg (12% of theory)

LC-MS [Method 1]: $R_t$=1.07 min; MS(ESIneg): m/z=424 [M+H]±

$^1$H NMR (400 MHz, DMSO-$d_6$) δ=6.55 (s, 2H), 4.86 (s, 3H), 2.99 (s, 2H), 2.54-2.45 (m, 2H), 2.06-1.98 (m, 2H) (characteristic signals of the main component).

Example 7.4C tert-Butyl [4-(5-chloro-2-cyanophenyl)-2,5-dioxo-5,6,7,8-tetrahydroquinolin-1(2H)-yl]acetate

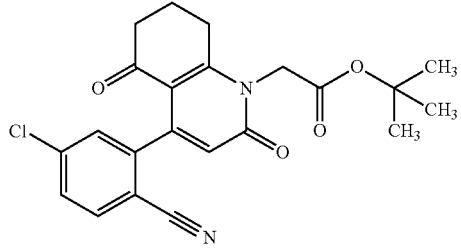 [SMILES: CC(C)(C)OC(=O)Cn1c2c(c(-c3cc(Cl)ccc3C#N)cc1=O)C(=O)CCC2]

125 mg (0.29 mmol) of tert-butyl [2,5-dioxo-4-{[(trifluoromethyl)sulphonyl]oxy}-5,6,7,8-tetrahydroquinolin-1 (2H)-yl]acetate, 61.3 mg (0.34 mmol, 1.15 eq.) of 5-chloro-2-cyanophenylboronic acid, 122 mg (0.88 mmol, 3.0 eq.) of potassium carbonate and 33.9 mg (0.029 mmol, 0.1 eq.) of tetrakis(triphenylphosphine)palladium(0) were initially charged in a heat-dried flask flushed with argon, evacuated three times and flushed with argon. 15 ml of dioxane were added and the reaction mixture was stirred at 110° C. for 16 h. After cooling to RT, the reaction mixture was then filtered through Celite and the filtrate was concentrated under reduced pressure. The crude product was purified by means of prep. HPLC (column: Chromatorex C18. 10 µm, 125*30 mm, acetonitrile/water+0.05% formic acid gradient: 0-3 min 10% acetonitrile, to 35 min 90% acetonitrile and a further 3 min 90% acetonitrile). Yield: 45 mg (37% of theory)

LC-MS [Method 1]: $R_t$=1.05 min.; MS (ESIneg): m/z=411 (M+H)⁻

¹H-NMR (400 MHz, DMSO-$d_6$): δ [ppm]=7.88 (d, 1H), 7.63 (dd, 1H), 7.55 (d, 1H), 6.36 (s, 1H), 4.91 (d, 2H), 3.06-2.88 (m, 2H), 2.44-2.37 (m, 2H), 2.12-1.96 (m, 2H), 1.45 (s, 9H).

Example 7.4D

[4-(5-chloro-2-cyanophenyl)-2,5-dioxo-5,6,7,8-tetrahydroquinolin-1(2H)-yl]acetic acid

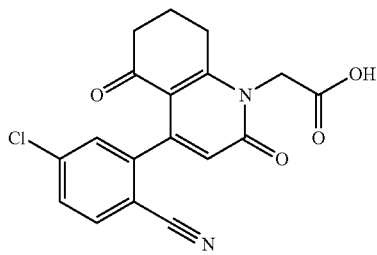 [SMILES: N#Cc1ccc(Cl)cc1-c1cc(=O)n(CC(=O)O)c2c1C(=O)CCC2]

44.0 mg (107 µmol) of tert-butyl [4-(5-chloro-2-cyanophenyl)-2,5-dioxo-5,6,7,8-tetrahydroquinolin-1(2H)-yl]acetate were hydrolysed with TFA according to general method 2A. Yield: 38 mg (quant.)

LC-MS [Method 3]: $R_t$=1.67 min.; MS (ESIpos): m/z=357 (M+H)⁺

¹H-NMR (400 MHz, DMSO-$d_6$): δ [ppm]=13.39 (br. s, 1H), 7.88 (d, 1H), 7.63 (dd, 1H), 7.56 (d, 1H), 6.36 (s, 1H), 4.97-4.86 (m, 2H), 3.10-2.89 (m, 2H), 2.44-2.39 (m, 2H), 2.10-1.97 (m, 2H).

Example 7.5A tert-Butyl 4-({[4-(5-chloro-2-cyanophenyl)-2,5-dioxo-5,6,7,8-tetrahydroquinolin-1(2H)-yl]acetyl}amino)benzoate

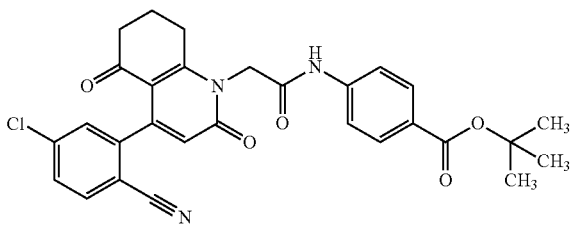 [SMILES: CC(C)(C)OC(=O)c1ccc(NC(=O)Cn2c3c(c(-c4cc(Cl)ccc4C#N)cc2=O)C(=O)CCC3)cc1]

According to general method 1A, 40.0 mg (0.112 mmol) of [4-(5-chloro-2-cyanophenyl)-2,5-dioxo-5,6,7,8-tetrahydroquinolin-1(2H)-yl]acetic acid were reacted with 26.0 mg (0.135 mmol, 1.2 eq.) of tert-butyl 4-aminobenzoate. Yield: 16 mg (26% of theory)

LC-MS [Method 3]: $R_t$=2.46 min.; MS (ESIneg): m/z=531 (M−H)⁻

¹H-NMR (400 MHz, DMSO-$d_6$): δ [ppm]=10.86 (s, 1H), 7.89 (d, 1H), 7.88 (d, 2H), 7.72 (d, 2H), 7.64 (dd, 1H), 7.56 (d, 1H), 6.37 (s, 1H), 5.07 (q, 2H), 3.16-2.95 (m, 2H), 2.45-2.38 (m, 2H), 2.10-1.99 (m, 2H), 1.54 (s, 9H).

WORKING EXAMPLES

General Method 1

Amide Coupling with Carboxylic Acids

Under argon and at RT, the appropriate amine (1.1 eq.), N,N-diisopropylethylamine (2.2 eq.) and a solution of HATU (1.2 eq.) in a little DMF were added to a solution of the appropriate carboxylic acid (1.0 eq.) in dimethylformamide (about 12 ml/mmol). The reaction mixture was stirred at RT. After addition of water/ethyl acetate and phase separation, the organic phase was washed with water and with saturated aqueous sodium chloride solution, dried (sodium sulphate), filtered and concentrated under reduced pressure. The crude product was then purified by preparative HPLC (Reprosil C18, water/acetonitrile gradient or water/methanol gradient).

General Method 2

Hydrolysis of a Tert-Butyl Ester or a Boc-protected Amine Using TFA

At RT, TFA (20 eq.) was added to a solution of the appropriate tert-butyl ester derivative or a Boc-protected amine (1.0 eq.) in dichloromethane (about 25 ml/mmol), and the mixture was stirred at RT for 1-8 h. Subsequently, the reaction mixture was concentrated under reduced pressure. The residue was coevaporated three times with dichloromethane. The crude product was then purified by preparative RP-HPLC (mobile phase: acetonitrile/water gradient or water/methanol gradient).

General Method 3

Hydrolysis of a Methyl or Ethyl Ester

At RT, lithium hydroxide (2-4 eq.) was added to a solution of the appropriate methyl or ethyl ester (1.0 eq.) in a mixture of tetrahydrofuran/water (3:1, about 15 ml/mmol), and the mixture was stirred at RT. The reaction mixture was then adjusted to pH 1 using aqueous hydrochloric acid solution (1N). After addition of water/ethyl acetate, the aqueous phase was extracted three times with ethyl acetate. The combined organic phases were dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

Example 1

2-[4-(3-Chlorophenyl)-2,5-dioxo-2,5,6,7-tetrahydro-1H-pyrrolo[3,4-b]pyridin-1-yl]-N-[4-(1H-tetrazol-5-yl)phenyl]acetamide

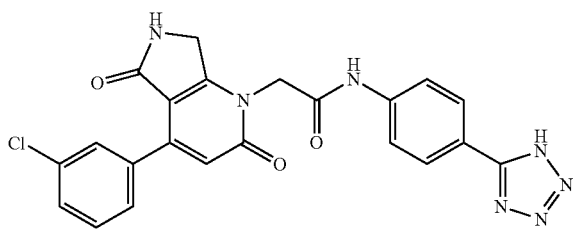 [SMILES: O=C(Cn1c2c(c(-c3cccc(Cl)c3)cc1=O)C(=O)NC2)Nc1ccc(-c2nnn[nH]2)cc1]

A solution of 369 mg (0.67 mmol, 4.0 eq.) of ammonium cerium(IV) nitrate in 0.7 ml of water was added to a solution of 78 mg (0.17 mmol) of 2-[4-(3-chlorophenyl)-2,5-dioxo-2,3,4,5,6,7-hexahydro-1H-pyrrolo[3,4-b]pyridin-1-yl]-N-[4-(1H-tetrazol-5-yl)phenyl]acetamide (racemate) in 2.7 ml of acetone and the mixture was stirred at RT overnight. The reaction mixture was then added to water, the precipitate filtered off and dried under vacuum. The crude product was purified by preparative HPLC (Sunfire C 18 5 μm, water-methanol gradient). Yield: 32 mg (41% of theory)

LC-MS [Method 4]: $R_t$=0.86 min; MS (ESIpos): m/z=462 (M+H)$^+$ $^1$H-NMR (400 MHz, DMSO-d$_6$): δ [ppm]=10.81 (s, 1H), 8.32 (s, 1H), 8.00 (d, 2H), 7.79 (d, 2H), 7.65 (s, 1H), 7.56-7.44 (m, 3H), 6.42 (s, 1H), 4.86 (s, 2H), 4.39 (s, 2H).

Example 2

2-[4-(2,5-Dichlorophenyl)-6-methyl-2,5-dioxo-2,5,6,7-tetrahydro-1H-pyrrolo[3,4-b]pyridin-1-yl]-N-[4-(1H-tetrazol-5-yl)phenyl]acetamide

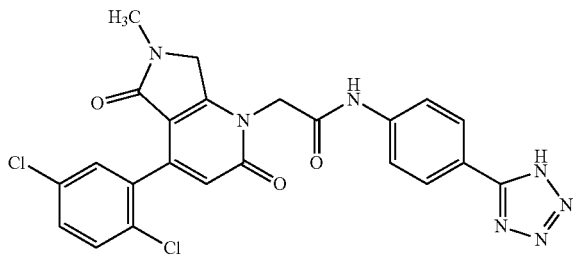 [SMILES: CN1Cc2c(c(-c3cc(Cl)ccc3Cl)cc(=O)n2CC(=O)Nc2ccc(-c3nnn[nH]3)cc2)C1=O]

According to general method 1, 105 mg (0.16 mmol, 56% pure) of [4-(2,5-dichlorophenyl)-6-methyl-2,5-dioxo-2,5,6,7-tetrahydro-1H-pyrrolo[3,4-b]pyridin-1-yl]acetic acid were reacted with 28 mg (0.18 mmol, 1.1 eq.) of 4-(1H-tetrazol-5-yl)aniline. Yield: 12 mg (14% of theory)

LC-MS [Method 1]: $R_t$=0.79 min; MS(ESIneg): m/z=510 [M+H]$^+$ $^1$H-NMR (400 MHz, DMSO-d$_6$): δ [ppm]=10.87 (s, 1H), 8.02 (d, 2H), 7.82 (d, 2H), 7.57 (d, 1H), 7.53 (dd, 1H), 7.47 (d, 1H), 6.37 (s, 1H), 4.89 (s, 2H), 4.50 (s, 2H), 2.92 (s, 3H).

Example 3

2-[4-(2,5-Dichlorophenyl)-2,5-dioxo-2,5,6,7-tetrahydro-1H-cyclopenta[b]pyridin-1-yl]-N-[4-(1H-tetrazol-5-yl)phenyl]acetamide

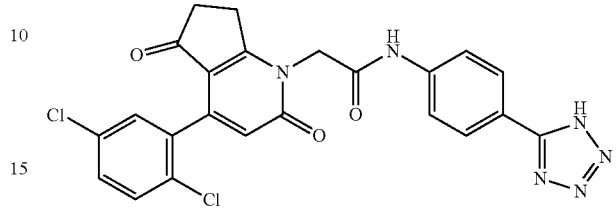

A solution of 443 mg (0.8 mmol) of ammonium cerium (IV) nitrate in 0.8 ml of water was added to a solution of 113 mg (0.2 mmol, 89% pure) of 2-[4-(2,5-dichlorophenyl)-2,5-dioxo-2,3,4,5,6,7-hexahydro-1H-cyclopenta[b]pyridin-1-yl]-N-[4-(1H-tetrazol-5-yl)phenyl]acetamide (racemate) in 3 ml of acetone and the mixture was stirred at RT overnight and then concentrated under reduced pressure. After addition of water/ethyl acetate and phase separation, the organic phase was washed with water and with saturated aqueous sodium chloride solution, dried (sodium sulphate), filtered and concentrated under reduced pressure. The crude product was purified by preparative HPLC (Kromasil 100 C18, acetonitrile/water+2% formic acid). Yield: 8 mg (8% of theory)

LC-MS [Method 1]: $R_t$=0.87 min; MS(ESIneg): m/z=495 [M+H]$^+$ $^1$H-NMR (400 MHz, DMSO-d$_6$): δ [ppm]=16.77 (br. s, 1H), 10.88 (s, 1H), 8.02 (d, 2H), 7.83 (d, 2H), 7.56 (s, 1H), 7.54 (d, 1H), 7.45 (d, 1H), 6.34 (s, 1H), 4.97 (s, 2H), 3.19-3.05 (m, 2H), 2.68-2.55 (m, 2H).

Example 4

4-({[4-(2,5-Dichlorophenyl)-2,5-dioxo-2,5,6,7-tetrahydro-1H-cyclopenta[b]pyridin-1-yl]acetyl}amino)benzoic acid

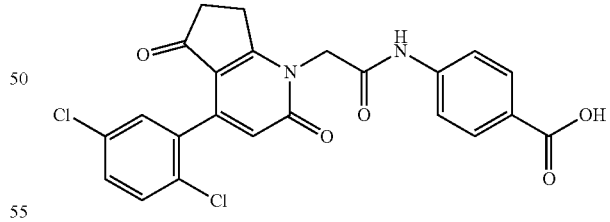

43 mg (0.08 mmol, 94% pure) of tert-butyl 4-({[4-(2,5-dichlorophenyl)-2,5-dioxo-2,5,6,7-tetrahydro-1H-cyclopenta[b]pyridin-1-yl]acetyl}amino)benzoate were hydrolysed with TFA according to general method 2. Yield: 39 mg (99% of theory, purity 92%)

LC-MS [Method 1]: $R_t$=0.86 min; MS(ESIneg): m/z=471 [M+H]$^+$ $^1$H-NMR (400 MHz, DMSO-d$_6$): δ [ppm]=10.87 (s, 1H), 7.93 (d, 2H), 7.72 (d, 2H), 7.57 (d, 1H), 7.52 (dd, 1H), 7.45 (d, 1H), 6.33 (s, 1H), 4.96 (s, 2H), 3.15-3.07 (br. s, 2H), 2.63-2. (br. s, 2H).

Example 5

2-[4-(2,5-Dichlorophenyl)-2,5-dioxo-2,5,6,7-tetrahydro-1H-cyclopenta[b]pyridin-1-yl]-N-[4-(5-oxo-4,5-dihydro-1,2,4-oxadiazol-3-yl)phenyl]acetamide

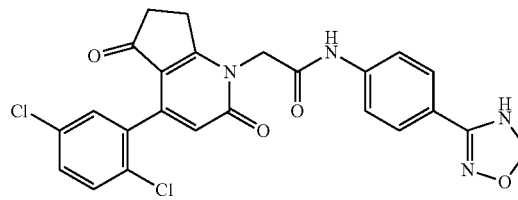

According to general method 1, 120 mg (0.29 mmol, 86% pure) of [4-(2,5-dichlorophenyl)-2,5-dioxo-2,5,6,7-tetrahydro-1H-cyclopenta[b]pyridin-1-yl]acetic acid were reacted with 57 mg (0.32 mmol) of 3-(4-aminophenyl)-1,2,4-oxadiazol-5(4H)-one. Yield: 14 mg (9% of theory)

LC-MS [Method 1]: $R_t$=0.91 min; MS (ESIpos): m/z=511 (M+H)$^+$ $^1$H-NMR (400 MHz, DMSO-d$_6$): δ [ppm]=10.76 (s, 1H), 7.76 (d, 2H), 7.70 (d, 2H), 7.56 (d, 1H), 7.51 (dd, 1H), 7.44 (d, 1H), 6.33 (s, 1H), 4.95 (s, 2H), 3.15-3.07 (br. s, 2H), 2.63-2.55 (br. s, 2H).

Example 6

2-[4-(2,5-Dichlorophenyl)-2,5-dioxo-2,5,6,7-tetrahydro-1H-cyclopenta[b]pyridin-1-yl]-N-{4-[3-(trifluoromethyl)-1H-1,2,4-triazol-5-yl]phenyl}acetamide

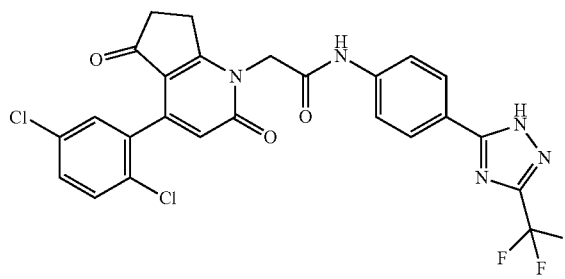

According to general method 1, 120 mg (0.29 mmol, 86% pure) of [4-(2,5-dichlorophenyl)-2,5-dioxo-2,5,6,7-tetrahydro-1H-cyclopenta[b]pyridin-1-yl]acetic acid were reacted with 77 mg (0.32 mmol, 1.1 eq.) of 4-[3-(trifluoromethyl)-1H-1,2,4-triazol-5-yl]aniline. Yield: 35 mg (21% of theory)

LC-MS [Method 1]: $R_t$=1.05 min; MS (ESIpos): m/z=562 (M+H)$^+$ $^1$H-NMR (400 MHz, DMSO-d$_6$): δ [ppm]=15.18 (s, 1H), 10.85 (s, 1H), 8.01 (d, 2H), 7.80 (d, 2H), 7.55 (d, 1H), 7.53 (dd, 1H), 7.44 (d, 1H), 6.33 (s, 1H), 4.97 (s, 2H), 3.16-3.08 (br. s, 2H), 2.64-2.56 (br. s, 2H).

Example 7

2-[4-(2,5-Dichlorophenyl)-2,5-dioxo-2,5,6,7-tetrahydro-1H-cyclopenta[b]pyridin-1-yl]-N-[4-(5-oxo-2,5-dihydro-1H-pyrazol-3-yl)phenyl]acetamide

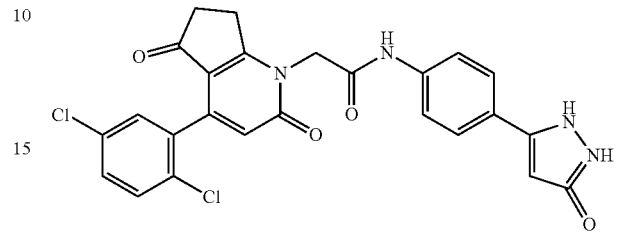

53 mg (0.09 mmol) of tert-butyl 5-[4-({[4-(2,5-dichlorophenyl)-2,5-dioxo-2,5,6,7-tetrahydro-1H-cyclopenta[b]pyridin-1-yl]acetyl}amino)phenyl]-3-oxo-2,3-dihydro-1H-pyrazole-1-carboxylate were hydrolysed with TFA according to general method 2. Yield: 5 mg (11% of theory)

LC-MS [Method 1]: $R_t$=0.86 min; MS (ESIpos): m/z=509 (M+H)$^+$ $^1$H-NMR (400 MHz, DMSO-d$_6$): δ [ppm]=11.98 (s, 1H), 10.65 (s, 1H), 9.57 (s, 1H), 7.63 (br. s, 4H), 7.57 (d, 1H), 7.52 (dd, 1H), 7.45 (d, 1H), 6.33 (s, 1H), 5.85 (br. s, 1H), 4.96 (s, 2H), 3.16-3.04 (br. s, 2H), 2.63-2.55 (br. s, 2H).

Example 8

2-[4-(2,5-Dichlorophenyl)-2,5-dioxo-2,5,6,7-tetrahydro-1H-cyclopenta[b]pyridin-1-yl]-N-[4-(1H-imidazol-5-yl)phenyl]acetamide

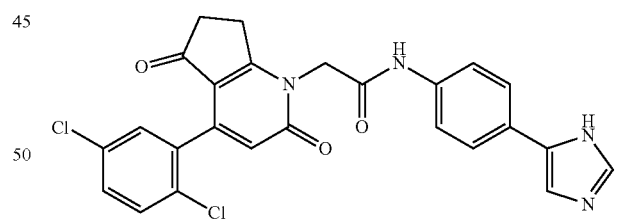

According to general method 1, 102 mg (0.25 mmol, 86% pure) of [4-(2,5-dichlorophenyl)-2,5-dioxo-2,5,6,7-tetrahydro-1H-cyclopenta[b]pyridin-1-yl]acetic acid were reacted with 44 mg (0.28 mmol, 1.1 eq.) of 4-(1H-imidazol-5-yl)aniline. Yield: 23 mg (18% of theory)

LC-MS [Method 1]: $R_t$=0.75 min; MS (ESIpos): m/z=493 (M+H)$^+$ $^1$H-NMR (400 MHz, DMSO-d$_6$): δ [ppm]=10.58 (s, 1H), 7.90 (br. s, 1H), 7.73 (d, 2H), 7.62 (d, 2H), 7.59-7.55 (m, 2H), 7.53 (dd, 1H), 7.44 (d, 1H), 6.33 (s, 1H), 4.94 (s, 2H), 3.12 (br. s, 2H), 2.60 (br. s, 2H).

Example 9

2-[4-(2-Bromo-5-chlorophenyl)-2,5-dioxo-2,5,6,7-tetrahydro-1H-cyclopenta[b]pyridin-1-yl]-N-[4-(1H-tetrazol-5-yl)phenyl]acetamide

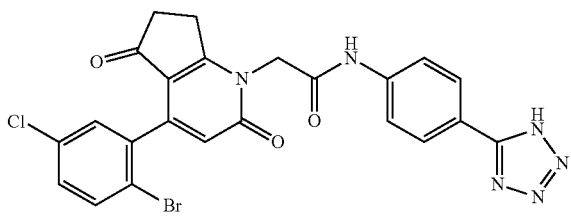 [SMILES: O=C(Cn1c2c(c(-c3cc(Cl)ccc3Cl)cc1=O)C(=O)CC2)Nc1ccc(-c2nnn[nH]2)cc1]

According to general method 1, 89 mg (0.21 mmol, 93% pure) of [4-(2-bromo-5-chlorophenyl)-2,5-dioxo-2,5,6,7-tetrahydro-1H-cyclopenta[b]pyridin-1-yl]acetic acid were reacted with 37 mg (0.23 mmol, 1.1 eq.) of 4-(1H-tetrazol-5-yl)aniline. Yield: 28 mg (25% of theory)

LC-MS [Method 1]: $R_t$=0.83 min; MS (ESIpos): m/z=539 (M+H)$^+$ $^1$H-NMR (400 MHz, DMSO-d$_6$): δ [ppm]=10.88 (s, 1H), 8.02 (d, 2H), 7.83 (d, 2H), 7.72 (d, 1H), 7.44 (dd, 1H), 7.41 (d, 1H), 6.30 (s, 1H), 4.97 (s, 2H), 3.17-3.09 (br. s, 2H), 2.63-2.56 (br. s, 2H).

Example 10

2-[4-(2-Bromo-5-chlorophenyl)-2,5-dioxo-2,5,6,7-tetrahydro-1H-cyclopenta[b]pyridin-1-yl]-N-[4-(5-oxo-4,5-dihydro-1,2,4-oxadiazol-3-yl)phenyl]acetamide

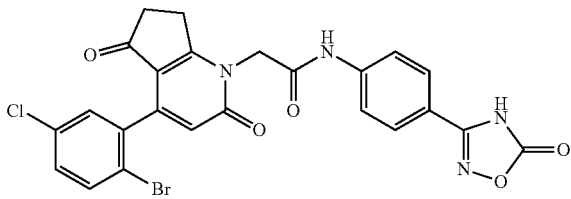 [SMILES: O=C(Cn1c2c(c(-c3cc(Cl)ccc3Br)cc1=O)C(=O)CC2)Nc1ccc(-c2noc(=O)[nH]2)cc1]

According to general method 1, 90 mg (0.21 mmol, 94% pure) of [4-(2-bromo-5-chlorophenyl)-2,5-dioxo-2,5,6,7-tetrahydro-1H-cyclopenta[b]pyridin-1-yl]acetic acid were reacted with 45 mg (0.26 mmol, 1.2 eq.) of 3-(4-aminophenyl)-1,2,4-oxadiazol-5(4H)-one. Yield: 43 mg (36% of theory)

LC-MS [Method 1]: $R_t$=0.92 min; MS (ESIpos): m/z=555 (M+H)$^+$ $^1$H-NMR (400 MHz, DMSO-d$_6$): δ [ppm]=12.86 (s, 1H), 10.90 (s, 1H), 7.79 (s, 4H), 7.72 (d, 1H), 7.44 (dd, 1H), 7.40 (d, 1H), 6.29 (s, 1H), 4.97 (s, 2H), 3.15-3.08 (br. s, 2H), 2.62-2.56 (br. s, 2H).

Example 11

2-{4-[5-Chloro-2-(trifluoromethyl)phenyl]-2,5-dioxo-2,5,6,7-tetrahydro-1H-cyclopenta[b]pyridin-1-yl}-N-[4-(5-oxo-2,5-dihydro-1H-pyrazol-3-yl)phenyl]acetamide

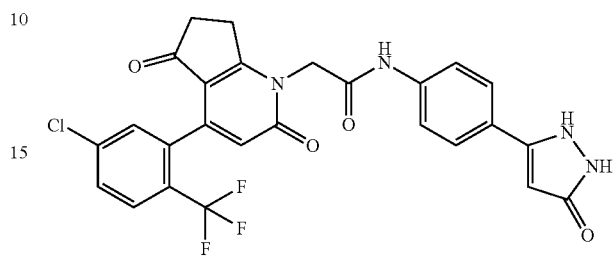

35 mg (0.04 mmol, 64% pure) of tert-butyl 5-{4-[({4-[5-chloro-2-(trifluoromethyl)phenyl]-2,5-dioxo-2,5,6,7-tetrahydro-1H-cyclopenta[b]pyridin-1-yl}acetyl)amino]phenyl}-3-oxo-2,3-dihydro-1H-pyrazole-1-carboxylate were hydrolysed with TFA according to general method 2. Yield: 34 mg (quant.)

LC-MS [Method 1]: $R_t$=0.89 min; MS (ESIpos): m/z=543 (M+H)$^+$ $^1$H-NMR (400 MHz, DMSO-d$_6$): δ [ppm]=11.98 (s, 1H), 10.65 (s, 1H), 9.57 (s, 1H), 7.85 (d, 1H), 7.74 (dd, 1H), 7.64 (br. s, 4H), 7.49 (d, 1H), 6.30 (s, 1H), 5.85 (br. s, 1H), 4.96 (q, 2H), 3.15-3.08 (m, 2H), 2.60-2.56 (m, 2H).

Example 12

4-({[4-(5-Chloro-2-cyanophenyl)-2,5-dioxo-2,5,6,7-tetrahydro-1H-cyclopenta[b]pyridin-1-yl]acetyl}amino)benzoic acid

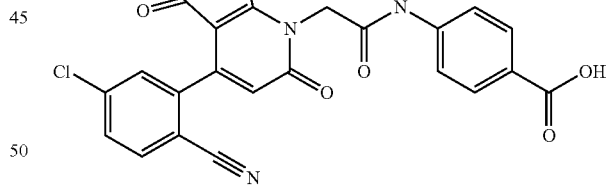

54 mg (0.10 mmol) of tert-butyl 4-({[4-(5-chloro-2-cyanophenyl)-2,5-dioxo-2,5,6,7-tetrahydro-1H-cyclopenta[b]pyridin-1-yl]acetyl}amino)benzoate were hydrolysed with TFA according to general method 2 and purified by preparative HPLC (column: Chromatorex C18, 10 μm, 125 mm×30 mm, acetonitrile/water gradient: 0-3 min 10% acetonitrile, to 35 min 90% acetonitrile and a further 3 min 90% acetonitrile). Yield: 27 mg (55% of theory)

LC-MS [Method 1]: $R_t$=0.80 min; MS (ESIpos): m/z=461 (M+H)$^+$ $^1$H-NMR (400 MHz, DMSO-d$_6$): δ [ppm]=12.77 (br. s, 1H), 10.87 (s, 1H), 7.98 (d, 1H), 7.92 (d, 2H), 7.77-7.68 (m, 4H), 6.50 (s, 1H), 4.98 (s, 2H), 3.17-3.12 (m, 2H), 2.66-2.60 (m, 2H).

Example 13

2-[4-(5-Chloro-2-cyanophenyl)-2,5-dioxo-2,5,6,7-tetrahydro-1H-cyclopenta[b]pyridin-1-yl]-N-[4-(5-oxo-4,5-dihydro-1,2,4-oxadiazol-3-yl)phenyl]acetamide

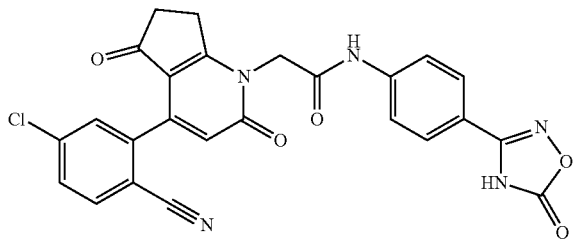 [SMILES: N#Cc1ccc(Cl)cc1-c1cc(=O)n(CC(=O)Nc2ccc(-c3noc(=O)[nH]3)cc2)c2c1C(=O)CC2]

According to general method 1, 90 mg (0.26 mmol) of [4-(5-chloro-2-cyanophenyl)-2,5-dioxo-2,5,6,7-tetrahydro-1H-cyclopenta[b]pyridin-1-yl]acetic acid were reacted with 56 mg (0.32 mmol, 1.2 eq.) of 3-(4-aminophenyl)-1,2,4-oxadiazol-5(4H)-one and purified by preparative HPLC (column: Chromatorex C18, 10 μm, 125 mm×30 mm, acetonitrile/water gradient: 0-3 min 10% acetonitrile, to 35 min 90% acetonitrile and a further 3 min 90% acetonitrile). Yield: 34 mg (25% of theory)

LC-MS [Method 1]: $R_t$=0.82 min; MS (ESIpos): m/z=502 (M+H)$^+$ $^1$H-NMR (400 MHz, DMSO-d$_6$): δ [ppm]=12.87 (br. s, 1H), 10.92 (s, 1H), 7.98 (d, 1H), 7.80 (br. s, 4H), 7.74 (dd, 1H), 7.68 (d, 1H), 6.49 (s, 1H), 4.98 (br. s, 2H), 3.17-3.12 (m, 2H), 2.65-2.61 (m, 2H).

Example 14

2-[4-(5-Chloro-2-cyanophenyl)-2,5-dioxo-2,5,6,7-tetrahydro-1H-cyclopenta[b]pyridin-1-yl]-N-[4-(5-oxo-2,5-dihydro-1H-pyrazol-3-yl)phenyl]acetamide

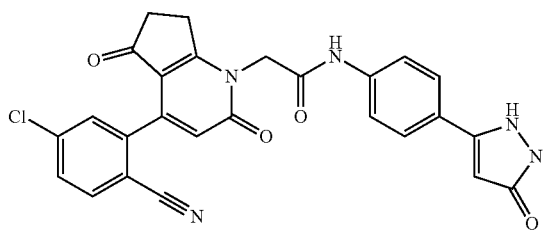 [SMILES: N#Cc1ccc(Cl)cc1-c1cc(=O)n(CC(=O)Nc2ccc(-c3noc(=O)[nH]3)cc2)c2c1C(=O)CC2]

93 mg (0.16 mmol) of tert-butyl 5-[4-({[4-(5-chloro-2-cyanophenyl)-2,5-dioxo-2,5,6,7-tetrahydro-1H-cyclopenta[b]pyridin-1-yl]acetyl}amino)phenyl]-3-oxo-2,3-dihydro-1H-pyrazole-1-carboxylate were hydrolysed with TFA according to general method 2 and purified by preparative HPLC (column: Chromatorex C18, 10 μm, 125 mm×30 mm, acetonitrile/water gradient: 0-3 min 10% acetonitrile, to 35 min 90% acetonitrile and a further 3 min 90% acetonitrile). Yield: 71 mg (90% of theory)

LC-MS [Method 1]: $R_t$=0.73 min; MS (ESIpos): m/z=500 (M+H)$^+$ $^1$H-NMR (400 MHz, DMSO-d$_6$): δ [ppm]=10.57 (br. s, 1H), 7.98 (d, 1H), 7.74 (dd, 1H), 7.70 (d, 1H), 7.52 (br. s, 4H), 6.49 (s, 1H), 4.96 (br. s, 3H), 3.18-3.12 (m, 2H), 2.65-2.60 (m, 2H). 2 NH-resonances not visible.

Example 15

4-({[4-(5-Chloro-2-cyanophenyl)-2,5-dioxo-5,6,7,8-tetrahydroquinolin-1(2H)-yl]acetyl}amino)benzoic acid

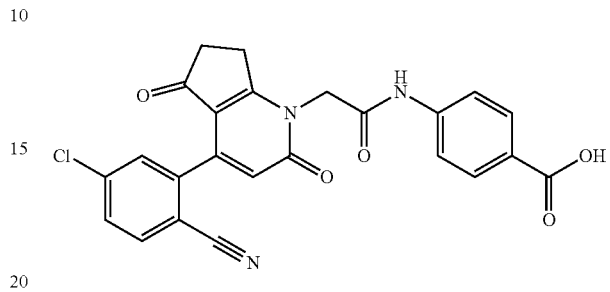

15 mg (0.03 mmol) of tert-butyl 4-({[4-(5-chloro-2-cyanophenyl)-2,5-dioxo-5,6,7,8-tetrahydroquinolin-1(2H)-yl]acetyl}amino)benzoate were hydrolysed with TFA according to general method 2 and purified by preparative HPLC (column: Kromasil, C18, 5 μm, 250 mm×20 mm, acetonitrile/water+0.05% formic acid gradient: 0-3 min 10% acetonitrile, to 33 min 90% acetonitrile and a further 8 min 90% acetonitrile). Yield: 5.6 mg (41% of theory)

LC-MS [Method 1]: $R_t$=0.83 min; MS (ESIneg): m/z=474 (M+H)$^-$ $^1$H-NMR (400 MHz, DMSO-d$_6$): δ [ppm]=12.78 (br. s, 1H), 10.83 (s, 1H), 7.92 (d, 2H), 7.89 (d, 1H), 7.71 (d, 2H), 7.63 (dd, 1H), 7.56 (d, 1H), 6.37 (s, 1H), 5.08 (q, 2H), 3.15-2.94 (m, 2H), 2.45-2.35 (m, 2H), 2.05-2.00 (m, 2H).

Example 16

2-[4-(5-Chloro-2-cyanophenyl)-2,5-dioxo-5,6,7,8-tetrahydroquinolin-1(2H)-yl]-N-[4-(5-oxo-4,5-dihydro-1,2,4-oxadiazol-3-yl)phenyl]acetamide

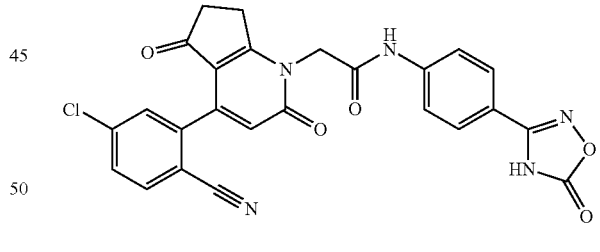

According to general method 1, 28 mg (0.08 mmol) of [4-(5-chloro-2-cyanophenyl)-2,5-dioxo-5,6,7,8-tetrahydroquinolin-1(2H)-yl]acetic acid were reacted with 17 mg (0.09 mmol, 1.2 eq.) of 3-(4-aminophenyl)-1,2,4-oxadiazol-5(4H)-one and purified by preparative HPLC (column: Chromatorex C18, 10 μm, 125 mm×30 mm, acetonitrile/water gradient: 0-3 min 10% acetonitrile, to 35 min 90% acetonitrile and a further 3 min 90% acetonitrile). Yield: 18 mg (45% of theory)

LC-MS [Method 1]: $R_t$=0.88 min; MS(ESIneg): m/z=516 [M+H]$^+$ $^1$H-NMR (400 MHz, DMSO-$d_6$): δ [ppm]=12.88 (br. s., 1H), 10.91 (br. s., 1H), 7.79-7.64 (m, 4H), 7.56 (d, 1H), 6.37-5.09 (m, 1H), 3.15-2.95 (m, 2H), 2.46 (d, 3H), three protons obscured.

B) Assessment of Physiological Efficacy

The suitability of the compounds according to the invention for treating thromboembolic disorders can be demonstrated in the following assay systems:

a) Test Descriptions (In Vitro)

a.1) Measurement of FXIa Inhibition

The factor XIa inhibition of the inventive substances is determined using a biochemical test system which utilizes the reaction of a peptidic factor XIa substrate to determine the enzymatic activity of human factor XIa. Here, factor XIa cleaves from the peptic factor XIa substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 µM to 0.0078 µM; resulting final concentrations in the test: 50 µM to 0.00013 µM). In each case 1 µl of the diluted substance solutions is placed into the wells of white microtitre plates from Greiner (384 wells). 20 µl of assay buffer (50 mM of Tris/HCl pH 7.4; 100 mM of sodium chloride solution; 5 mM of calcium chloride solution; 0.1% of bovine serum albumin) and 20 µl of factor XIa from Kordia (0.45 nM in assay buffer) are then added successively. After 15 mM of incubation, the enzyme reaction is started by addition of 20 µl of the factor XIa substrate Boc-Glu(OBzl)-Ala-Arg-AMC dissolved in assay buffer (10 µM in assay buffer) from Bachem, the mixture is incubated at room temperature (22° C.) for 30 mM and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships. Activity data from this test are listed in Table A below:

TABLE A

| Example No. | $IC_{50}$ [nM] | Example No. | $IC_{50}$ [nM] |
|---|---|---|---|
| 1 | 930 | 2 | 340 |
| 3 | 230 | 4 | 420 |
| 5 | 330 | 6 | 550 |
| 7 | 130 | 8 | 470 |
| 9 | 170 | 10 | 190 |
| 11 | 750 | 12 | 60 |
| 13 | 34 | 14 | 140 |
| 15 | 98 | 16 | 77 | a.2) Determination of the Selectivity

To demonstrate the selectivity of the substances with respect to FXIa inhibition, the test substances are examined for their inhibition of other human serin proteases, such as factor Xa, trypsin and plasmin To determine the enzymatic activity of factor Xa (1.3 nmol/l from Kordia), trypsin (83 mU/ml from Sigma) and plasmin (0.1 µg/ml from Kordia), these enzymes are dissolved (50 mmol/l of Tris buffer [C,C,C-tris(hydroxymethyl)aminomethane], 100 mmol/l of sodium chloride, 0.1% BSA [bovine serum albumin], 5 mmol/l of calcium chloride, pH 7.4) and incubated for 15 mm with test substance in various concentrations in dimethyl sulphoxide and also with dimethyl sulphoxide without test substance. The enzymatic reaction is then started by addition of the appropriate substrates (5 µmol/l of Boc-Ile-Glu-Gly-Arg-AMC from Bachem for factor Xa and trypsin, 50 µmol/l of MeOSuc-Ala-Phe-Lys-AMC from Bachem for plasmin). After an incubation time of 30 mm at 22° C., fluorescence is measured (excitation: 360 nm, emission: 460 nm). The measured emissions of the test mixtures with test substance are compared to the control mixtures without test substance (only dimethyl sulphoxide instead of test substance in dimethyl sulphoxide) and $IC_{50}$ values are calculated from the concentration/activity relationships.

a.3) Thrombin Generation Assay (Thrombogram)

The effect of the test substances on the thrombogram (thrombin generation assay according to Hemker) is determined in vitro in human plasma (Octaplas® from Octapharma).

In the thrombin generation assay according to Hemker, the activity of thrombin in coagulating plasma is determined by measuring the fluorescent cleavage products of the substrate I-1140 (Z-Gly-Gly-Arg-AMC, Bachem). The reactions are carried out in the presence of varying concentrations of test substance or the corresponding solvent. To start the reaction, reagents from Thrombinoscope (30 pM or 0.1 pM recombinant tissue factor, 24 µM phospholipids in HEPES) are used. In addition, a thrombin calibrator from Thrombinoscope is used whose amidolytic activity is required for calculating the thrombin activity in a sample containing an unknown amount of thrombin. The test is carried out according to the manufacturer's instructions (Thrombinoscope BV): 4 µl of test substance or of the solvent, 76 µl of plasma and 20 µl of PPP reagent or thrombin calibrator are incubated at 37° C. for 5 mM. After addition of 20 µl of 2.5 mM thrombin substrate in 20 mM HEPES, 60 mg/ml of BSA, 102 mM of calcium chloride, the thrombin generation is measured every 20 s over a period of 120 mM. Measurement is carried out using a fluorometer (Fluoroskan Ascent) from Thermo Electron fitted with a 390/460 nm filter pair and a dispenser.

Using the Thrombinoscope software, the thrombogram is calculated and represented graphically. The following parameters are calculated: lag time, time to peak, peak, ETP (endogenous thrombin potential) and start tail.

a.4) Determination of Anticoagulatory Activity

The anticoagulatory activity of the test substances is determined in vitro in human plasma and rat plasma. To this end, blood is drawn off in a mixing ratio of sodium citrate/blood of 1:9 using a 0.11 molar sodium citrate solution as receiver Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effects a doubling of the prothrombin time is determined.

The activated partial thromboplastin time (APTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects an extension by 50% or a doubling of the APTT is determined.

a.5) Determination of the Plasma Kallikrein Activity

To determine the plasma kallikrein inhibition of the substances according to the invention, a biochemical test system is used which utilizes the reaction of a peptidic plasma kallikrein substrate to determine the enzymatic activity of human plasma kallikrein. Here, plasma kallikrein cleaves from the peptic plasma kallikrein substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 µM to 0.0078 µM; resulting final concentrations in the test: 50 µM to 0.00013 µM). In each case 1 µl of the diluted substance solutions is placed into the wells of white microtitre plates from Greiner (384 wells). 20 µl of assay buffer (50 mM Tris/HCl pH 7.4; 100 mM sodium chloride solution; 5 mM of calcium chloride solution; 0.1% of bovine serum albumin) and 20 µl of plasma kallikrein from Kordia (0.6 nM in assay buffer) are then added successively. After 15 mM of incubation, the enzyme reaction is started by addition of 20 µl of the substrate H-Pro-Phe-Arg-AMC dissolved in assay buffer (10 µM in assay buffer) from Bachem, the mixture is incubated at room temperature (22° C.) for 30 mM and fluorescence is then measured (excitation: 360 nm, emission: 460 nM). The measured emissions of the test batches with test substance are compared to those of control batches without test substance (only dimethyl sulphoxide instead of test substance in dimethyl sulphoxide), and $IC_{50}$ values are calculated from the concentration/activity relationships.

a.6) Determination of Endothelium Integrity

The activity of the compounds according to the invention is characterized by means of an in vitro permeability assay on "human umbilical venous cells" (HUVEC). Using the EOS apparatus (EC IS: Electric Cell-substrate Impedance Sensing; Applied Biophysics Inc; Troy, N.Y.), it is possible to measure continuously variations in the transendothelial electrical resistance (TEER) across an endothelial cell monolayer plated over gold electrodes. HUVECs are sown on a 96-well sensor electrode plate (96W1 E, Ibidi GmbH, Martinsried, Germany). Hyperpermeability of the confluent cell monolayer formed is induced by stimulation with kininogen, prekallikrein and factor XII (100 nM each). The compounds according to the invention are added prior to the addition of the substances indicated above. The customary concentrations of the compounds are $1 \times 10^{-10}$ to $1 \times 10^{-6}$ M.

a.7) Determination of the In Vitro Permeability of Endothelial Cells

In a further hyperpermeability model, the activity of the substances on the modulation of macromolecular permeability is determined. HUVECs are sown on a fibronectin-coated Transwell filter membrane (24-well plates, 6.5 mm insert with 0.4 µM polycarbonate membrane; Costar #3413). The filter membrane separates the upper from the lower cell culture space, with the confluent endothelial cell layer on the floor of the upper cell culture space. 250 g/ml of 40 kDa FITC dextan (Invitrogen, D1844) are added to the medium of the upper chamber. Hyperpermeability of the monolayer is induced by stimulation with kininogen, prekallikrein and factor XII (100 nM each). Every 30 mm, medium samples are removed from the lower chamber and relative fluorescence as a parameter for changes in macromolecular permeability as a function of time is determined using a fluorimeter. The compounds according to the invention are added prior to the addition of the substances indicated above. The customary concentrations of the compounds are $1 \times 10^{-10}$ to $1 \times 10^{-6}$ M.

b) Determination of Antithrombotic Activity (In Vivo)

b.1) Arterial Thrombosis Model (Iron(II) Chloride-Induced Thrombosis) in Combination with Ear Bleeding Time in Rabbits The antithrombotic activity of the FXIa inhibitors is tested in an arterial thrombosis model. Thrombus formation is triggered here by causing chemical injury to a region in the carotid artery in rabbits. Simultaneously, the ear bleeding time is determined.

Male rabbits (Crl:KBL (NZW)BR, Charles River) receiving a normal diet and having a body weight of 2.2-2.5 kg are anaesthetized by intramuscular administration of xylazine and ketamine (Rompun, Bayer, 5 mg/kg and Ketavet, Pharmacia & Upjohn GmbH, 40 mg/kg body weight). Anaesthesia is furthermore maintained by intravenous administration of the same preparations (bolus: continuous infusion) via the right auricular vein.

The right carotid artery is exposed and the vessel injury is then caused by wrapping a piece of filter paper (10 mm×10 mm) on a Parafilm® strip (25 mm×12 mm) around the carotid artery without disturbing the blood flow. The filter paper contains 100 µL of a 13% strength solution of iron(II) chloride (Sigma) in water. After 5 mm, the filter paper is removed and the vessel is rinsed twice with aqueous 0.9% strength sodium chloride solution. 30 mm after the injury the injured region of the carotid artery is extracted surgically and any thrombotic material is removed and weighed.

The test substances are administered either intravenously to the anaesthetized animals via the femoral vein or orally to the awake animals via gavage, in each case 5 mm and 2 h, respectively, before the injury.

Ear bleeding time is determined 2 mm after injury to the carotid artery. To this end, the left ear is shaved and a defined 3-mm-long incision (blade Art. Number 10-150-10, Martin, Tuttlingen, Germany) is made parallel to the longitudinal axis of the ear. Care is taken here not to damage any visible vessels. Any blood that extravasates is taken up in 15 second intervals using accurately weighed filter paper pieces, without touching the wound directly. Bleeding time is calculated as the time from making the incision to the point in time where no more blood can be detected on the filter paper. The volume of the extravasated blood is calculated after weighing of the filter paper pieces.

c) Determination of the Effect on Extravasation/Oedema Formation and/or Neovascularization in the Eye (In Vivo)

c.1) Test of the Efficacy of Substances in the Laser-Induced Choroidal Neovascularization Model This study serves to investigate the efficacy of a test substance on reduction of extravasation/oedema formation and/or choroidal neovascularization in the rat model of laser-induced choroidal neovascularization.

To this end, pigmented rats of the Brown-Norway strain not showing any signs of ophthalmic disorders are selected and randomized into treatment groups. On day 0, the animals are anaesthetized by intraperitoneal injection (15 mg/kg xylazine and 80 mg/kg ketamine) Following instillation of a drop of a 0.5% strength tropicamide solution to dilate the pupils, choroidal neovascularization is triggered on six defined locations around the optical nerve using a 532 nm argon laser photocoagulator (diameter 50-75 µm, intensity 150 mW, duration 100 ms). The test substance and the appropriate vehicle (e.g. PBS, isotonic saline) are administered either systemically by the oral or intraperitonal route, or topically to the eye by repeated administration as eye drops or intravitreal injection. The body weight of all the animals is determined before the start of the study, and then daily during the study.

On day 21, an angiography is carried out using a fluorescence fundus camera (e.g. Kowe, HRA). Under anaesthesia and after another pupil dilation, a 10% strength sodium fluorescein dye is injected subcutaneously (s.c.). 2-10 mm later, pictures of the eye background are taken. The degree of extravasation/the oedema, represented by the leakage of fluorescein, is assessed by two to three blinded observers and classified into degrees of severity from 0 (no extravasation) to 3 (strong colouration exceeding the actual lesion).

The animals are sacrificed on day 23, after which the eyes are removed and fixated in 4% strength paraformaldehyde solution for one hour at room temperature. After one washing, the retina is carefully peeled off and the sclera-choroidea complex is stained using an FITC isolectin B4 antibody and then applied flat to a microscope slide. The preparations obtained in this manner are evaluated using a fluorescence microscope (Apotom, Zeiss) at an excitation wavelength of 488 nm. The area or volume of the choroidal neovascularization (in $\mu m^2$ and $\mu m^3$, respectively) is calculated by morphometric analysis using Axiovision 4.6 software.

c.2) Test of the Efficacy of Substances in the Oxygen-Induced Retinopathy Model

It has been shown that oxygen-induced retinopathy is a useful animal model for the study of pathological retinal angiogenesis. This model is based on the observation that hyperoxia during early postnatal development in the retina causes arrest or delay of the growth of normal retinal blood vessels. When, after a 7-day hyperoxia phase, the animals are returned to normoxic room air, this is equivalent to relative hypoxia since the retina is missing the normal vessels which are required to ensure adequate supply of the neural tissue under normoxic conditions. The ischemic situation caused in this manner results in an abnormal neovascularization which has some similarities with pathophysiological neovascularization in eye disorders such as wet AMD. In addition, the neovascularization caused is highly reproducible, quantifiable and an important parameter for examining the disease mechanisms and possible treatments for various forms of retinal disorders.

The aim of this study is to examine the efficacy of daily systemically administered doses of the test compound on the growth of retinal vessels in the oxygen-induced retinopathy model. Neonates of C57B1/6 mice and their mothers are exposed to hyperoxia (70% oxygen) on postnatal day 7 (PD7) for 5 days. From PD12, the mice are kept under normoxic conditions (room air, 21% oxygen) until PD17. From day 12 to day 17, the mice are treated daily with the test substance or the corresponding vehicle. On day 17, all mice are anaesthetized with isoflurane and then sacrificed by cervical fracture. The eyes are removed and fixated in 4% Formalin. After washing in phosphate-buffered saline, the retina is excised, a flat preparation thereof is produced and this is stained with isolectin B4 antibody. Quantification of neovascularization is carried out using a Zeiss ApoTome.

C) Working Examples of Pharmaceutical Compositions

The substances according to the invention can be converted to pharmaceutical preparations as follows:

Tablet:
Composition:
100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm

Production:
The mixture of the compound of Example 1, lactose and starch is granulated with a 5% strength solution (m/m) of the PVP in water. After drying, the granules are mixed with the magnesium stearate for 5 min. This mixture is compressed in a conventional tabletting press (see above for format of the tablet).

Oral Suspension:
Composition:
1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the inventive compound.

Production:
The Rhodigel is suspended in ethanol, and the compound of Example 1 is added to the suspension. The water is added while stirring. The mixture is stirred for about 6 h until swelling of the Rhodigel is complete.

Solution or Suspension for Topical Administration to the Eye (Eye Drops):

A sterile pharmaceutical preparation for topical administration to the eye can be prepared by reconstituting a lyophilisate of the inventive compound in sterile saline. Suitable preservatives for such a solution or suspension are, for example, benzalkonium chloride, thiomersal or phenylmercury nitrate in a concentration range of from 0.001 to 1 percent by weight.

The invention claimed is:

1. A method of treating or preventing at least one of a thrombotic disorder and a thromboembolic disorder comprising administering a therapeutically effective amount of a compound of the formula

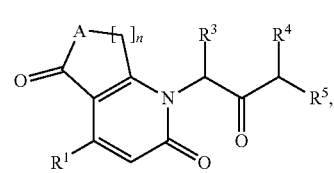

(I)

in which
n represents the number 1 or 2,
A represents —N(R$^2$)- or —CH$_2$—,
    wherein
R$^2$ represents hydrogen or C1-C4-alkyl,
R$^1$ represents a group of the formula

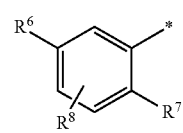

where * is the point of attachment to the oxopyridine ring,
R$^6$ represents bromine, chlorine, fluorine, methyl, difluoromethyl, trifluoromethyl, methoxy, difluoromethoxy or trifluoromethoxy,
R$^7$ represents hydrogen, bromine, chlorine, fluorine, cyano, nitro, hydroxy, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl,
R$^8$ represents hydrogen, chlorine or fluorine,
R$^3$ represents hydrogen,
R$^4$ represents hydrogen, $R^5$ represents a group of the formula

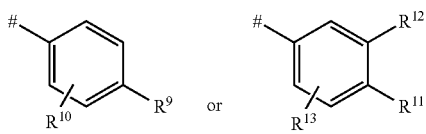

where # is the attachment site to the nitrogen atom,
$R^9$ represents hydroxycarbonyl or 5-membered heterocyclyl, where heterocyclyl may be substituted by 1 to 2 substituents independently of one another selected from the group consisting of oxo, hydroxy, thioxo, sulphanyl, methyl, difluoromethyl, trifluoromethyl, 2-hydroxycarbonyl-1,1,2,2-tetrafluoroethyl and 2-methoxycarbonyl-1,1,2,2-tetrafluoroethyl,
where methyl may be substituted by a methoxy substituent,
$R^{10}$ represents hydrogen, chlorine, fluorine or methyl,
$R^{11}$ and $R^{12}$ together with the carbon atoms to which they are bonded form a 5-membered heterocycle, where the heterocycle may be substituted by 1 to 2 substituents independently of one another selected from the group consisting of oxo, chlorine, hydroxy, hydroxycarbonyl, methyl, difluoromethyl, trifluoromethyl, 1,1,2,2,2-pentafluoroethyl, 2-hydroxycarbonyl-1,1,2,2-tetrafluoroethyl and 2-methoxycarbonyl- 1,1,2,2-tetrafluoroethyl,
$R^{13}$ represents hydrogen, chlorine, fluorine, methyl or methoxy, or one of the salts thereof.

2. A pharmaceutical composition comprising an active compound of the formula

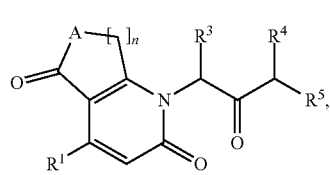

in which
n represents the number 1 or 2,
A represents —N($R^2$)- or —CH2—,
wherein
$R^2$ represents hydrogen or C1-C4-alkyl,
$R^1$ represents a group of the formula

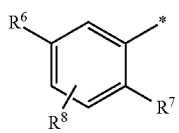

where * is the point of attachment to the oxopyridine ring,
$R^6$ represents bromine, chlorine, fluorine, methyl, difluoromethyl, trifluoromethyl, methoxy, difluoromethoxy or trifluoromethoxy,
$R^7$ represents hydrogen, bromine, chlorine, fluorine, cyano, nitro, hydroxy, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl,
$R^8$ represents hydrogen, chlorine or fluorine,
$R^3$ represents hydrogen,
$R^4$ represents hydrogen,
$R^5$ represents a group of the formula

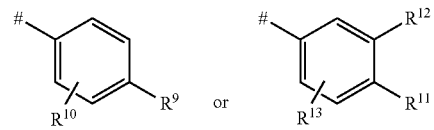

where # is the attachment site to the nitrogen atom,
$R^9$ represents hydroxycarbonyl or 5-membered heterocyclyl, where heterocyclyl may be substituted by 1 to 2 substituents independently of one another selected from the group consisting of oxo, hydroxy, thioxo, sulphanyl, methyl, difluoromethyl, trifluoromethyl, 2-hydroxycarbonyl-1,1,2,2-tetrafluoroethyl and 2-methoxycarbonyl-1,1,2,2-tetrafluoroethyl,
where methyl may be substituted by a methoxy substituent,
$R^{10}$ represents hydrogen, chlorine, fluorine or methyl,
$R^{11}$ and $R^{12}$ together with the carbon atoms to which they are bonded form a 5-membered heterocycle, where the heterocycle may be substituted by 1 to 2 substituents independently of one another selected from the group consisting of oxo, chlorine, hydroxy, hydroxycarbonyl, methyl, difluoromethyl, trifluoromethyl, 1,1,2,2,2-pentafluoroethyl, 2-hydroxycarbonyl-1,1,2,2-tetrafluoroethyl and 2-methoxycarbonyl-1,1,2,2-tetrafluoroethyl,
$R^{13}$ represents hydrogen, chlorine, fluorine, methyl or methoxy,
or one of the salts thereof combined with one or more inert nontoxic pharmaceutically suitable excipients.

3. A method of treating or preventing at least one of a thrombotic disorder and a thromboembolic disorder comprising administering a therapeutically effective amount of the medicament of claim 2.

* * * * *